United States Patent
Kang et al.

(10) Patent No.: US 10,115,198 B2
(45) Date of Patent: Oct. 30, 2018

(54) METHODS OF OBTAINING GEOMETRY FROM IMAGES

(71) Applicant: Bio-Tree Systems, Inc., Framingham, MA (US)

(72) Inventors: Kongbin Kang, Providence, RI (US); Raul A. Brauner, Framingham, MA (US); Yanchun Wu, Sharon, MA (US); Joao Cruz, Rumford, RI (US)

(73) Assignee: Bio-Tree Systems, Inc., Framingham, MA (US)

( * ) Notice: Subject to any disclaimer, the term of this patent is extended or adjusted under 35 U.S.C. 154(b) by 0 days.

(21) Appl. No.: 15/632,650

(22) Filed: Jun. 26, 2017

(65) Prior Publication Data

US 2018/0040122 A1 Feb. 8, 2018

Related U.S. Application Data

(60) Continuation of application No. 15/043,345, filed on Feb. 12, 2016, now Pat. No. 9,721,341, which is a (Continued)

(51) Int. Cl.
*G06K 9/00* (2006.01)
*G06T 7/00* (2017.01)
(Continued)

(52) U.S. Cl.
CPC ........ *G06T 7/0012* (2013.01); *A61B 5/02007* (2013.01); *A61B 5/055* (2013.01);
(Continued)

(58) Field of Classification Search
CPC . G06T 7/0012; G06T 7/11; G06T 7/60; G06T 7/62; G06T 7/64; G06T 7/66;
(Continued)

(56) References Cited

U.S. PATENT DOCUMENTS 5,724,435 A * 3/1998 Malzbender ............ G06T 5/006
382/103
6,047,090 A 4/2000 Makram-Ebeid
(Continued)

FOREIGN PATENT DOCUMENTS

KR 10-2006-0085530 A 7/2006

OTHER PUBLICATIONS

William E. Hart, Michael Goldbaum, Brad Cote, Paul Kube, and Mark R. Nelson, "Measurement and classification of retinal vascular tortuosity", Elsevier, International Journal of Medical Informatics, vol. 53, Feb. 1999, pp. 239-252.*
(Continued)

*Primary Examiner* — Eric Rush
(74) *Attorney, Agent, or Firm* — Nields, Lemack & Frame, LLC

(57) ABSTRACT

In one aspect, a method of detecting at least on feature associated with a blood vessel in at least one image of at least one blood vessel using a matched filter adapted to respond to the at least one feature is provided. The method comprises applying a scale detection filter to selected voxels in the at least one image to determine a scale for the matched filter at each of the selected voxels, determining an orientation for the matched filter at each of the selected voxels, wherein determining the orientation is assisted by using the scale determined at each of the selected voxels, applying the matched filter at each of the selected voxels at the scale and the orientation determined at each of the selected voxels to obtain a filter response at each of the selected voxels, and analyzing the filter response at each of the selected voxels to determine if the respective voxel corresponds to the at least one feature.

12 Claims, 18 Drawing Sheets

Related U.S. Application Data continuation of application No. 14/288,302, filed on May 27, 2014, now abandoned, which is a division of application No. 12/811,537, filed as application No. PCT/US2009/000008 on Jan. 2, 2009, now Pat. No. 8,761,466.

(60) Provisional application No. 61/010,080, filed on Jan. 3, 2008, provisional application No. 61/009,872, filed on Jan. 2, 2008.

(51) Int. Cl.

| | | |
|---|---|---|
| *A61B 5/055* | (2006.01) | |
| *A61B 6/00* | (2006.01) | |
| *G06T 15/08* | (2011.01) | |
| *G06K 9/62* | (2006.01) | |
| *G06T 7/60* | (2017.01) | |
| *G06T 7/20* | (2017.01) | |
| *G06T 7/73* | (2017.01) | |
| *G06K 9/46* | (2006.01) | |
| *G06T 7/62* | (2017.01) | |
| *A61B 5/107* | (2006.01) | |
| *A61B 5/00* | (2006.01) | |
| *A61B 5/02* | (2006.01) | |

(52) U.S. Cl.
CPC .............. *A61B 5/107* (2013.01); *A61B 5/489* (2013.01); *A61B 6/504* (2013.01); *G06K 9/4609* (2013.01); *G06K 9/4638* (2013.01); *G06K 9/6215* (2013.01); *G06T 7/20* (2013.01); *G06T 7/60* (2013.01); *G06T 7/62* (2017.01); *G06T 7/74* (2017.01); *G06T 15/08* (2013.01); *A61B 6/508* (2013.01); *A61B 2576/02* (2013.01); *G06T 2207/10028* (2013.01); *G06T 2207/10072* (2013.01); *G06T 2207/10116* (2013.01); *G06T 2207/20004* (2013.01); *G06T 2207/30101* (2013.01); *G06T 2207/30172* (2013.01); *G06T 2211/404* (2013.01)

(58) Field of Classification Search
CPC .... G06T 7/68; G06T 7/70; G06T 7/73; G06T 7/74; G06T 7/75; G06T 7/77; G06T 7/97; G06T 2207/30004; G06T 2207/30101; G06T 2207/30104; G06T 2207/30172; G06T 11/005; G06T 2211/404; G06K 9/34; G06K 9/342; G06K 9/46; G06K 9/4604; G06K 9/4609; G06K 9/4638; G06K 9/468; G06K 9/50; G06K 9/52; G06K 2209/00932; G06K 2209/05; G06K 2209/051; A61B 5/02; A61B 5/02007; A61B 5/026; A61B 5/107; A61B 5/1071; A61B 5/1072; A61B 5/1073; A61B 5/1075; A61B 5/1076; A61B 5/1079; A61B 5/489; A61B 5/72; A61B 6/503; A61B 6/504; A61B 6/5217
USPC ....... 382/100, 128, 131, 132, 151, 154, 260, 382/286–288, 291, 294; 128/922; 600/481, 504, 507; 378/4, 20
See application file for complete search history.

(56) References Cited

U.S. PATENT DOCUMENTS

| | | |
|---|---|---|
| 6,048,314 A | 4/2000 | Nikom |
| 7,024,027 B1 | 4/2006 | Suri et al. |
| 8,160,332 B2 | 4/2012 | Von Berg et al. |
| 8,761,466 B2 | 6/2014 | Kang et al. |
| 9,721,341 B2 | 8/2017 | Kang et al. |
| 2003/0053697 A1* | 3/2003 | Aylward .............. G06T 7/0012 382/203 |
| 2005/0147297 A1* | 7/2005 | McLaughlin .......... G06K 9/342 382/171 |
| 2006/0182327 A1* | 8/2006 | Mundy .................. A61B 6/032 382/132 |
| 2006/0269108 A1 | 11/2006 | Viswanathan |
| 2006/0285755 A1 | 12/2006 | Hager et al. |
| 2007/0019846 A1* | 1/2007 | Bullitt ................... G06T 7/0014 382/128 |
| 2007/0116332 A1 | 5/2007 | Cai et al. |
| 2007/0165921 A1* | 7/2007 | Agam ................... G06T 7/0012 382/128 |
| 2008/0118135 A1 | 5/2008 | Averbuch et al. |
| 2008/0247622 A1 | 10/2008 | Aylward et al. |
| 2010/0104168 A1 | 4/2010 | Dobbe |
| 2010/0316277 A1 | 12/2010 | Fan et al. |
| 2011/0103657 A1 | 5/2011 | Kang et al. |
| 2015/0287183 A1 | 10/2015 | Kang et al. |
| 2017/0024882 A1 | 1/2017 | Kang et al. |

OTHER PUBLICATIONS

S. B. Abramson and F. S. Fay, "Application of Multiresolution Spatial Filters to Long-Axis Tracking", IEEE, Transactions on Medical Imaging, vol. 9, No. 2, Jun. 1990, pp. 151-158.*
Liang Zhou, Mark S. Rzeszotarski, Lawrence J. Singerman, and Jeanne M. Choreff, "The Detection and Quantification of Retinopathy Using Digital Angiograms", IEEE, Transactions on Medical Imaging, vol. 13, No. 4, Dec. 1994, pp. 619-626.*
Indian communication dated Oct. 12, 2017 in corresponding Indian patent application No. 5525/DELNP/2010.
International Search Report and Written Opinion dated Jul. 22, 2009 in corresponding PCT application No. PCT/US2009/000008.
Canadian communication dated Dec. 12, 2016 in corresponding Canadian patent application No. 2,748,854.
European communication dated Oct. 9, 2017 in corresponding European patent application No. 09700916.1.
Chutatape et al. "Retinal blood vessel detection and tracking by matched Gaussian and Kalman filters," Nov. 1998, IEEE, vol. 6, pp. 3144-3149.
Kirbas et al., "A Review of Vessel Extraction Techniques and Algorithms," ACM Computing Surveys, vol. 36, No. 2, Jun. 2004, pp. 81-121.
Lian et al., "Retinal Vessel Detection Using Self-Matched Filtering," IEEE International Conference on Image Processing, Sep. 1, 2007.
Miles et al. "Matched filter estimation of serial blood vessel diameters from video images," Jun. 1993, IEEE Transactions on Medical Imaging, vol. 12, No. 2, pp. 147-152.
Sofka et al. "Retinal Vessel Centerline Extraction Using Multiscale Matched Filters, Confidence and Edge Measures," Dec. 2006, IEEE Transactions on Medical Imaging, vol. 25, No. 12, pp. 1531-1546.
Sun, "Automated identification of vessel contours in coronary arteriograms by an adaptive tracking algorithm," IEEE Transactions on Medical Imaging, vol. 8, No. 1, pp. 78-88, Mar. 1989.
Office action dated Aug. 13, 2015 in related U.S. Appl. No. 14/288,302.
Canadian communication dated Apr. 20, 2018 in corresponding Canadian patent application No. 2,748,854.

* cited by examiner

METHODS OF OBTAINING GEOMETRY FROM IMAGES

RELATED APPLICATIONS

This application is a continuation of U.S. application Ser. No. 15/043,345 entitled "METHODS OF OBTAINING GEOMETRY FROM IMAGES," Filed Feb. 12, 2016, which claims the benefit under 35 U.S.C. § 120 and is a continuation of U.S. application Ser. No. 14/288,302 entitled "METHODS OF OBTAINING GEOMETRY FROM IMAGES," Filed May 27, 2014 (abandoned), which claims the benefit under 35 U.S.C. §§ 120 and 121 and is a divisional of U.S. patent application Ser. No. 12/811,537 entitled "METHODS OF OBTAINING GEOMETRY FROM IMAGES," Filed Jan. 3, 2011 (U.S. Pat. No. 8,761,466, Issued Jun. 24, 2014), which is a national stage application under 35 U.S.C. § 371 of International Application No. PCT/US2009/000008 entitled "METHODS OF OBTAINING GEOMETRY FROM IMAGES," Filed on Jan. 2, 2009, which claims priority under 35 U.S.C. § 119(e) to U.S. Provisional Application Ser. No. 61/009,872 entitled "METHODS OF ANALYZING VESSEL DISTRIBUTIONS AND USES THEREOF," Filed on Jan. 2, 2008, and U.S. Provisional Application Ser. No. 61/010,080 entitled "METHODS OF ANALYZING VESSEL DISTRIBUTIONS AND USES THEREOF," Filed on Jan. 3, 2008, each of which are herein incorporated by reference in their entirety.

FIELD OF THE INVENTION

Aspects of the present invention relate to extracting geometry from one or more images for use in analyzing biological tubular structures for diagnostic and therapeutic applications in animals. In particular, aspects of the invention relate to extracting geometry from images of blood vessels to identify structural features useful for detecting, monitoring, and/or treating diseases, and/or for evaluating and validating new therapies.

BACKGROUND OF THE INVENTION

A wide range of imaging methods and devices are commonly used to evaluate different anatomical and physiological conditions in a variety of medical and research environments. Tools have been developed to image body structures based on different physical properties. For example, X-rays, CT scans, MRIs, PET scans, IR analyses and other technologies have been developed to obtain images of various body structures. These tools are routinely used for diagnostic, therapeutic, and research applications. Combinations of two or more different imaging techniques are sometimes used to provide complementary information about a patient.

In conventional medical imaging, a human operator, such as a physician or diagnostician, may visually inspect one or more images to make an assessment, such as detection of a tumor or other pathology or to otherwise characterize the internal structures of a patient. However, this process may be difficult and time consuming. For example, it may be difficult to assess 3D biological structure by attempting to follow 2D structure through a series of stacked 2D images. In particular, it may be perceptually difficult and time consuming to understand how 2D structure is related to 3D structure as it appears, changes in size and shape, and/or disappears in successive 2D image slices. A physician may have to mentally arrange hundreds or more 2D slices into a 3D picture of the anatomy. To further frustrate this process, when anatomical structure of interest is small, the structure may be difficult to discern or it may be difficult to understand how numerous structures relate to a biological whole.

Furthermore, in addition to the time consuming nature of manual inspection, human visual interpretation of images has further shortcomings. While the human visual cortex processes image information to obtain qualitative information about structure in the image, it does not compute quantitative geometry from the image. However, the quantitative geometry of the structure represented in one or more images may contain valuable information about the structure that can be used to diagnose disease, assess the efficacy of treatment and/or perform other analyses of the structure. Such quantitative information about the structure is beyond the capability of conventional human visual image understanding alone.

Image processing techniques have been developed to automate or partially automate the task of understanding and partitioning the structure in an image and are employed in computer aided diagnosis (CAD) to assist a physician in identifying and locating structure of interest in a 2D or 3D image. CAD techniques often involve segmenting the image into groups of related pixels and identifying the various groups of pixels, for example, as those comprising a tumor or a vessel or some other structure of interest. However, conventional segmentation may produce unsatisfactory or incomplete results, particularly when the structure being detected appears in the image at arbitrary locations, sizes and orientations. As a result, the limited geometry that may be extracted from conventional image processing may be unsuitable for use in further analysis based on the extracted geometry.

SUMMARY OF THE INVENTION

Applicant has developed methods and apparatus for extracting geometry from images, scan data, and/or representations of tubular body structures (e.g., blood vessels or other body vessels). Aspects of the invention relate to obtaining vessel geometry, determining one or more structural features from the vessel geometry, and/or analyzing the one or more structural features for medical diagnostic, prognostic, and/or research applications.

Applicant has developed methods and apparatus for extracting geometry from images, scan data, and/or representations of tubular body structures (e.g., blood vessels or other body vessels). Aspects of the invention are useful for obtaining a geometrical representation of a vascular tree that contains data relating to three-dimensional location, orientation and/or size at any point in the vascular tree of a subject. In some embodiments, a vascular tree may be represented by a series of disks or poker chips (e.g., circular or elliptical disks) that are linked together to form a three-dimensional structure containing information relating to the local size, shape, branching, and other structural features at any point in the vascular tree.

It should be appreciated that the entire vascular tree of a subject may be represented by a network of linked poker chips (e.g., circular or elliptical disks). However, in many embodiments, only a subset or a portion of a vascular tree may be represented or analyzed. In some embodiments, a portion of a vascular tree can be represented by a single disc or poker chip that contains information relating to the location of the center of the vessel, vessel size (diameter), and/or orientation (e.g., the direction of the centerline of the vessel). In some embodiments, a portion of a vascular tree may be represented by a dataset that describes one or more poker chips along with information relating to the linkage between the poker chips within a region of interest of the vascular tree.

Some embodiments includes a method of detecting at least one feature associated with a blood vessel in at least one image of at least one blood vessel using a matched filter adapted to respond to the at least one feature, the method comprising applying a scale detection filter to selected voxels in the at least one image to determine a scale for the matched filter at each of the selected voxels, determining an orientation for the matched filter at each of the selected voxels, wherein determining the orientation is assisted by using the scale determined at each of the selected voxels, applying the matched filter at each of the selected voxels at the scale and the orientation determined at each of the selected voxels to obtain a filter response at each of the selected voxels, and analyzing the filter response at each of the selected voxels to determine if the respective voxel corresponds to the at least one feature.

According to some embodiments, the at least one feature includes the intensity at centerline voxels, which are detected using a matched filter, wherein the detected centerline voxels are further analyzed to link the centerline voxels together to provide adjacency and vessel membership information.

Some embodiments include applying an orientation independent scale filter that is invariant to direction to detect scale at voxels in the image. Some embodiments include an orientation independent scale filter that is independent of orientation detection and/or feature detection. Some embodiments include a first derivative orientation detection operation performed separately from scale detection. Some embodiments include a matched filter using a step function to detect vessels, the matched filter being applied using the scale and orientation determined during the separate scale detection and orientation detection.

Some embodiments include a method of determining a scale at each of a plurality of selected voxels in at least one image of at least one blood vessel, the scale at each of the plurality of selected voxels being determined using an orientation independent scale detection filter having a filter size defined by a radius, wherein the scale is used to determine the size of a matched filter adapted to respond to at least one feature associated with the at least one blood vessel, the method comprising (A) selecting a target voxel from the plurality of selected voxels at which to determine the scale, (B) setting the radius to a predetermined minimum value so that the filter size is at a predetermined minimum, (C) applying the orientation independent scale detection filter at the target voxel to obtain a filter response, (D) comparing the filter response with a predetermined criteria, (E) increasing the value of the radius of the orientation independent scale detection filter to increase the filter size of the orientation independent scale detection filter if the filter response meets the predetermined criteria, (F) performing acts (A)-(F) with increased filter size if the filter response meets the predetermined criteria, and (G) setting the scale based on the value of the radius of the orientation independent scale detection filter if the filter response does not meet the predetermined criteria.

Some embodiments include a method of linking geometry obtained from at least one image of at least one blood vessel, the geometry including a plurality of locations in the at least one image determined to be associated with voxels representing the centerline of a vessel, each of the plurality of locations having an associated orientation indicative of a direction of the centerline of the vessel and an associated filter response resulting from applying a centerline filter centered at the respective location, the method comprising linking centerline voxels based on one or more of the following parameters: a distance between centerline voxels; a change in the orientation of the centerline between centerline voxels; a change in the filter response between centerline voxels; and a change in vessel radius between centerline voxels. The centerline voxels may be linked to form a linked Poker Chip representation.

Some embodiments include a method of linking geometry obtained from at least one image of at least one blood vessel, the geometry including a plurality of locations in the at least one image determined to be associated with voxels representing the centerline of a vessel, each of the plurality of locations having an associated orientation indicative of a direction of a centerline of the vessel and an associated filter response resulting from applying a centerline filter centered at the respective location. The method comprises selecting a target location from the plurality of locations, comparing the target location with each other location in the plurality of locations within a predetermined neighborhood, wherein comparing includes, determining a distance between the target location and each of the other locations, determining a difference between the orientation at the target location and the orientation at each of the other plurality of locations, and determining a difference between the filter response at the target location and the filter response at each of the other plurality of locations, and linking the voxel associated with the target location with the voxel associated with one of the other locations based, at least in part, on the comparison.

According to aspects of the invention, a poker chip representation of a vasculature may be mined for physiological, biological, and/or medical purposes. In some embodiments, geometrical information associated with a single poker chip may be mined. In some embodiments, geometrical information associated with a plurality of poker chips, optionally including local linkage information may be mined.

Accordingly, aspects of the invention relate to obtaining vessel geometry, determining one or more structural features from the vessel geometry, and/or analyzing the one or more structural features for medical diagnostic, prognostic, and/or research applications.

Aspects of the invention provide methods for analyzing structures such as blood vessels and evaluating their association with disease, responsiveness to therapeutic treatments, and/or other conditions. Aspects of the invention provide quantitative and analytical methods for evaluating and/or comparing the vessels in different regions of the same body (e.g., a human body) or within ex vivo tissues or between different bodies (e.g., the same regions in different bodies) or different ex vivo tissues. Aspects of the invention can be useful in assisting and/or automating the analysis of vascular patterns and their association with disease diagnosis, prognosis, response to therapy, etc., or any combination thereof. Aspects of the invention can be used in connection with vessel structural information that is obtained from vessel images (e.g., blood vessel images), scan data, vessel representations (e.g., a reconstructed vasculature, a representation that can be viewed as being similar in some ways to a stack of poker chips with varying diameters and is that is referred to herein as a Poker Chip representation, or any other useful representation, or any combination thereof).

Methods are provided for analyzing vessel structural features, and blood vessel structural features in particular. In some embodiments, a distribution of vessel parameters (e.g., structural features or morphological parameters) within a region of interest may be generated and evaluated. In some embodiments, the vessel parameters may relate to the size, shape, or number of vessels with a region of interest. A distribution may be generated based on quantitative measurements related to one or more parameters. In some embodiments, a distribution of blood vessels may be a population distribution of blood vessels as a function of quantitative measures of one or more parameters. For example, a distribution may represent the number of blood vessels (or the percentage of the blood vessel population) as a function of their diameter, branching frequency, distance between branches, degree of tortuosity, curvature, or any other quantitative structural feature or morphological parameter, e.g., as described herein, or any combination of two or more thereof. In some embodiments, a distribution may be divided into groups or bins representing different value ranges of the quantitative measurements (e.g., ranges of vessel diameters such as 0-30 microns, 30-60 microns, 60-90 microns, 90-120 microns, 120-150 microns, 150-180 microns, etc., or any combination thereof). It should be appreciated that a distribution may be represented in any suitable form, for example graphically (e.g., a graph or histogram), in the form of a table, as a database, in a computer-readable or computer storage medium, etc., or any combination thereof.

DETAILED DESCRIPTION

Figure 1:
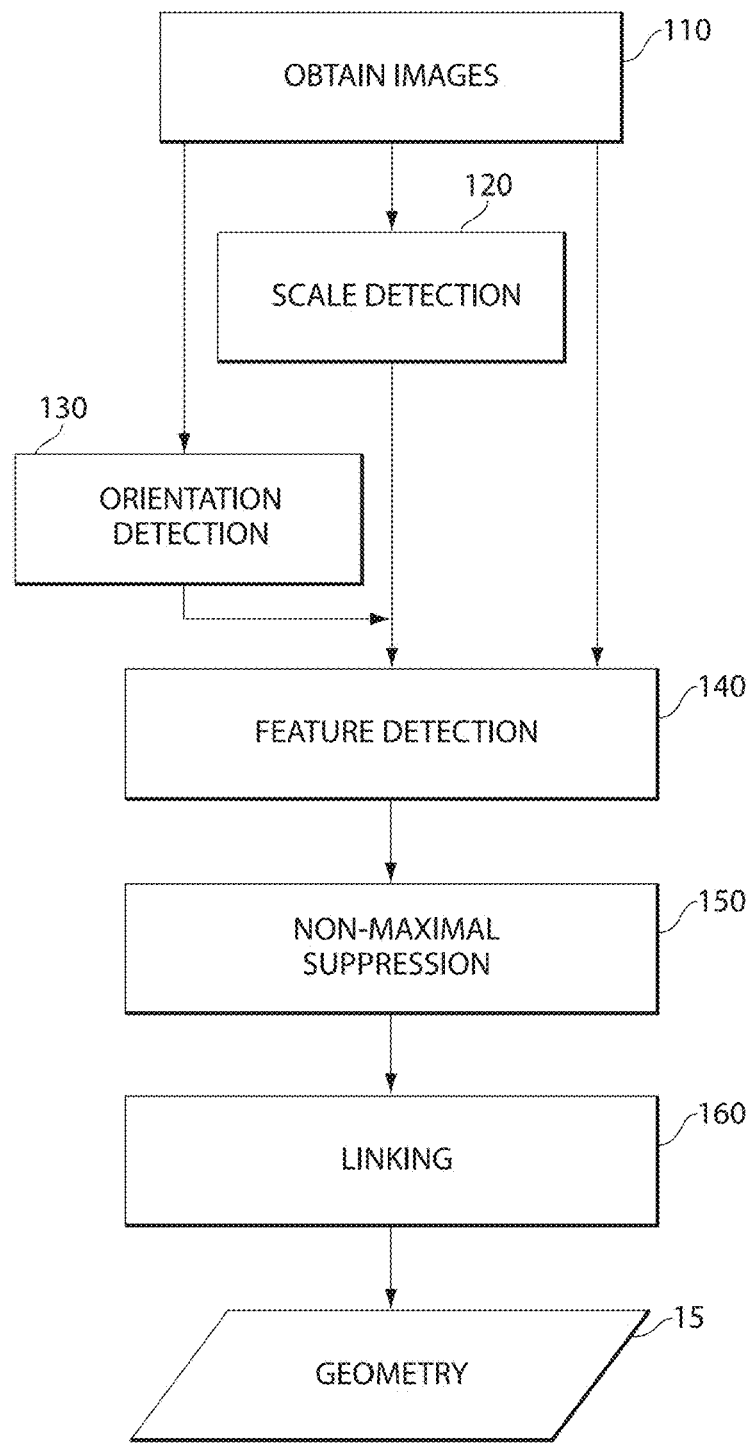
FIG. 1 illustrates a flow chart of extracting geometry from an image, in accordance with some embodiments of the invention.

As discussed above, analyzing vessel structures (e.g., blood vessel structures) and identifying structural profiles that are characteristic of one or more physiological conditions or responses (e.g., positive responses to pharmaceutical compounds) may be of interest in many areas of diagnostics, therapeutics and/or treatment. However, the amount of information that can be directly obtained or ascertained from image data (e.g., x-ray, CT, MRI, etc.) may be prohibitively limited in this respect. Accordingly, Applicant has recognized the benefit of developing methods of extracting geometry from images to facilitate the above described analysis.

To extract geometrical properties of vessel structures in one or more images, the vessels must first be detected in the image and represented in a meaningful fashion. Various methods have been proposed for detecting one or more features of a blood vessel using a filter adapted to respond to the one or more features. For example, filters have been designed to respond to the intensity profile of a vessel to locate voxels that exhibit this intensity profile. However, conventional filtering techniques may be unsatisfactory at accurately and robustly detecting vessel structures in one or more images. Filtering techniques typically require some additional preprocessing to obtain information about the image to improve the filtering process. For example, the scale of the structure at a particular location in the image may be obtained to determine what size filter should be used at that location. That is, not only should the filter match the feature being detected, in order to respond correctly, the filter should also match the scale of the feature. Moreover, because the orientation of the feature being detected is not known a priori, filtering techniques often include some preprocessing to determine the orientation of the feature at a particular location so that the filter can be applied to the image in general alignment with the feature.

Conventionally, scale detection and orientation detection are performed simultaneously. Applicant has appreciated that simultaneous scale and orientation detection may result in sub-optimal detection of either scale, orientation or both. As a result, subsequent filtering to detect one or more features applied using sub-optimal scale and orientation parameters may be substantially degraded. Applicant has developed a method for detecting vessel features that includes a scale detection operation and an orientation detection operation that are performed separately. In some embodiments, scale detection is performed prior to orientation detection, and orientation detection is performed using the scale determined by the scale detection. The scale and orientation values determined from the separate scale and orientation detection operations may then be used to apply the feature detection filter, for example, a centerline filter adapted to respond to the centerline voxels of blood vessels.

According to some embodiments, scale detection employs an orientation independent scale detector such that scale detection may be performed independent of orientation detection. According to some embodiments, an orientation independent scale filter is used having a filter kernel that is symmetric with respect to orientation such that the filter does not rely on orientation for accurate scale detection. According to some embodiments, the orientation independent scale filter includes a filter size defined by a radius. At each of a plurality of selected voxels in an image, the orientation independent scale filter is applied at increasing radii until the filter response fails to meet a predetermined criteria. The largest radius at which the filter response meets the predetermined criteria is used to represent the scale. According to some embodiments, the diameter of vessel structures in the images is determined based on this largest radius. That is, according to some embodiments, at least some geometry of vessel structures may be determined by the scale detection operation.

Applicant has appreciated that performing scale detection, orientation detection and centerline detection provides, at each detected centerline voxel, the location, the direction of the centerline and the radius of the vessel. This geometry can be used to analyze vascular structure and these geometrical parameters have been used to develop a mathematical representation of the detected vessel structure. In some embodiments, each centerline location may be represented as a circular or elliptical disk having a center at the centerline location, a radius corresponding to the associated scale, and a normal vector to the disk (e.g., circular disk) corresponding to the direction of the centerline as determined during orientation detection. This representation resembles a poker chip and is referred to herein as the Poker Chip representation, as described in further detail below.

While the Poker Chip representation provides much useful information about the geometry of the vessel, without further processing, there is no notion of adjacency or vessel membership, which may be useful information in performing analysis on the vasculature. Accordingly, in some embodiments, each of the detected centerline voxels (e.g., center locations of a poker chip) are linked together to capture adjacency information as well as vessel membership. In some embodiments, the centerline voxels are linked according to a criteria that includes one or any combination of minimizing a distance, a direction change, a radius change and/or a filter response change from a centerline voxel to an adjacent centerline voxel. That is, when selecting between a number of candidate centerline voxels to link to a target centerline voxel, the centerline voxel candidate that creates the smallest change in one or more of the above parameters may be preferred over candidate centerline voxels having larger changes. The linked centerline voxels can then be used to compute various structural characteristics of the vasculature formed by the detected vessels as represented by the stacked and linked poker chips.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments below may be used alone or in any combination, and are not limited to the combinations explicitly described herein.

FIG. 1 illustrates a method of extracting vessel geometry from one or more images of vasculature, in accordance with some embodiments of the present invention. Act 110 includes obtaining image information of at least a portion of a vasculature structure. For example, the image information may be a two-dimensional (2D), three-dimensional (3D) or other dimensional image obtained from scanning an object using x-ray CT, MRI, PET, SPECT, etc. The scanned object may be a live specimen such as a human or other animal (i.e., an in-vivo scan), or obtained from a cast of a specimen's vasculature.

The method of FIG. 1 may be performed on any image of any dimension independent of how the image was obtained, as the aspects of the invention are not limited in this respect. In 2D images, each 2D location having an associated intensity is conventionally referred to as a pixel. In 3D images, each volume location having an associated intensity is conventionally referred to as a voxel. The term voxel is used herein to refer to both 2D and 3D image locations to eliminate the need to specify the dimensionality of the images, as the methods described herein are generic to dimensionality.

Many techniques for extracting information from images use various filtering techniques. For example, filters are often designed such that when applied to a portion of an image (e.g., convolved with a portion of the image) the filter response is relatively large when the filter is applied to an image portion having a feature or characteristic indicative of structure being detected in the image, and relatively small otherwise. The filter detection described below in connection with act 140 is one example of matched filtering. However, other filtering techniques may be used, as the aspects of the invention are not limited in this respect.

When the feature or structure being detected appears in an image at different sizes or scales, the size of the filter kernel should be adjusted to the appropriate scale in order for the filter response to accurately indicate the presence of the desired feature. For example, in an image containing biological vasculature, and in particular, tumor vasculature, the constituent vessels will typically vary greatly in diameter. Accordingly, a filter designed to detect relatively large vessels will not respond accordingly to small vessels, even when applied on the correct location. However, it is not known a priori where large and small vessels are located. Accordingly, successful detection may require determining the scale of the structure in the image prior to applying the filter. This technique is herein referred to as "scale detection." Scale detection may be performed on predetermined portions of an image, or may be determined on a voxel by voxel basis, as described in further detail below.

In addition to detecting the appropriate scale, it may be beneficial to detect the orientation in which the filter should be applied. In particular, the feature(s) being detected may appear in the image at arbitrary orientations. For example, in the case of vasculature, the vessel properties being detected may be oriented in any arbitrary direction. Accordingly, even if a filter at the appropriate scale is applied at an image region corresponding to the feature being detected, the filter response may be relatively low if it is not oriented in general alignment with the direction of the feature for which the filter was designed to detect. Accordingly, determining the orientation of the features or properties being detected may benefit filter detection techniques. This technique is herein referred to as "orientation detection."

Conventional filtering techniques combine scale and orientation detection in a single operation. That is, the combination of possible scales and orientations are tested simultaneously and the scale and orientation are selected when the response is maximum. However, Applicant has appreciated that maximum responses may not correspond to optimal scale and optimal orientation simultaneously. Because the response is a combination of scale and orientation, one or both may be sub-optimal while together providing a strong response. Applicant has developed a scale detection operation that is orientation independent. As a result, the operations of scale detection and orientation detection may be separated into two separate operations. In addition, the detected scale may then be used to improve subsequent orientation detection processes.

In act 120, scale detection is performed independently of orientation detection. In some embodiments, scale detection 120 is performed using a filter that is independent of orientation. Scale detection 120 may provide the scale in the image at different regions in the image. In some embodiments, scale detection 120 determines scale at each voxel in the image. Alternatively, a preprocessing operation may be performed to roughly determine which voxels in the image correspond to subject matter of interest (e.g., vessels) and which voxels correspond to background. Scale detection may then be performed only on pixels determined to correspond to subject matter of interest, thus reducing the amount of computations. The result of scale detection is a scale associated with each location at which the filter was applied (e.g., a scale at each selected voxel in the image). An orientation independent scale detection algorithm according to some embodiments is described in further detail below.

In act 130, orientation detection may be performed. To assist in more accurate orientation detection, the scale at the selected regions of the image determined during scale detection 120 may be provided to the orientation detection operation. As discussed above, determining the orientation of subject matter of interest in one or more images may be important for accurate filter detection of the subject matter of interest (e.g., structure, feature, property or characteristic). For example, in embodiments where the subject matter of interest is vasculature, it may be important to detect the direction of the center or longitudinal axis of the vessels before applying a filter that detects the centerline of the vessel. In some embodiments, the scale determined from scale detection 120 may be used to improve orientation detection accuracy. The result of orientation detection is an orientation or direction at each selected voxel indicating the direction of the centerline at the respective location. An orientation detection algorithm according to some embodiments is described in further detail below.

In act 140, filter detection may be performed. In filter detection 140, a filter designed to respond to the subject matter of interest in the image may be applied. In some embodiments, the filter is applied at the scale and/or orientation determined from scale detection and/or orientation detection, respectively. The magnitude of the filter response at selected locations in the image indicates the likelihood that the location includes the subject matter of interest. In some embodiments, the subject matter of interest is vasculature and the filter is designed to respond to the center of a vessel. That is, the filter may be designed to respond to the intensity profile across a vessel and thus respond most strongly when centered on a centerline voxel in the direction of the intensity profile. Because the scale and direction of the subject matter of interest has been determined at selected locations in the image, filter detection may appropriately accurate in detecting the subject matter of interest. Several methods of centerline filtering are discussed in detail below, in accordance with some embodiments of the present invention.

In act 150, non-maximal suppression may be performed on the output of the filter detection operation performed in act 140. As discussed above, the result of a filtering operation (e.g., centerline filtering) generally includes the filter response at each voxel at which the filter was applied. The magnitude of the response is typically proportional to the likelihood that the feature being detected is present at the corresponding voxel location. However, it should be appreciated that many voxel locations will have associated non-zero filter responses. In addition, some voxel locations will have associated local maximum filter responses even though the true location of the feature is elsewhere. However, accurate detection may require discriminating between local maximum and the true maximum location, which corresponds to the most likely location of the structure being detected. Non-maximal suppression 150 attempts to eliminate or suppress all but the true maximum filter responses to accurately detect the subject matter of interest. A detailed description of non-maximum suppression in the context of centerline filtering for vessel detection is described below.

In act 160, linking may be performed. Linking may include various operations that associate voxel locations with each other to form related structures so that geometric properties may be obtained from the linked voxels. For example, in the context of vessel detection, the voxel locations that were determined as centerline voxels after centerline detection and non-maximum suppression may be linked together to form the associated centerline of vessels. That is, analysis may be performed to link together centerline voxels that are likely to have arisen from the same vessel structure. In such a way, the geometry of the vessels may be obtained (e.g., geometry 15). Methods for linking voxels in the context of vessel detection are described in further detail below.

As discussed above, some embodiments are directed to detecting vasculature and extracting the geometry of the vasculature to facilitate various analysis such as diagnosis, therapeutics, drug efficacy, etc. Applicant has developed methods for extracting geometrical information from 3D volumetric images using a match filter based system to segment a vessel network and extract a mathematical (geometry) vessel representation. Some embodiments of a vessel representation are referred to herein as the Poker Chip representation due to the similarity to a stack of poker chips. The Poker Chip representation treats a vessel as an aggregation of infinitesimal cylinder cross-sections with continuously varying diameters. While in theory the "thickness" of each poker chip is infinitesimal, in practice the thickness of each poker chip may be related to the resolution of the image(s) from which the geometry was extracted. Thus, each poker chip may have associated geometry including, for example, center location, radius and orientation, as discussed in further detail below.

Figure 2:
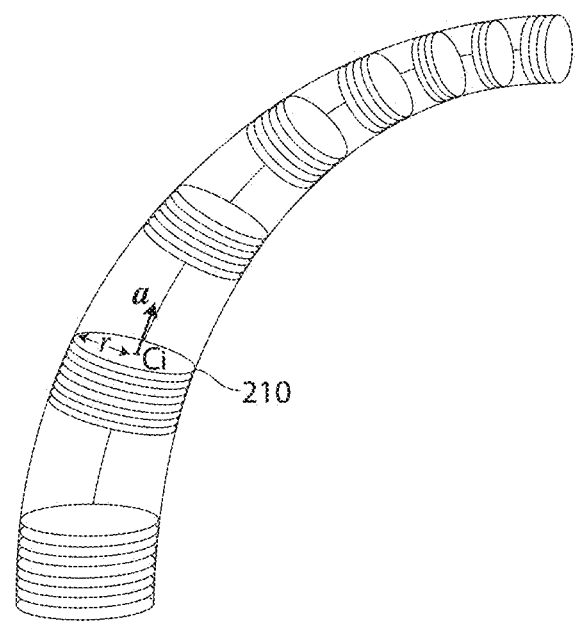
FIG. 2 illustrates a geometrical representation of vessel structure, referred to as the Poker Chip representation, in accordance with some embodiments of the present invention.

FIG. 2 illustrates a schematic of the Poker Chip representation. According to some embodiments, each poker chip 210 is defined by a center location, a radius and an orientation. The center location $c_i$ represents the center of the vessel, for example, determined by centerline filtering, as discussed in further detail below. The radius r represents the radius of the vessel at location $c_i$ and the orientation is the angle of the normal of the poker chip at location $c_i$, and represents the tangent of the centerline of the vessel at location $c_i$. It should be appreciated that the Poker Chip representation may include additional parameters, as the aspects of the invention are not limited in this respect.

Applicant has appreciated that the above Poker Chip representation may be used to determine characteristics of the vasculature that may help in diagnosing disease, providing information on appropriate treatment, and/or assessing the effectiveness of treatment. For example, since the orientation is known at each location, higher level information such as curvature and tortuosity may be computed, as well as vessel density and distribution measures, as discussed in further detail below. Additionally, since vessel diameter may be determined, vessel size and the change in vessel sizes may be computed as well. Various analyses that can be performed using the Poker Chip representation are discussed in further detail below.

To compute some of the higher order information, it may be beneficial to also include in the Poker Chip representation information about neighboring poker chips. For example, information about how the poker chips link together may be valuable in understanding the vessel structure as a whole. As discussed above, Applicant has developed algorithms that facilitate linking poker chips together to provide membership information with respect to which poker chips belong to which vessel and information regarding which poker chips are adjacent to one another. After linking has been achieved, more sophisticated vessel analysis may be performed.

Following below is a more detailed description of algorithms capable of extracting geometry from 3D images to obtain a Poker Chip representation of vasculature present in the images, in accordance with some embodiments of the present invention. While the various algorithms are discussed in connection with detecting and extracting vessel information, the concepts disclosed herein may be applied to detect and associate other structure, as the aspects of the invention are not limited in this respect. In addition, it should be appreciated that distribution analyses according to various aspects of the invention may be applied to information obtained from any vessel image, representation, or combination thereof.

Figure 3A:
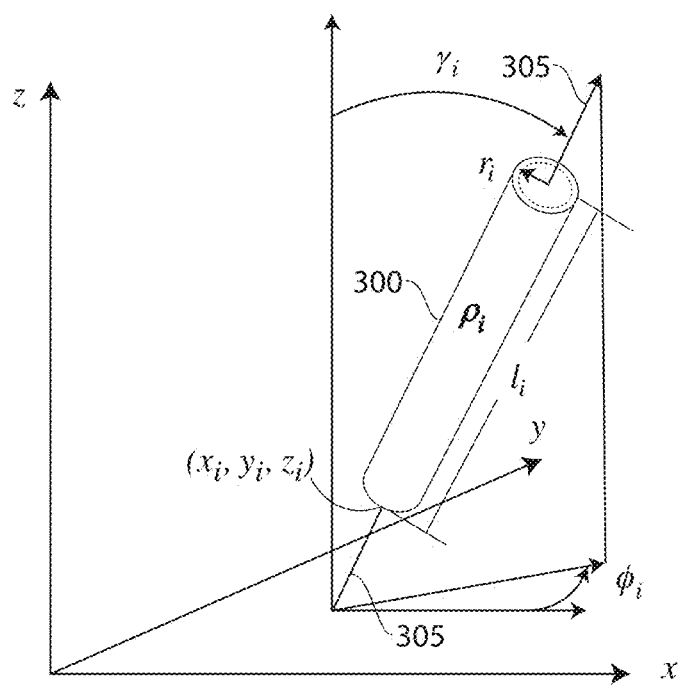
FIG. 3A illustrates a cylindrical segment used to model vessel structure, in accordance with some embodiments of the present invention.

FIG. 3A illustrates one example of a cylindrical segment 300 that may be used to generally model a vessel segment. A configuration of cylindrical segment 300 may be described by a number of parameters in a particular coordinate frame. The position of cylindrical segment 300 may be described by a location of the cylindrical axis 305 at a point $(x_i, y_i, z_i)$ in space, for example, the origin or termination of the cylindrical segment. The orientation of cylindrical segment 300 may be specified by the angle $\phi_i$ from the x-axis and the angle $\gamma_i$ from the y-axis. Since cylindrical segment 300 is axially symmetric, its rotation about the z-axis may not need to be specified. The length of the cylindrical segment may be specified by $l_i$ and the radius of the cylindrical segment 300 may be specified by $r_i$.

Figure 3B:
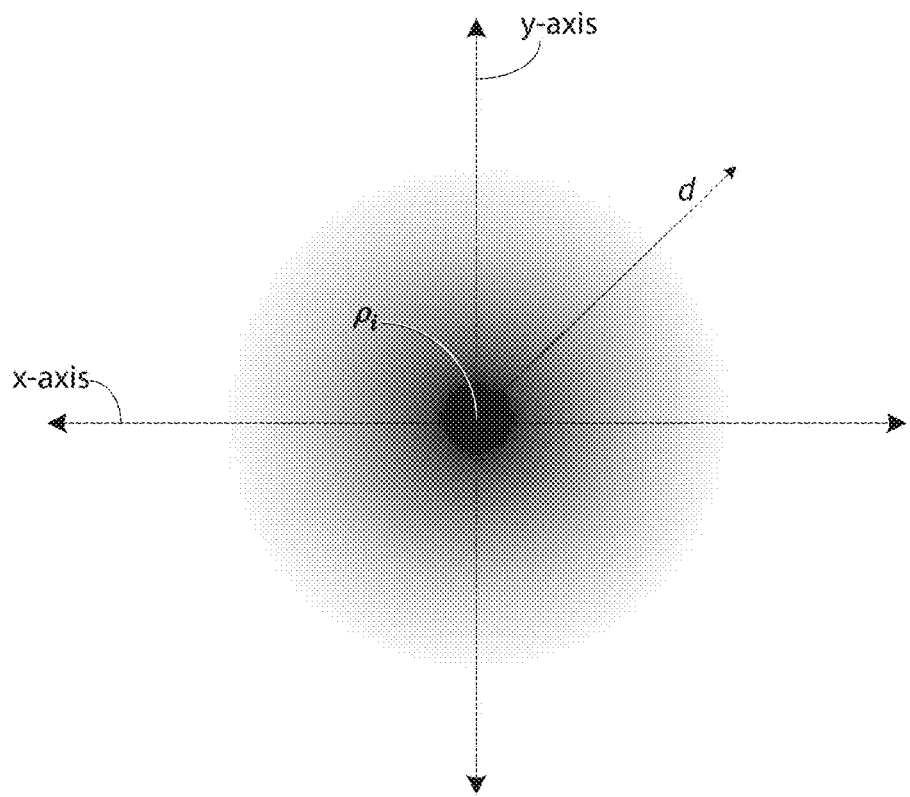
FIG. 3B illustrates a grey scale representation of a characteristic function of a model used to detect vessel structures, in accordance with some embodiments of the present invention.
Figure 3C:
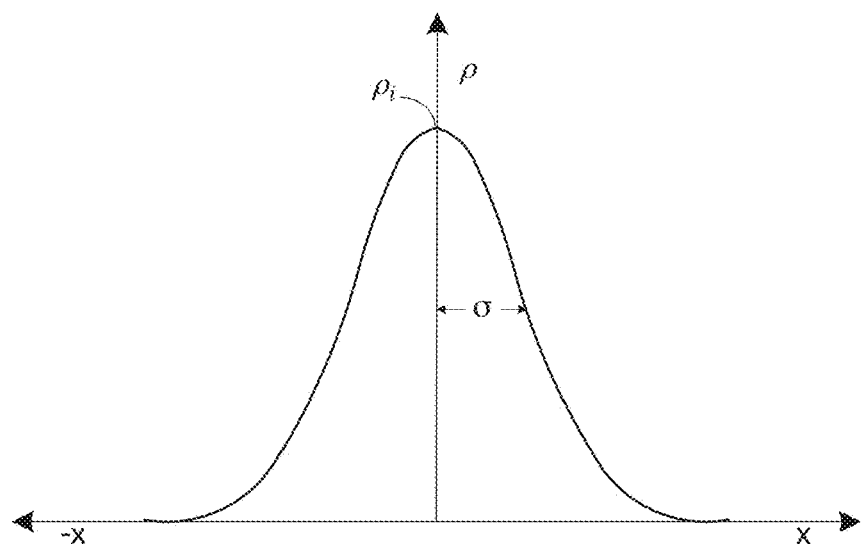
FIG. 3C illustrates a plot of the intensity values along the x-axis at the center of the grey scale Gaussian distribution in FIG. 3B.
Figure 3D:
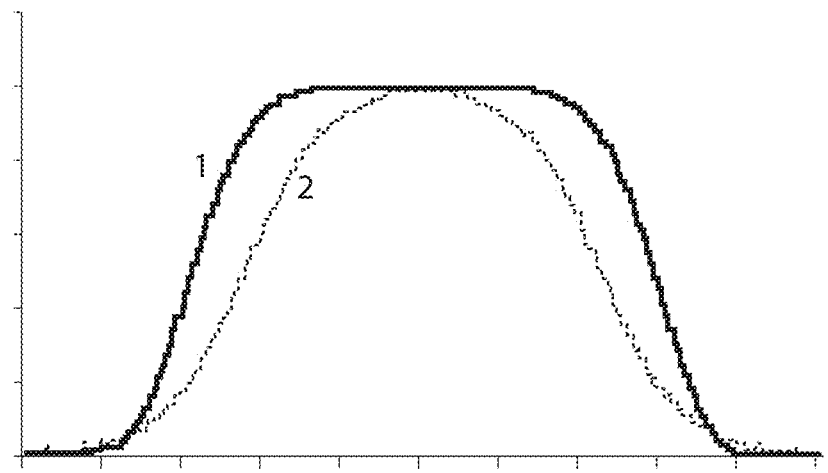
FIG. 3D illustrates a plot of the intensity values along the x-axis of another model of vessel intensity profile.

Applicant has appreciated that the cross-section of a vessel may be characterized by a generally Gaussian shaped intensity distribution. The cross-sectional density of a vessel may be modeled by a Gaussian distribution, centered on the longitudinal axis of the vessel, so that the modeled density is the highest at the center of the vessel. For example, the cross-sectional density distribution of a cylindrical vessel segment, when oriented such that its longitudinal axis coincides with the z-axis, may be modeled as, $$\rho \left( e^{-\frac{1}{r^2}((x-x_i)^2 + (y-y_i)^2)} \right) \quad (1)$$

where $\rho$ is the density coefficient at a center of the cylindrical segment and r is the radius of the cylindrical segment, so that the density is modeled as being greatest at the center (i.e., equal to $\rho$) and decays exponentially as a function of radial distance from the center. FIG. 3B illustrates a grey scale representation of the function given in Eq. (1), where darker grey scale values indicate increased density values. FIG. 3C illustrates a plot of the intensity values along the x-axis at the center of the grey scale Gaussian distribution in FIG. 3B. FIG. 3D illustrates a vessel intensity profile that may better model the intensity profile of vessels in an image. Curve 1 and 2 illustrated vessel profile intensity when vessel diameter is larger than the resolution of the scan and when the vessel diameter is smaller, respectively.

Figure 4:
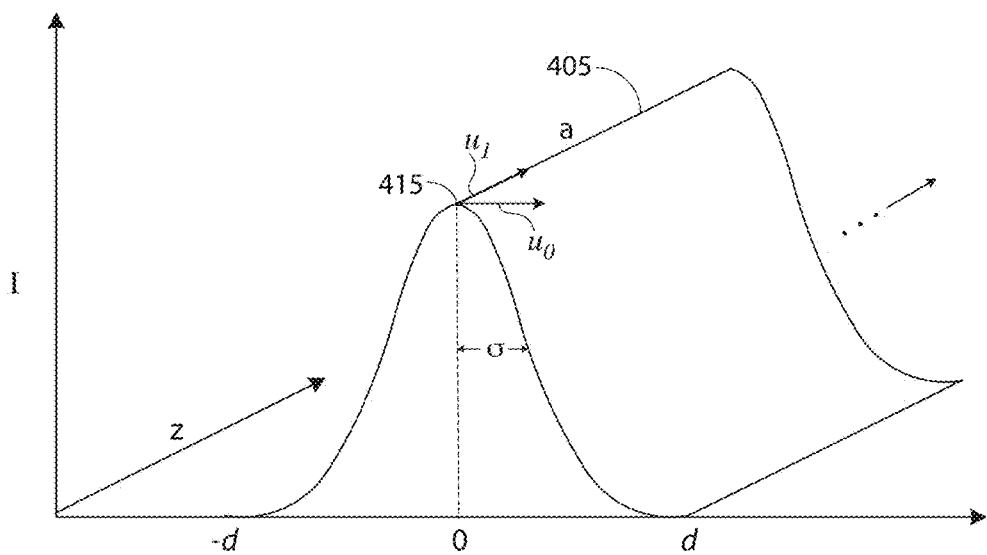
FIG. 4 illustrates schematically a cylindrical vessel segment intensity distribution illustrating a ridge or centerline feature, in accordance with some embodiments of the present invention.

The density distribution along the longitudinal axis of the cylinder (i.e., into and out of the page in FIG. 3B) is substantially uniform and does not vary substantially and may be modeled as a constant function of the cross-sectional distribution along the longitudinal axis, that is, as a constant function of the radial distance d from the center of the distribution. FIG. 4 illustrates schematically a cylindrical vessel segment intensity distribution model. In particular, the model of the cylindrical vessel segment has a maximum density at the center that decays exponentially to the boundary of the vessel as a function of the radial distance d, from the center. At each distance d, the density is uniform along the z-axis. For example, the density at d=0 is the density maximum along the length of the vessel. This density maximum shown by line 405 is referred to as a ridge, and corresponds to the centerline of a vessel.

If the herein described characteristic intensity distribution or similar distribution can be identified in the image, the associated pixels/voxels are likely to belong to a vessel. The characteristic points may be used to facilitate segmenting the image into vessel and non-vessel regions. Some methods of detecting the characteristic shape illustrated in FIG. 4 include performing ridge detection on an image. A ridge point is defined herein as a point in an image wherein the intensity assumes a local extrema in the direction of principal curvature, i.e., the direction having the steepest intensity gradient. For example, at point 415 (and along ridge 405) in FIG. 4, the principal direction of curvature is shown by $u_0$ (i.e., the unit vector (1,0) in the (d, z) coordinate frame). Each point along ridge 405 forms a ridge point since each point is a local maximum along the z-axis. Accordingly, a ridge may be characterized by local derivative information in the image and may be detected by examining the curvature of intensity about points of interest in the image.

Some conventional methods have proposed detecting the ridge using the Hessian operator. However, the Hessian operator requires performing second derivatives of the image information, which reduces the signal-to-noise ratio (SNR) and may result in degraded performance. Applicant has developed methods of detecting the characteristic shape of blood vessels described above using centerline filtering techniques that may avoid some of the performance degradations commonly seen with conventional filters such as the Hessian operator, as discussed in further detail below.

As discussed above in connection with FIG. 1, a non-limiting example of a method for extracting geometry from images may include a number of processing blocks including: a scale detector, an orientation detector, centerline filtering, non-maximum suppression and linkage. Briefly speaking, the system works as follows: firstly, the scale detection and orientation detection modules may be applied on 3D images to obtain correct size and orientation parameters for centerline detection (e.g., scale and orientation parameters for the centerline filters); secondly, based on the parameters obtained from scale detection and orientation detection modules, the centerline filter may be applied on every voxel of a 3D image, or applied on a subsection of voxels for which centerline detection is desired. The generated response field formed by applying the centerline filter indicates the likelihood that the associated voxel corresponds to the vessel centerline; finally, non-maximum suppression and linkage is applied on the centerline response field to extract the vessel centerline and obtain a vessel mathematical representation (e.g., a linked Poker Chip representation). Following below are more detailed descriptions of embodiments of the five main blocks briefly discussed above, e.g., scale detection, orientation detection, centerline filtering, non-maximum suppression and centerline linking.

Scale Detection

As discussed above, scale detection may be applied to estimate the centerline filter size appropriate for each voxel at which centerline detection is to be applied. Applying scale detection on each voxel of a 3D image volume may be relatively expensive computationally. That is, if each voxel in the 3D image is deemed to be a potential centerline point, then scale detection should be applied to each voxel in the image. However, Applicant has appreciated that since vessels occupy only a portion of the volume, it may not be necessary to detect scale on every voxel. In particular, certain voxels may be eliminated based on the image properties of the voxels, for example, the intensity level of the voxel.

In general, intensities from vessels are higher than those in the background. Using a conservative intensity threshold, voxels may be classified as background voxels with a low false positive rate that can be controlled based on how conservative the threshold operator is set. That is, by setting the threshold conservatively, a substantial percentage of the background voxels may be eliminated from scale detection without the risk of eliminating any vessel voxels. The term "background" refers herein to voxels that are not part of the subject matter of interest that is being detected. By eliminating background voxels, the computations needed to perform scale detection can be reduced. That is, by removing at least some voxels from consideration, scale detection need not be performed on each voxel in the image.

Figure 5:
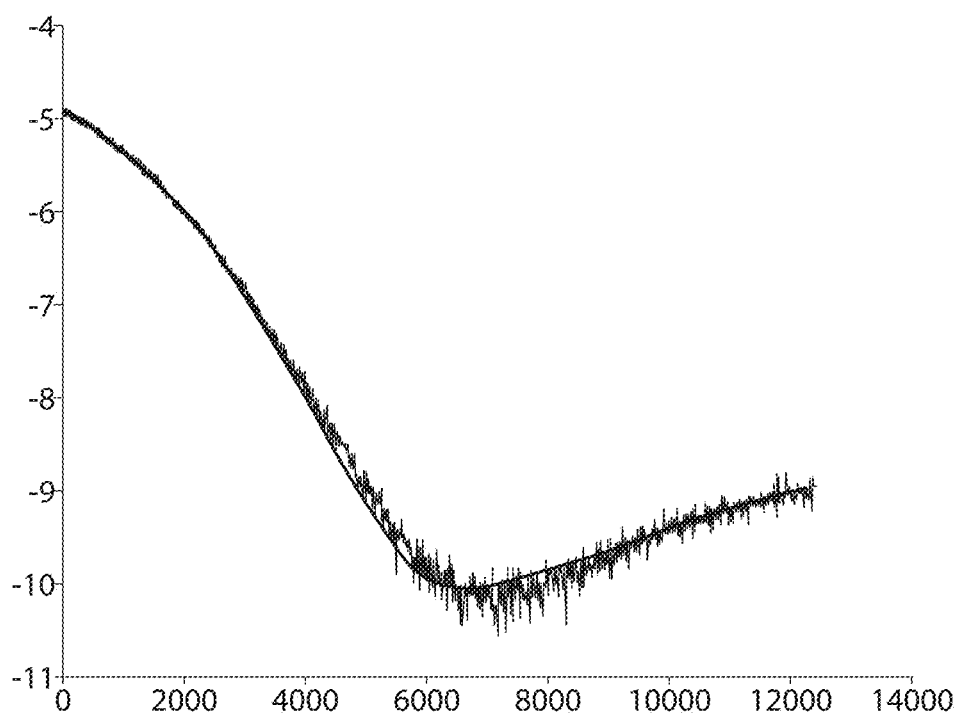
FIG. 5 illustrates an embodiment of a mixture of truncated Gaussian fit to 3D reconstruction intensity data, wherein the vertical axis is in log scale and low part of the horizontal axis is shown.

It is reasonable to model both background intensity and vessel intensities as a Gaussian distribution. In practice, the assumption in FIG. 5 shows that a model using a mixture of truncated Gaussians is a very good fit for the data in low intensity regions. The truncated Gaussian distribution has the Probability Density Function (PDF) as follows:

$$p(I/\mu, \sigma) = \frac{N(I|\mu, \sigma)}{\int_{b_1}^{b_2} N(x|\mu, \sigma)dx} \quad (2)$$

where $N(I|\mu, \sigma)$ denotes a Gaussian distribution with mean $\mu$ and variance $\sigma$, and b1 and b2 are the truncation points. To capture both background and vessel distributions, the mixture of two truncated Gaussians for the data may be expressed as:

$$p(I) = \sum_{c=0}^{1} \sum_{i} \left\{ w_c \log \left[ \frac{N_{c(I_i|\mu_c, \sigma_c)}}{\int_{b_1}^{b_2} N_{c(x_i|\mu_c, \sigma_c)}dx} \right] \right\} \quad (3)$$

where $w_c$ is the weight percentage of each component. Directly maximizing the likelihood may become challenging because determining the marginal probability may require computations that increase exponentially with the data. In some embodiments, the problem is solved using an Expectation Maximization (EM) algorithm. The EM process iteratively goes through two steps by soft assignment of data (Expectation) and maximizing the whole likelihood (Maximization). That is, an initial approximate distribution may be used to classify voxels as either background or foreground (e.g., vessels) in the Expectation step. Next, the distribution is refined based on the classification (Maximization) and classification (Expectation) is repeated on the refined distribution. This process may be repeated until the process converges on a final classification of background and foreground voxels.

Applying an EM algorithm on a mixture of Gaussians is only one method by which background voxels may be eliminated from consideration, or by which voxels are classified as background and foreground voxels. Other preprocessing or thresholding techniques may be used to reduce the number of voxels on which further processing is performed to reduce the computational expense, as the aspects of the invention are not limited in this respect. In addition, while voxel intensity may be one suitable parameter to use to perform a conservative elimination of voxels belonging to the background, any suitable parameter may be used, as the aspects of the invention are not limited in this respect. For example, higher order properties may be used.

As discussed above, separating scale detection and orientation detection may have benefits over algorithms that perform the two operations simultaneously. Applicant has designed a scale detection filter which does not depend on the orientation of the structure to be detected. According to some embodiments, an orientation independent filter may be developed such that the filter can be mathematically described in spherical coordinates as f=f(r), which is a function that does not depend on orientation. The symmetry of the filter allows the filter to be independent of how the filter is oriented. To accurately detect centerline voxels from 3D images, the response generated by the scale detection filter should be maximum when it is located at a centerline voxel. The scale $\sigma_r$ at a point (x, y, z) inside a cylinder may be defined as the distance to the wall of the cylinder boundary:

$$\sigma_r(x,y,z) = \text{dist}(x,y,z; \text{wall of the cyclinder}) \quad (4)$$

Figure 6:
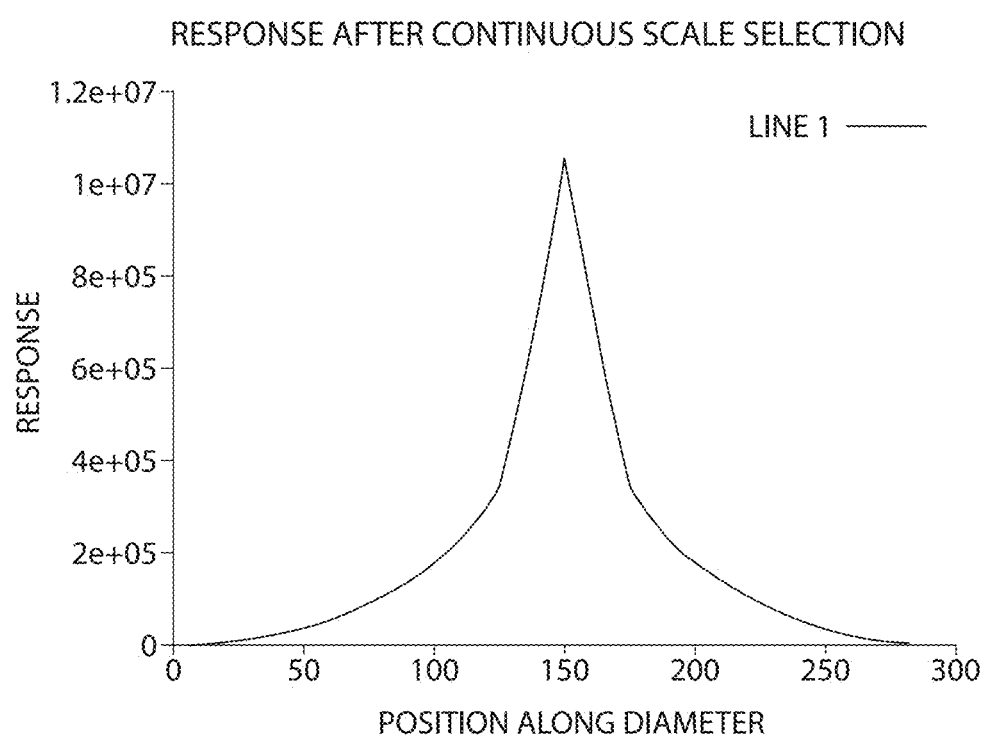
FIG. 6 illustrates an embodiment of a theoretical profile of a centerline filter response using scale detection, in accordance with some embodiments of the present invention.

As shown in FIG. 6, this definition of scale guarantees a unique maximum filter response inside the cylinder after scale selection (in the absence of noise). Normally, the intensity of a 3D image outside of a vessel is significantly lower than the intensity inside the vessel. This rapid intensity decay provides an indication of scale. Applicant has developed a rank-based scale filter that is orientation independent. Given a point X inside a vessel, a rank based scale filter may be defined as:

$$\mathcal{R}(X, r) = \frac{f_-(\{I(X'): |X' - X| = r + 1\})}{\min_r\{f_+(\{I(X'): |X' - X| = 1, \ldots, r\})\}} \quad (5)$$

where R(X, r) is the filter response at image location X with filter radius r, and f– and f+ are rank functions, respectively. Note that the filter is parameterized by radius only, resulting in filter symmetry that is orientation independent. Given various noise models, there are many ways to choose the rank functions. In order to cope with image reconstruction effects, f– may be chosen as the median value of the last 10 lowest intensities and f+ may be chosen as the median value of the last 10 highest intensities. That is, the rank function may be determined from characteristics of the image. However, the rank functions may be selected to be any value that facilitates detection of scale, as the aspects of the invention are not limited in this respect. The scale $\sigma_r(X)$ may then be obtained by finding the minimum radius r so that R(X, r) reaches the threshold α:

$$\sigma_r(X) = \min_r\left\{R(X, r) < \frac{1}{\alpha}\right\} \quad (6)$$

Stated differently, the radius of the scale filter is increased until the filter response no longer satisfies the relationship in Eq. (6). As discussed above, the scale detection filter may be designed to be independent of orientation. According to some embodiments, the kernel or shell of the scale filter is a circle in 2D and a sphere in 3D. As a result, the size of the filter is defined by the radius r, where the center of the filter is located at a target voxel at location X in the image. Since the filter has the same radius in all directions, the application of the scale filter is independent of orientation.

Figure 7:
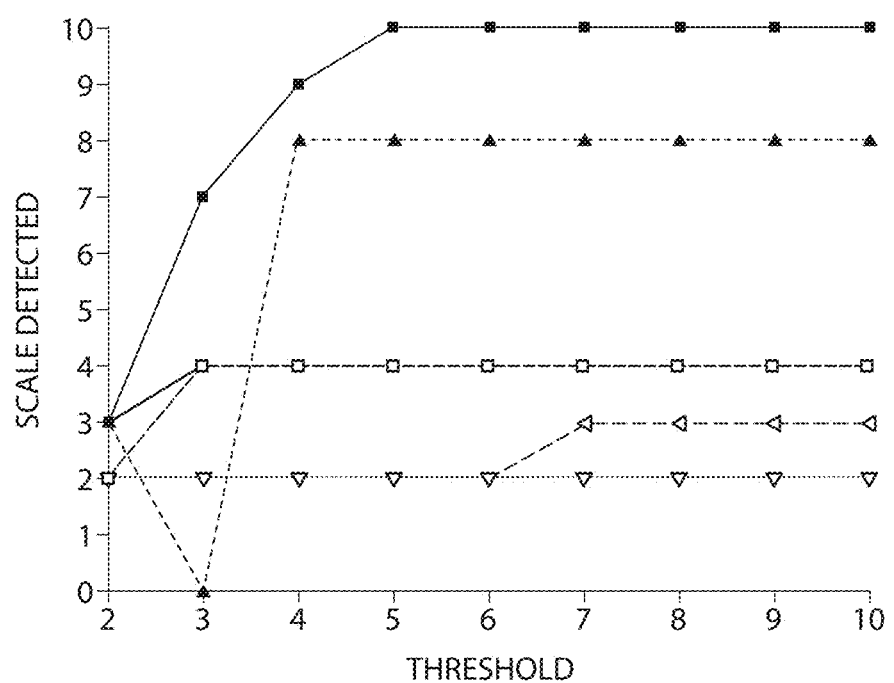
FIG. 7 illustrates an embodiment of a detected scale versus the choice of threshold α.

The criteria for the filter response may be chosen to be any suitable criteria that can robustly determine when the filter kernel has crossed a vessel boundary. The criteria in Eq. (6) is merely exemplary. In some embodiments, the value of a is chosen to be 5. However, other values may be used as well as the aspects of the invention are not limited in this respect. In order to examine the sensitivities of this rank-based scale filter to the choice of the threshold parameter α, a few points inside different vessels may be randomly chosen to see how the selected scale changes depending on the ratio threshold parameter α. FIG. 7 shows that the scale approaches the correct value when a is chosen to be larger than 5.

Figure 8:
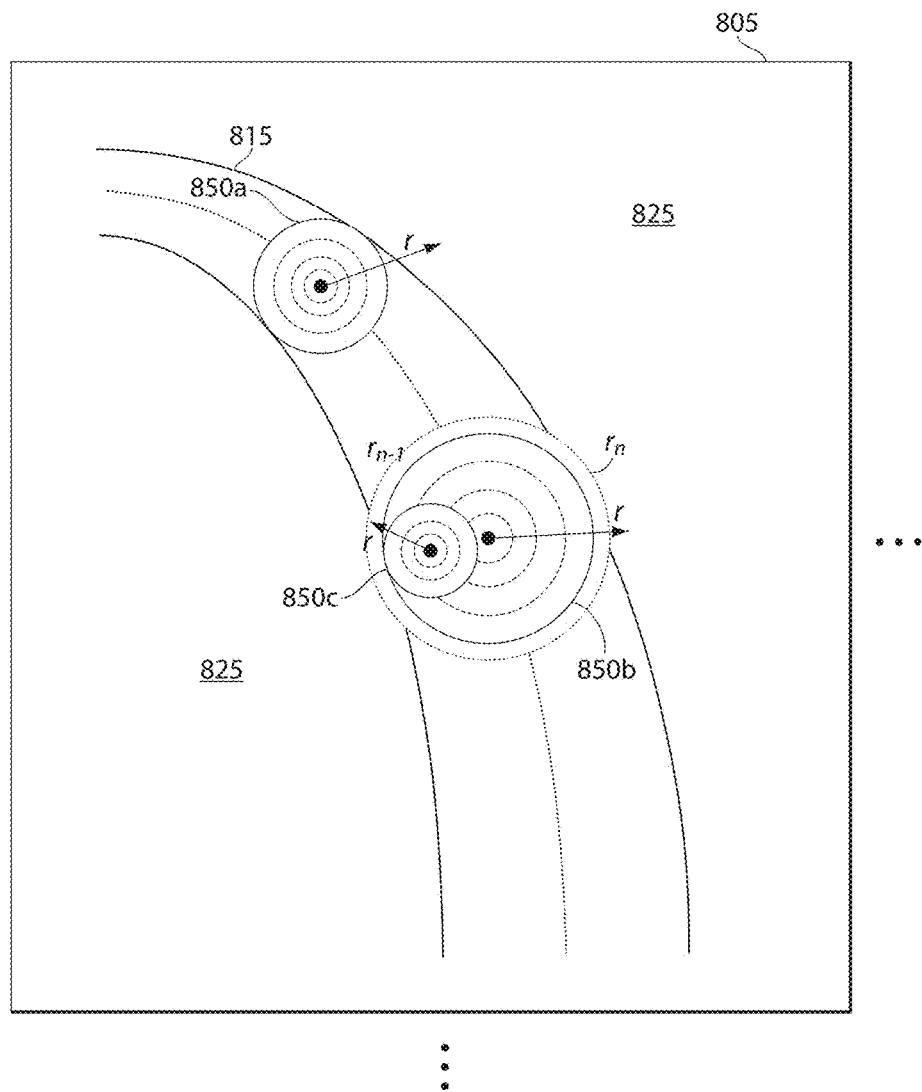
FIG. 8 illustrates pictorial an orientation independent scale filter, in accordance with some embodiments of the present invention.

FIG. 8 illustrates pictorial an orientation independent scale filter, in accordance with some embodiments of the present invention. It should be appreciated that while the scale detection filter in FIG. 8 is shown (and is suitable) in the context of a 2D image for convenience of illustration, the scale detection filter is designed as a 3D filter to detect scale in 3D volumetric images. In particular, the circular filter illustrated in FIG. 8 may be made an expanded to a sphere to detect scale in 3D. In FIG. 8, a portion of an image 805 is shown having a vessel structure 815 within the image portion. It should be appreciated that image portion 805 is schematic and the vessel structure 815 and the background 825 would be comprised of an intensity value at each voxel location in the image portion. Moreover, it should be appreciated that image portion 805 may be a small portion of a much larger image. For the sake of clarity only a single vessel structure is depicted in image portion 805, though the image portion may in reality include any number of vessel structures.

FIG. 8 also illustrates three separate applications of an orientation independent scale filter 850. It should be appreciated that the scale filter 850 may be applied at all of the image voxels or at a selected number of image voxels (e.g., voxels determined to be vessel voxels using a preprocessing techniques such as the intelligent thresholding method described above). The three applications of the filter in FIG. 8 are merely exemplary and are chosen at arbitrary locations to assist in describing the scale detection filter. Each application of the filter begins by placing the filter with a predetermined minimum radius r on a target pixel at which scale is being detected. The scale filter is then applied to the image, for example, by convolving the image pixels that fall under the filter kernel or support with the values of the filter kernel. If a certain criteria is met, the filter is assumed to still be entirely within the vessel and the radius r is increased.

In FIG. 8, the increasing of the filter radius is depicted by the successively larger circles in dashed line. The circles in solid line denote the last filter applied such that the criteria was met. For example, the dotted line circle in filter application 850b shows a circle of $r_n$ that when applied to the underlying image failed to meet the criteria, where n is the number of successively larger radius filter kernels that have been applied to the image. Thus, the scale at the corresponding image location is determined to be $r_{n-1}$. Not only does scale detection provide the appropriate scale to be used in subsequent filtering processes (e.g., centerline detection), it also may indicate the radius of the vessel structure in the Poker Chip representation.

Applicant has used the fact that the intensity of voxels within the vessel, in the absence of noise, is substantially higher than the background voxels to establish the criteria such that the criteria will not generally be met when the filter kernel is extended outside the vessel structure. One embodiment of such a criteria is described in Eq. 5 and Eq. 6. By employing the rank functions illustrated in Eq. 5, and using the criteria in Eq. 6, a robust filter may be designed that will fail to meet the criteria when the filter kernel is increased in size such that it encompasses voxels outside of the vessel. However, the above described scale detection filter is exemplary and other scale detection filters may be used, as the aspects of the invention are not limited in this respect. In addition, any criteria that tends not to be met as a filter is expanded across a vessel boundary may be used, as the aspects of the invention are not limited in this respect.

Because the centerline voxels are not known a priori, the scale detection filter may be applied to non-centerline voxels. As shown by filter application 850b, the scale detection is again stopped when the filter kernel crosses the vessel boundary. Because the target voxel is not a centerline voxel, the radius of the filter will not correspond to the radius of the vessel. However, this may be inconsequential because voxels that are not determined to be centerline voxels are removed in subsequent processing, such as during centerline filtering discussed below. Because only voxels detected as centerline voxels will survive centerline filtering, the radius of the scale detector may accurately reflect the radius of the associated vessel.

Figure 9:
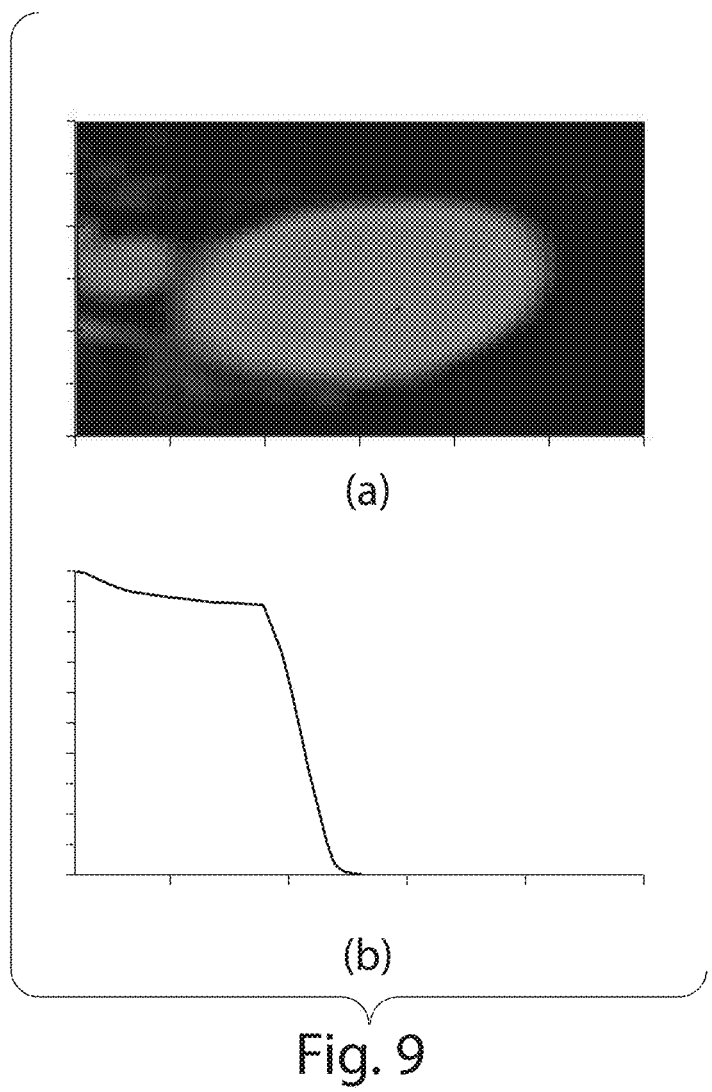
FIG. 9 illustrates an embodiment of how R(X, r) behaviors on real images—(a) a slice of 3D images is shown and blue point is the point X where we apply rank-based scale filter—(b) the rank-based scale filter's response with different radius is shown—although the intensities have large variation inside vessel, the rank-based scale filter behavior smoothly and have a rapidly decay while cross the boundary of the vessel.

FIG. 9 shows what R(X, r) looks like when it is applied on real images. Although the intensities have large variation inside the vessel, the rank-based scale filter behaves smoothly and decays relatively rapidly across the boundary of the vessel. Thus, rank-based scale filters may have the generally beneficial property of relatively distinct response change as the filter crosses vessel boundaries, and is relatively stable and insensitive to the choice of ratio parameter. Accordingly, scale may be detected at each selected voxel in the image. For example, scale may be detected at each voxel in the image or the reduced number of voxels resulting from performing thresholding on the image to eliminate at least some of the background voxels. The selected voxels at which scale detection is performed can be selected in other ways, as the aspects of the invention are not limited in this respect.

Orientation Detection

As discussed above, centerline filtering may be improved by first determining the orientation at which the centerline filter should be applied. Since scale is detected independent of orientation, orientation detection may be performed separately from scale detection and, in some embodiments, orientation detection uses the scale values detected during scale detection to improve detection of the orientation of the subject matter of interest. In some embodiments, a gradient based orientation detection algorithm may be used, however, other algorithms may be used to detect vessel orientation, as the aspects of the invention are not limited in this respect. Because of the rotational symmetry along the axis of a cylinder on which the vessel structure may be modeled, the intensity along a line parallel to the vessel axis is constant in the absence of noise. In other words, the directional derivative of intensity along the direction v parallel to the vessel axis is zero in the absence of noise:

$$v \cdot \nabla \rho(X) = 0 \qquad (7)$$

It should be appreciated that x-ray decay during image acquisition depends on its penetrating length. Thus, the intensity inside a vessel tends to vary along any direction other than the axis direction. This fact indicates that Eq. (7) may be a necessary and sufficient condition for finding the vessel direction since the above argument holds for any point X inside the vessel. Therefore, the direction of a small cylinder segment at each point X can be estimated by finding a direction vector a along which the intensities have the least change. However, direct estimation from the derivative of one point X tends to be error prone. In some embodiments, all the derivatives inside a small volume centering on the point X may be used to increase the accuracy. To be more precise, the axis direction â may be estimated by finding a direction a that minimizes the sum of the directional intensity gradient along this direction:

$$\hat{a} = \operatorname*{argmin}_{a} \left\{ \int\int\int_{v} \|a \cdot \nabla \rho(x, y, z)\| dxdydz \right\} \qquad (8)$$

where σ(X) is the scale detected at point X and ∥·∥ is the norm discussed herein. In the presence of noise, a directional gradient of intensity convolved with an adaptive Gaussian kernel may be used, as follows.

$$\hat{a} = \operatorname*{argmin}_{a} \left\{ \int\int\int_{v} \|a \cdot \nabla (G_{\sigma(x,y,z)} \circ \rho(x, y, z))\| dxdydz \right\} \qquad (9)$$

In some embodiments, Eq. (9) can be solved by a least square estimation by assuming the noise distribution is Gaussian i.i.d, i.e., the norm in Eq. (9) is an L2-norm. However, it is well known that an L2-norm may be sensitive to outliers present in the input data, and outliers may frequently appear in reconstructed 3D images. In some embodiments, a L1-norm in Eq. (9) may be used.

$$\hat{a} = \operatorname*{argmin}_{a} \left\{ \int\int\int_{v} \|a \cdot \nabla (G_{\sigma(x,y,z)} \circ \rho(x, y, z))\|_1 dxdydz \right\} \qquad (10)$$

$$\operatorname*{argmin}_{a} \left\{ \int\int\int_{v} \|a\|_1 \cdot \|\nabla (G_{\sigma(x,y,z)} \circ \rho(x, y, z))\|_1 dxdydz \right\} \qquad (11)$$

To avoid the trivial solution at a=0 in the above equation, the constraint $\Sigma_i \|a_i\|_2 = 1$ may be used. Since a is independent of the point (x, y, z), a is moved out of the triple integral so that:

$$\hat{a} = \min_{a} \left\{ \left\| a \cdot \frac{\int\int\int_{v} \nabla (G_{\sigma(x,y,z)} \circ \rho(x, y, z)) dxdydz}{M} \right\|_{L2} \right\} \qquad (12)$$

$$\text{s.t.} \left\{ \sum_{i} \|a_i\|_2 = 1 \right\}$$

It should be appreciated that in Eqs. (8)-(12), the operation is being performed over a volume v. By performing orientation detection over a neighborhood, rather than at a single voxel, semi-global information may be captured in the orientation assessment. The neighborhood information allows for robust orientation detection in the presence of noise and outliers. However, it should be appreciated that the neighborhood (e.g., the volume v) may be different for detecting direction in relatively large vessels versus relatively small vessels. Accordingly, Applicant has developed an adaptive method that varies the size of the neighborhood based on the scale at a target voxel. That is, the scale determined during scale detection may be used to determine the size of the volume v. In some embodiments, the size of $(2\lfloor s+2 \rfloor + 1)$ may be used as the size of volume. However, any adaptive neighborhood based on scale may be used, as the aspects of the invention are not limited in this respect. Thus, the size of the neighborhood used for orientation detection may be adapted according to the scale of the image at each location.

As discussed above, and L1-norm may be used to address outliers. There are a number of ways to solve Eq. (12). In some embodiments, the equation is solved by constraint optimization using Lagrange multipliers. Applying Lagrange multipliers to the above equation obtains:

$$\nabla_a(a^T M^T M a + \lambda a^T a) = 0$$

$$(M^T M)a + \lambda a^T = 0 \tag{13}$$

Therefore the center line direction, a, may be obtained by computing the eigenvector associated with the smallest eigenvalues of matrix M. Referring back to FIG. 4, solving the above equations to determine the direction a can be pictorial explained. In general terms, the eigenvectors of matrix M indicate the characteristic directions of curvature. The relationship between these characteristic directions of curvature may be employed to identify the direction of the centerline. The eigenvalues and associated eigenvectors of a matrix may be determined in various ways, for example, by any number of well known iterative methods of diagonalizing a matrix or analytically by directly solving the relationship:

$$Mu = \lambda u \tag{14}$$

where M is the matrix of Eq. 13, u is an eigenvector of matrix M, and $\lambda$ is an eigenvalue associated with u. The magnitude of each eigenvalue of the matrix M is related to the "significance" of the associated eigenvector. Stated differently, the eigenvalue indicates how much the curvature along the associated eigenvector contributes to the local curvature determined by the matrix M. Accordingly, a in Eq. 13 is the eigenvector associated with the smallest eigenvalue and indicates the direction in which the change in intensity is the smallest. The largest eigenvalue of the matrix M is associated with the principal direction of curvature.

In FIG. 4, the linearly independent eigenvectors $u_0$ and $u_1$ (i.e., eigenvectors $u_0$ and $u_1$ are orthogonal) are shown on the illustrated intensity curve. The eigenvalue $\lambda_0$ herein denotes the eigenvalue having the greatest absolute value and is referred to as the principal eigenvalue. Accordingly, the associated eigenvector $u_0$ indicates the principal direction of curvature at a target pixel and $\lambda_0$ is related to the magnitude of the curvature. The eigenvalue $\lambda_1$ (referred to as the secondary eigenvalue) is related to the magnitude of curvature in the direction of $u_1$, i.e., in a direction orthogonal to the principal direction of curvature indicated by $u_0$. Along the ridge of the Gaussian profile (i.e., in the direction $u_1$), the intensity should be substantially zero and the change in intensity relatively small and in the noiseless case is zero (i.e., the intensity does not change as a function of z in the direction of the centerline). Accordingly, by determining the eigenvector associated with the smallest eigenvalue, the direction a which corresponds to the direction of the centerline may be determined. Thus, the orientation of the centerline may be determined at each of the selected voxels.

Centerline Detection

Having determined scale and orientation for the feature detection filter, the feature of interest may be detected. According to some embodiments, centerline detection is performed using a Gaussian centerline filter. For example, assume the density inside the vessel satisfies the Gaussian model:

$$I(r) = I_0 e^{-\frac{r^2}{2\sigma^2}} \tag{15}$$

Here, r is in the direction perpendicular to the vessel axis; $\sigma$ is the radius of the vessel; and $I_0$ is the intensity at the center. In order to detect a Gaussian vessel, a filter with radial variation corresponding to the 2nd derivative of the Gaussian may be used:

$$h(r) = \left(\frac{r^2}{\sigma^2} - 1\right)e^{-\frac{r^2}{\sigma^2}} \tag{16}$$

The application of this filter corresponds to a volume integral over space. This volume integral should vanish if the filter is embedded in material with constant density. However the 2nd derivative of the Gaussian does not, i.e., $$\int_0^\infty \left(\frac{r^2}{\sigma^2} - 1\right)e^{-\frac{r^2}{\sigma^2}} r \, dr = 1 \tag{17}$$

This problem can be fixed by adding an offset, $$\int_0^\infty \left(\frac{r^2}{\sigma^2} - 2\right)e^{-\frac{r^2}{\sigma^2}} r \, dr = 0 \tag{18}$$

Therefore, the centerline filter has the form $$f(r) = \frac{e}{4\Pi\sigma^2}\left[2 - \left[\frac{r}{\sigma}\right]^2\right]e^{-\frac{r^2}{2\sigma^2}} \tag{19}$$

This filter has a positive core when $r < \sqrt{2}\sigma <$ and negative shell when $r > \sqrt{2}\sigma$.

Applicant has appreciated that in the presence of noise, a centerline filter that closely mimics the shape of a Gaussian as described above may at times be inaccurate, especially in situations where vessel structures are relatively close together. In particular, the continuous decay of the Gaussian may incorrectly detect or fail to detect centerline voxels in certain situations, such as when vessel structures are close together and/or in circumstances where relatively small vessel structures appear nearby relatively large vessel structures.

Figure 10A:
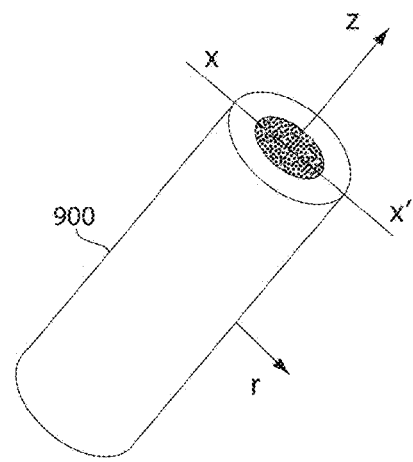
FIG. 10A illustrates a centerline filter, in accordance with some embodiments of the present invention.

Applicant has appreciated that a modified centerline filter may be more effective at accurately identifying centerline points, particularly in the presence of noise. According to some embodiments, centerline detection is performed using a filter that better matches the profile of vessel structures in an image. FIG. 10A illustrates a matched filter in accordance with some embodiments of the present invention. Filter 900 includes an inner core and an outer core. Rather than a Gaussian kernel, filter 900 includes a step function between the inner and outer core. As a result, the filter support is more compact and the filter is able to more accurately detect vessel structures that are close together. In addition, because the filter better matches vessel profiles, centerline detection may be more accurate. An example of values assigned to the matched filter 900 according to some embodiments include:

$$f_s(r, z) = \begin{cases} 1 & r \leq s \text{ and } z \leq \sqrt{2}\,s \\ 0 & s < r \leq \sqrt{2}\,s \text{ and } z \leq \sqrt{2}\,s \\ -1 & r > \sqrt{2}\,s \text{ or } z > \sqrt{2}\,s \end{cases} \quad (20)$$

Figure 10B:
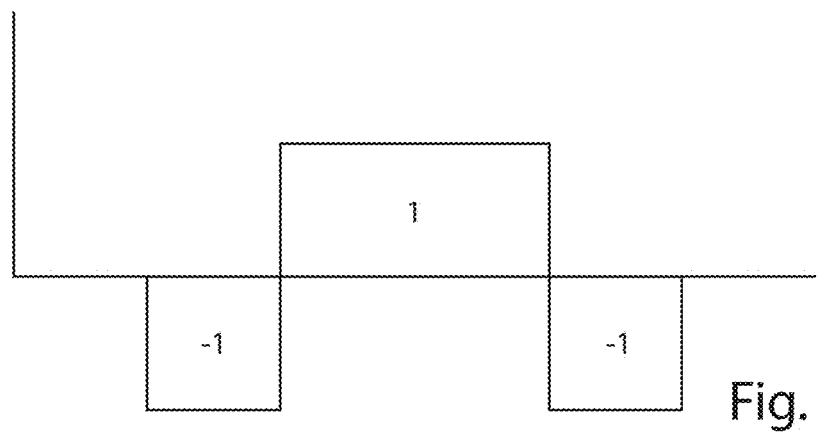
FIG. 10B illustrates a profile of the centerline filter illustrated in FIG. 9A along the line x-x', in accordance with some embodiments of the present invention.
Figure 12:
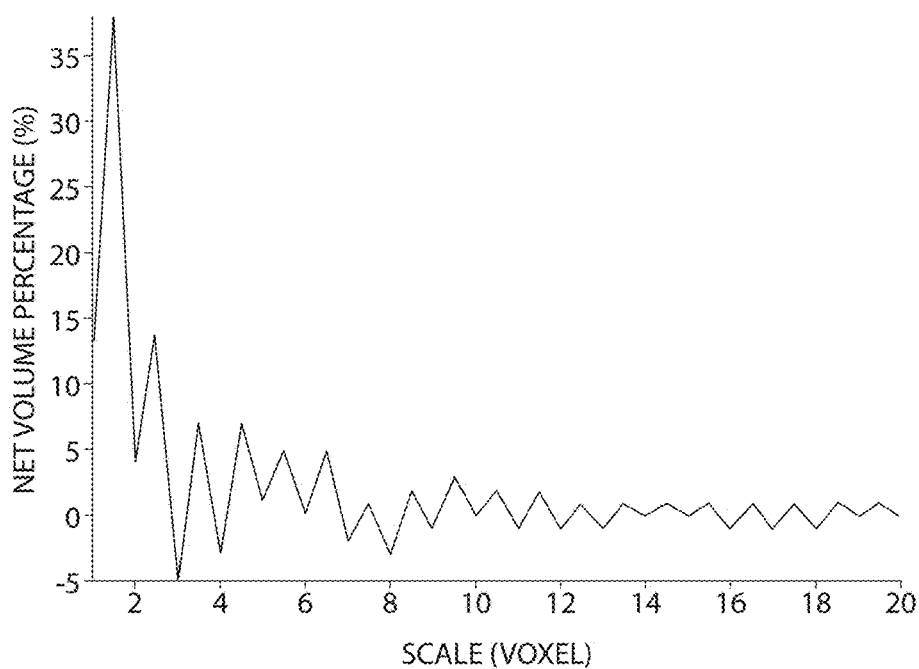
FIG. 12 illustrates net volume of the center line filter versus different scales.

An illustration of the profile of the above filter along the axis x-x' is shown pictorially in FIG. 10B. As shown, the size of the matched filter is based on the scale s detected during scale detection. Applying this filter, the centerline response may be given as:

$$r(x,y,z) = \iiint T[f(r,z)G(0,\sigma)]I(x,y,z)dxdydz \quad (21)$$

where G(0, σ) is a Gaussian smooth kernel. When the scale of the filter is small (e.g., when scale detection determines that the local scale is relatively small), the filter defined by Eq. (20) may not have a zero net volume (volume of the positive core minus the volume of the negative core). This may cause detection difficulties because the filter may have non-zero response when applied to a non-zero uniform background. As shown in the FIG. 12, when the scale of the filter is small, the net volume percentage may be quite large. For example, for a centerline filter with scale of 1.5, the net volume is 35% of the total volume of the filter. Thus, the filter may generate filter bias in the favor of small scale.

Therefore, to address this bias the filter described above may be modified as:

$$f_s(r, z) = \begin{cases} 1 & r \leq s \text{ and } z \leq \sqrt{2}\,s \\ 0 & s < r \leq \sigma(s) \text{ and } z \leq \sqrt{2}\,\sigma(s) \\ -w_s & r > \sigma(s) \text{ or } z > \sqrt{2}\,\sigma(s) \end{cases} \quad (22)$$

where, $$\sigma(s) = \begin{cases} \sqrt{2}\,s + 0.5 & \text{if } s < 10 \\ \sqrt{2}\,s & \text{otherwise} \end{cases} \quad (23)$$

and $w_s$ is a function of scale s so that, $$\iiint_{r>\sigma(s) \text{ or } z>\sqrt{2}\sigma(s)} w_s dxdydz = \iiint_{r\leq a \text{ and } z\leq\sqrt{2}s} dxdydz \quad (24)$$

Figure 10C:
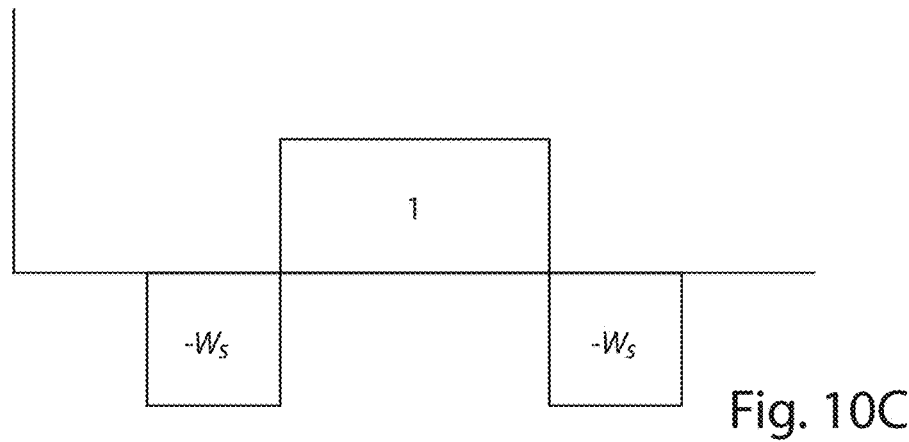
FIG. 10C illustrates another profile of the centerline filter illustrated in FIG. 9A along the line x-x', in accordance with some embodiments of the present invention.
Figure 11:
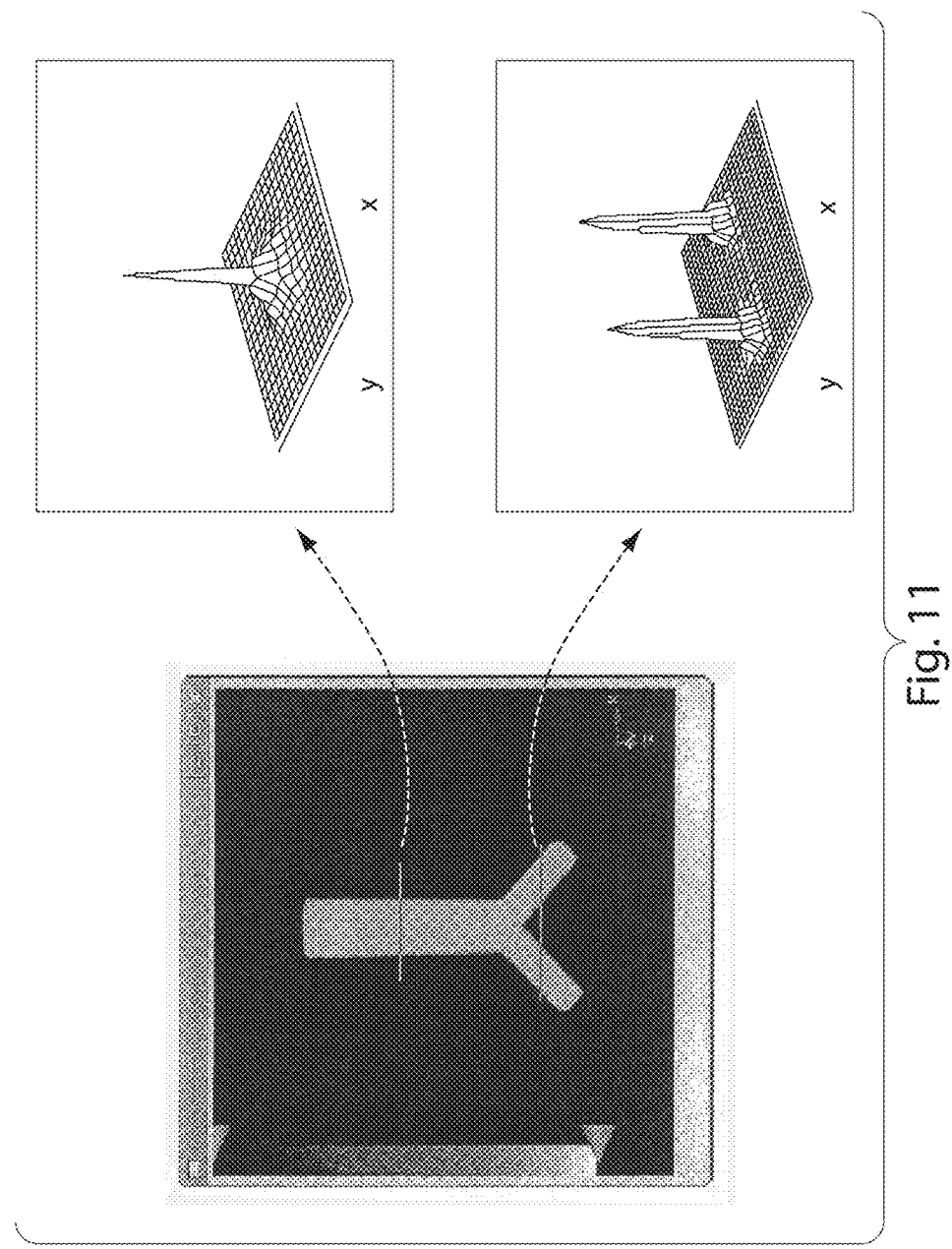
FIG. 11 illustrates centerline filtering on a 3D volume data set, in accordance with some embodiments of the present invention.

An illustration of the profile of the filter expressed in Eq. (22) along the axis x-x' is shown pictorially in FIG. 10C. The matched filters described above may be particularly effective at accurately detecting centerline voxels in the presence of noise and in circumstances when subject matter of interest is positioned in close proximity to each other.

The matched filters described above may be applied to a plurality of selected voxels in the image. Accordingly, for each selected voxel at which the matched filter is applied, there will be an associated filter response indicative of the likelihood that the corresponding voxel is a centerline voxel. However, only the maximum filter responses may be of interest. That is, the maximum filter responses are those that are most likely to be centerline voxels. Accordingly, filter responses that are not maximum may be suppressed such that only those voxels having maximum filter responses remain.

Non Maximum Suppression

In some embodiments, non-maximum suppression may be performed. For example, after centerline filtering, each voxel has a response. The response on each voxel indicates how likely it is that the voxel is a centerline voxel. Since the center line voxel should have the maximum response in the plane perpendicular to the axis, the purpose of non-maximum suppression is to suppress non-maximum responses to eliminate non-centerline voxels. On each voxel, a cutting plane perpendicular to the vessel axis may be used to suppress the non-maximum responses. On the cutting plane, only local maximums of centerline filter responses are kept and all other responses are suppressed. Interpolating the centerline location in order to achieve sub-voxel accuracy is described below.

In some embodiments, location interpolation on the cutting plane may be performed. After obtaining the direction of the cylinder, a cutting plane perpendicular to this direction may be used to apply the non-maximum suppression as an analog to the traditional computer vision edge detection problem. Given an arbitrary voxel x, the voxel x may be tested to determine whether the voxel is a local maxima. According to some embodiments, the cutting plane may be centered on x and the centerline response R(x) may be compared with any other responses in its cutting plane neighborhood N(x, $v_x$). That is, the response field in the neighborhood N (e.g., a 3×3×3 neighborhood) may be projected onto this cutting plane. If the response at voxel x is larger or equal to all of the responses of neighborhood voxel, voxel x may be labeled as a local maxima. Otherwise, voxel x is labeled as a non-maxima voxel and suppressed. This test may be expressed as:

$$IsMaxima(x) = \begin{cases} \text{true} & R(x) \geq R(y), \forall y \in \mathcal{N}(x, v_x) \\ \text{false} & \text{otherwise} \end{cases} \quad (25)$$

where N(x, vx) denotes the cutting plane neighborhood of the point x. Once the neighborhood is determined, the parabolic function as shown below may be used to interpolate the sub-voxel maximum location.

$$r(x,y) = ax^2 + by^2 + cxy + dx + ey + f \quad (26)$$

Given the above response model and the centerline filter responses in a small region around the center, the following equations may be used:

$$an^2 + bm^2 + cmn + dn + em + f = r(n, m) \quad (27)$$
$$a(n-1)^2 + bm^2 + cm(n-1) + d(n-1) + em + f = r(n-1, m)$$
$$\vdots \qquad \vdots$$
$$a(n-1)^2 + bm^2 + cm(n-1) - d(n-1) - em + f = r(1-n, -m)$$
$$an^2 + bm^2 + cmn - dn - em + f = r(-n, -m)$$

This linear form can be written as a matrix form $$A \begin{bmatrix} a \\ b \\ c \\ d \\ e \\ f \end{bmatrix} = \begin{bmatrix} r(n, m) \\ r(n-1, m) \\ \vdots \\ r(1-n, -m) \\ r(-n, -m) \end{bmatrix} \quad (28)$$

$$\text{where } A = \begin{bmatrix} n^2 & m^2 & mn & n & m & 1 \\ (n-1)^2 & m & m(n-1) & n-1 & m & 1 \\ \vdots & \vdots & \vdots & \vdots & \vdots & \vdots \\ n^2 & m^2 & m(n-1) & 1-n & -m & 1 \\ n^2 & m^2 & mn & -n & -m & 1 \end{bmatrix} \quad (29)$$

The maximum location is determined by the stationary condition $$\frac{\partial r}{\partial x} = \frac{\partial r}{\partial y} = 0.$$

That is, $$2ax+cy\_d=0$$

$$cx+2by+e=0 \quad (30)$$

Therefore, $$\begin{bmatrix} x \\ y \end{bmatrix} = -\begin{bmatrix} 2a & c \\ c & 2b \end{bmatrix}^{-1} \begin{bmatrix} d \\ e \end{bmatrix} \quad (31)$$

$$= \frac{1}{4ab-c^2}\begin{bmatrix} -2b & c \\ c & -2a \end{bmatrix}\begin{bmatrix} d \\ e \end{bmatrix}$$

$$= \begin{bmatrix} \frac{ce-2bd}{4ab-c^2} \\ \frac{cd-2ae}{4ab-c^2} \end{bmatrix}$$

In some embodiments, the size of the neighborhood $N(x, v_x)$ is determined based characteristics of the image in the neighborhood. There is a natural question of how big the neighborhood size should be chosen in the non-maximum suppression algorithm. In some embodiments, the smallest size of 3×3×3 may be used, but this choice may cause outliers to survive non-maximal suppression in noisy regions. An alternative method of choosing the parameter is to use the results from radius and/or scale detection. In some embodiments, to avoid suppressing real vessels which are close to each other, a conservative approach may be used when choosing the neighborhood:

$$n = 2\left\lfloor \frac{s}{\sqrt{2}} \right\rfloor = 1 \quad (32)$$

It should be appreciated that the neighborhood in Eq. (32) is exemplary and an adaptive neighborhood, for example, based on scale may be determined in other ways, as the aspects of the invention are not limited in this respect.

Linking

As discussed above, the output from centerline filtering and non-maximum suppression processes provides a 3D field in which each point is marked as either belonging to or not belonging to a centerline. In some embodiments, centerline points can be associated with other information such as radius, strength and orientation of the cylinder element (e.g., using the Poker Chip representation). The task of cylinder element linking may include connecting centerline points and identifying the junctions to generate a vessel network. In some embodiments, practical difficulties may arise associated with one or more of the following: 1) small pieces of centerline may be missing; 2) due to digitization, the centerline segments after non-maximum suppression form "zig-zags." 3) small outlier centerline segments may appear to be present due to noise where there is no real centerline; and 4) junction region may confuse the linking algorithm and lead to wrong linkages. Applicant has developed a linking method that addresses one or more of these difficulties.

In some embodiments, a local cylinder element linking algorithm may be used as follows: 1) start with a most prominent cylinder segment; 2) search in front of the cylinder segment until no more directly connected successors exist; 3) search behind the cylinder segment until no more predecessors exist; 4) mark all the connected cylinder elements; and 5) repeat the above steps until no more cylinder segments are left unmarked. An example of a linking method according to some embodiments, is described in further detail below.

A single branch of a vessel may be modeled as a digitization of a smooth, 3D curve which connects all the poker chips that belong to this branch. Given a point y that has already been selected as part of a branch (e.g., a centerline point with a large response), point y is linked to a nearby point based on a given criteria. For example, linking may be selected to prefer connecting to a point which is close to point y (distance), that does not require a large change in the expected direction $v_y$ (direction), and that has a response that is as similar to the response at point y as possible (response). Each candidate point x may be subjected to this criteria to determine which candidate is the most likely link.

According to some embodiments, the criteria is determined using a probabilistic model. For example, the above tests may be performed by finding the point x which maximizes the posterior possibility, $$Pr(L_y=x|x,v_x,r_x) \quad (33)$$

Without knowing the prior information, maximizing the posterior probability is the same as maximizing the likelihood, $$Pr(x,v_x,r_x|L=x) \quad (34)$$

If the tests of the distance, direction and response are conditional independent given $L_y=x$, it may be sufficient to provide marginal distribution for each tests.

$$\begin{aligned} Pr(x, v_x, R_x \mid L_y = x) &= Pr(dist(x, y), \vec{xy}, R_y \mid L_y = x) \quad (35) \\ &= Pr(dist(x, y) \mid L_y(x, y), \vec{xy})Pr(\vec{xy} \mid L(x, y)) \\ &\quad Pr(r_y \mid L(x, y)) \\ &= Pr(dist(x, y) \mid x)Pr(\vec{xy} \mid v_x)Pr(R_y, s_x \mid R_x, s_y)(7) \end{aligned}$$

Among the three tests defined above, Applicant has determined that distance tends to be the most reliable. Therefore, it is possible to build a probability model for this distance test. According to some embodiments, a Gaussian model is chosen for the distance test to penalize the distance between point y and candidate x exponentially:

$$Pr(dist(x, y) \mid x) = \frac{1}{\sqrt{2\pi}} \exp\left(-\frac{|x-y|^2}{2}\right) \quad (36)$$

As discussed above, another useful test is determining the extent of direction change in the linked centerline points (e.g., as determined from orientation detection) that would be incurred by linking point y with candidate point x. However, Applicant has appreciated that the direction of the centerline from the orientation detection may zig-zag locally due to digitization. Therefore, relying entirely on the direction obtained from the orientation detection may lead to linking errors. To address this difficulty, some embodiments employ a super Gaussian model to test the possibility of connecting point y with candidate x, given the centerline direction of point x.

$$Pr(\vec{xy} \mid v_x) = \frac{1}{Z} \exp\left(-\frac{\theta(\vec{xy}, v_x)^4}{\sigma^4}\right) \tag{37}$$

The super Gaussian model has a flat top which allows the test to tolerate relatively large angle variation. As discussed above, the centerline response and scale may also be used to test the viability of linking point y with candidate x. It is reasonable to assume that the centerline responses and scale are smoothly changing along a single branch. In the other words, linking to a point which causes centerline to rapidly change may be assigned a low probability. With this intuition, a response test model may be constructed as follows:

$$Pr(R_y, s_y \mid R_x, s_x) = Pr(s_y \mid R_x, s_x) Pr(R_y \mid R_x, s_x, s_y) \tag{38}$$
$$= Pr(s_y \mid s_x) Pr(R_y \mid s_y, R_x, s_x)$$
$$= \frac{1}{Z} \exp\left(-\frac{(s-s_x)^2}{2\sigma_x^2(s)}\right) \exp\left(-\frac{\left(\frac{R_y}{s_y^2} - \frac{R_x}{s_x^2}\right)^2}{2\sigma_r^2}\right)$$

where Z is the normalization factor, $\sigma_s(s)=\max\{0.5, 0.2\ s\}$. Thus, the above test may be employed in connection with the algorithm described above to link the centerline points (e.g., the centerline points that survived non-maximum suppression). Due to errors in the direction finder and grid discretization, some non-centerline points survive from non-maximum suppression. However, the number of those points may be reduced by applying an occupancy constraint. The occupancy constraints operate on the notion that if a local space is occupied by a previously linked branch, then it is not likely possible to be the center of another branch. In the other words, a high confidence may be assigned to long branches to suppress weak branches, if the weak branch occupies the same space as the strong branch.

As a result of linking the centerline points together, each of which represents a poker chip having a center location (the centerline point), a radius r and a direction of the centerline at the center location, further geometry of the vessel may be computed. Referring back to the schematic of the Poker Chip representation in FIG. 2. Having computed each of the center location $c_i$, the radius r and the orientation a, and having linked the adjacent poker chips, additional geometry of the blood vessels may be determined. For example, the linked orientation parameters capture information about the geometry of the centerline. For example, by integrating the orientation vectors, the centerline curve may be obtained. That is, because the orientation vectors represent the tangents of the centerline curve at each location $c_i$, the centerline curve may be recovered from linked tangents by integrating over some desired segment of poker chips.

Figure 13:
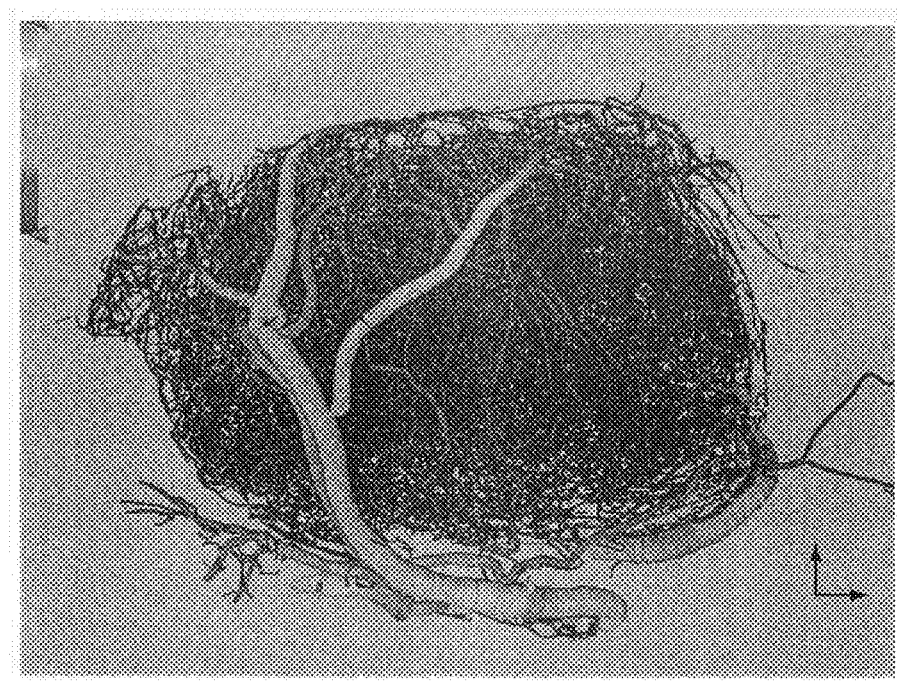
FIG. 13 illustrates a geometrical representation of vasculature obtained from a 3D volumetric image, in accordance with some embodiments of the present invention.

In addition, the linked poker chips may be used to determine higher order and/or more sophisticated geometrical properties. For example, derivatives of the linked orientation vectors may be used to determine the curvature of the vessel. The centerline curve, length of the curve and curvature parameters may be used to determine various tortuosity parameters, which may be used to characterize the vessels. Moreover, the Poker Chip representation carries distribution information with respective to the density of vessel material, the relative distribution of vessels at different radii, etc. These geometrical, structural and distribution parameters may be used in a number of ways to analyze vasculature, as discussed in further detail below. FIG. 13 illustrates a geometrical representation of vasculature using the linked Poker Chip representation, wherein the geometry was extracted from a 3D volumetric image using the methods described herein.

According to some embodiments, the linking algorithm may be performed in parallel. Since linking is generally local and may not need to rely on the information from far away voxels, the algorithm can be parallelized by dividing the image into small blocks. Then individual CPUs may operate on a single block without the need to communicate with other blocks. Because of the computation requires some neighborhood information, each block may include a fixed margin overlapping with its neighbor's margin. The speed gained by parallelization is the number of processors divided by one plus overhead caused by margin. In one example, dividing a volume of 2000×2000×1400 into 500× 500×500 blocks and using 8 processors produced a gain of 4.49 times processing speed.

The margin for parallelization may be chosen based on the following: 1) the margin for the scale selection $m_s=r_{max}+1$; 2) the margin for the smoothing $m_{sm}=3\sigma$; 3) the margin for the gradient computation $mg=1$; 4) the margin for the direction detection $m_d=m_g+r_{max}+1+m_{sm}$; 5) the margin for centerline filtering $m_c=\max\{2r_{max}, m_d\}$; and 6) the margin for the non-maximum suppression $m_{sprs}=r_{max}+m_c$.

Because the block algorithm for parallelization needs to divide the volume into blocks at beginning and assembling the blocks into a volume at the end, away to transform between global coordinates and block coordinates may be needed. The block id $(b_x, b_y, b_z)$ for a point $(i, j, k)$ in the global coordinate is given as:

$$b_x = \left\lfloor \frac{i}{s} \right\rfloor \tag{39}$$
$$b_y = \left\lfloor \frac{j}{s} \right\rfloor$$
$$b_z = \left\lfloor \frac{k}{s} \right\rfloor$$

The local coordinates in its block is (i', j', k')

$$i'=i-b_x s$$
$$j'=j-b_y s$$
$$k'=k-b_z s \tag{40}$$

The dimension $(s_x, s_y, s_z)$ of the block $(b_x, b_y, b_z)$ is:

$$s_x(b_x) = \begin{cases} \mod(N_x, s) & \text{if } b_x = \left\lfloor \frac{N_x}{s} \right\rfloor - 1 \wedge \left\lfloor \frac{N_x}{s} \right\rfloor \neq 0 \\ 0 & \text{if } b_x < 0 \\ s & \text{otherwise} \end{cases} \tag{41}$$

$$s_y(b_y) = \begin{cases} \mod(N_y, s) & \text{if } b_y = \left\lfloor \frac{N_y}{s} \right\rfloor - 1 \wedge \left\lfloor \frac{N_x}{s} \right\rfloor \neq 0 \\ 0 & \text{if } b_y < 0 \\ s & \text{otherwise} \end{cases}$$

-continued $$s_z(b_z) = \begin{cases} \mod(N_y, s) & \text{if } b_z = \left\lfloor \frac{N_z}{s} \right\rfloor - 1 \wedge \left\lfloor \frac{N_x}{s} \right\rfloor \neq 0 \\ 0 & \text{if } b_z < 0 \\ s & \text{otherwise} \end{cases}$$

Given a point (i', j', k') at block ($b_x$, $b_y$, $b_z$), the global offset in the file is:

$$pos = i's_y s_z + j's_z + k' + (\underbrace{\frac{b_z N_x N_y s_z(b_z - 1) + b_y N_x s_y(b_y - 1)s_z(b_z) + b_x s_x(b_x - 1)s_y(b_y)s_z(b_z)}{}}_{\text{block offset}}) \quad (42)$$

The number of blocks in the x dimension is $$n_{bx} = \left\lceil \frac{N_x}{s} \right\rceil,$$

the number of block in the y dimension is $$n_{by} = \left\lceil \frac{N_y}{s} \right\rceil$$

and the number of blocks in the z dimension is $$n_{bz} = \left\lceil \frac{N_z}{s} \right\rceil.$$

A one dimensional block ID l=(1, . . . , $n_{bx}n_{by}n_{bz}$) to 3D index $$b_x = \left\lfloor \frac{l}{n_{by}n_{bz}} \right\rfloor$$

$$b_y = \left\lfloor \frac{l - b_x n_{by} n_{bz}}{n_{bz}} \right\rfloor$$

$$b_z = l - b_y$$

$$n_{bz} - b_x n_{by} n_{bx}$$

Three dimensional block ID ($b_x$, $b_y$, $b_z$) to one dimensional block ID.

As discussed above, the linked Poker Chip representation may be used to determine a number of geometrical and structural parameters of the vasculature, and also may be used to determine distribution information of the vasculature. Provided herein is a description of methods that utilize the extracted geometry to analyze the vasculature for diagnostic, treatment efficacy assessment, therapeutic, and other applications, or any combination thereof.

Information relating to the geometry of a subject's vasculature, or a portion thereof, can be used to determine one or more qualitative and/or quantitative measures of geometrical, structural, and/or distribution parameters of the subject's vasculature that are informative for diagnostic, predictive, prognostic, therapeutic, interventional, research and/or development purposes, as well as for grading and/or staging a disease. It should be appreciated that vasculature geometry may be obtained for any suitable blood vessel volume, as the invention is not limited in this respect. In some embodiments, all the geometrical information captured by the linked Poker Chips within a target volume of interest may be evaluated. However, in some embodiments, useful information may be obtained from analyzing only a subset of Poker Chips within a target volume (e.g., about 10%, about 20%, about 30%, about 40%, about 50%, about 60%, about 70%, about 80%, or about 90%) as the invention is not limited in this respect.

According to aspects of the invention, the types of geometrical or structural information that may be extracted from images (e.g., extracted from a linked Poker Chip representation) includes a measure of vessel curvature, tortuosity, branching, diameter, etc., or any combination thereof. Optionally, or additionally, a measure of vessel density (and/or the density of vessels having one or more predetermined structural characteristics) may be determined and/or analyzed. It should be appreciated that a Poker Chip may consist of or include information relating to the size (radius), angle, etc. of the vessels being represented. In some embodiments, the Poker Chip representation may include linking information (e.g., relating to the linkage angle etc. between a first Poker Chip and one or more adjacent Poker Chips).

Tubular structures (e.g., blood vessels in a cast or in vivo) of different size ranges may be analyzed separately and compared to different threshold or reference values as described herein. In some embodiments, one or more structural parameters are obtained (e.g., calculated or modeled, etc.) for only a subset of size ranges (e.g., only for those size ranges for which changes are known to be associated with a diagnostic, prognostic, clinical, or research application of interest). However, in certain embodiments, all of the size ranges are analyzed. In some embodiments, one or more different parameters are analyzed for different size ranges. However, in certain embodiments, the same parameter(s) is/are analyzed for all of the size ranges that are being assayed. Analyses may be provided in the form of histograms or curves representing a distribution of numerical values or scores obtained for the different ranges.

It should be appreciated that analytical techniques used to categorize blood vessels based on size may be used to categorize other tubular body structures based on size. In some embodiments, once the tubular structures (e.g., blood vessels) are categorized based on size, the associated values or scores obtained for different parameters of interest can also be categorized and analyzed. Aspects of the invention may be automated, for example, as described herein.

Aspects of the invention relate to analyzing data obtained for body structures in animals (e.g., in test animals). In one embodiment, the invention relates to obtaining pattern information relating to one or more aspects or regions of the vasculature of an animal. Pattern information obtained according to aspects of the invention may be used to analyze a disease model (e.g., to assess whether an animal disease model is representative of an actual disease based on structural vascular features, or to assess the progression of one or more vascular changes in a test animal that provides a validated disease model, etc.), to evaluate the effectiveness of a treatment regimen, to identify candidate compounds or treatment regimens that are therapeutically effective, or for other applications where data relating to vascular structures (e.g., the progression of vascular structures, changes in vascular structure over time or in response to different drugs or drug dosages or administration frequencies, etc., or any combination thereof) is informative. For example, aspects of the invention may be used to identify one or more pattern elements that can be used to help diagnose or evaluate diseases, provide prognostic information, monitor treatments, screen therapeutic agents, select one or more therapeutic agents (e.g., help determine or predict a subject's responsiveness to a particular drug), etc., or any combination thereof.

Aspects of the invention may be used to study, identify, and or analyze geometrical, structural, and/or distributional features of blood vessels that are associated with one or more diseases or conditions represented by an animal of interest. In some embodiments, an animal may be a disease model as described herein. In some embodiments, an animal may be undergoing a therapeutic regimen of interest. In some embodiments, an animal may be treated with a candidate therapeutic compound. Accordingly, aspects of the invention may be used to identify, analyze, and/or evaluate one or more vascular patterns or changes in vascular patterns associated with a disease. Aspects of the invention also may be used to evaluate the effects of one or more therapeutic regimens or candidate compounds. In some embodiments, therapeutic effectiveness may be evaluated using one or more vascular patterns or changes therein as a marker of a response (or lack thereof) to treatment. Accordingly, aspects of the invention may be used to identify particular vascular patterns that are indicative of certain diseases or disease stages. These patterns can subsequently be used in sensitive assays to detect diseases in vivo (e.g., in human subjects). Other aspects of the invention may be used to select therapeutic regimens or candidate compounds for administration to a patient (e.g., a human patient) in a therapeutically effective amount and in a physiologically acceptable form.

It should be appreciated that in some embodiments, an animal (e.g., an animal that is perfused with a casting agent composition) may be sacrificed prior to analysis regardless of whether the analysis is performed in situ or not. Accordingly, in some embodiments, changes over time may be studied using a plurality of animals and using one or more animals for each time point of interest. In some embodiments, different dosages, different therapeutic regimens, different drugs or drug combinations, or any combination of two or more thereof may be studied using different animals (with at least one animal for each condition of interest). It should be appreciated that combinations of time courses and drugs, drugs dosages, or other therapeutic regimens similarly may be studied using a plurality of different animals, each representing a unique condition. It should be appreciated that the different animals are preferably genetically identical or similar (e.g., identical for at least one trait that is associated with a disease or condition of interest). In some embodiments, the animals may be mice, rats, sheep, cats, dogs, primates, or any suitable non-human experimental animal.

In some embodiments, a combination of different drugs, different doses, etc., may be evaluated at a series of time points according to aspects of the invention. Again, it should be appreciated that a different animal may represent a different drug, dosage, time point, or combination thereof, because each animal may be sacrificed for analysis. However, in some embodiments, a single animal may be tested at different sites (representing, e.g., different drugs, dosages, time points, etc.) depending on the impact of the casting agent that is used and the site of administration of the casting agent.

In some embodiments, samples from one or more animals may be prepared and analyzed periodically during the time course of a treatment (e.g., using a group of animals exposed to the same experimental conditions). In some embodiments, different conditions may be compared. For example, separate groups of animals (e.g., groups of mice) may be exposed to a candidate drug and a placebo (or other control). In some embodiments, subsets of animals (e.g., one or more animals) may be perfused with a casting agent composition at different time points and vascular structures may be imaged (e.g., directly or through reconstruction) for each time point. For example, tumors may be induced in genetically-altered mice using appropriate controls and different dose levels or regimens (e.g., 1, 2, 3, 4, 5, or more different dose levels or regimens) of one or more therapeutic compounds or compositions. Vascular structures then may be analyzed at different time points using methods of the invention to evaluate the effectiveness of a drug composition and/or to identify biological markers that can be used to monitor a patient response to the drug composition. It should be appreciated that vascular structures of different sizes may be studied to identify structural features and/or distribution patterns of interest. In some embodiments, blood vessels having a diameter of about 50 microns are studied. However, it should be appreciated that smaller or larger vessels, or a combination thereof, may be studied.

In some embodiments, a vasculature characteristic may be evaluated over time by comparing results at different time points. However, it should be appreciated that the end-point of a study may be used as a single time point and characteristics associated with different diseases or treatments may be compared to identify or infer changes associated with a disease, treatment, or other condition of interest. Aspects of the invention can be used to analyze data obtained from any suitable image source to identify one or more patterns associated with tubular structures of different sizes (e.g., structural patterns of blood micro-vessels). One or more parameters of a structural pattern can be used as biomarkers for different biological conditions and processes (including pathogenic conditions). Accordingly, aspects of the invention relate to disease detection, diagnosis, grading, staging, disease monitoring, monitoring the effectiveness of therapy and interventional applications based on an analysis of structures (e.g., in situ structures) to identify patterns that may be associated or correlated with a disease or other physiological condition. According to the invention, a pattern may comprise one or more different parameters. Parameters may be one or more structural features of individual tubular structures and/or one or more distribution properties (e.g., spatial distribution, spatial orientation, frequency, number, etc., or any combination thereof) of one or more tubular structures and/or one or more distribution properties (e.g., spatial distribution, spatial orientation, frequency, number, etc., or any combination thereof) of one or more individual tubular structural features within a subject or a within a region of interest in the subject, or any combination thereof. Accordingly, a vasculature pattern may include one or more structural features of an individual blood vessel (e.g., micro-vessels), a distribution of one or more blood vessels (e.g., micro-vessels) within a subject, a distribution of one or more individual blood vessel structural features (e.g., individual micro-vessel structural features), or any combination thereof. An individual blood vessel structural feature may include, but is not limited to, vessel tortuosity, curvature, branching (e.g., frequency, angle, hierarchy, etc.), diameter, direction, etc., or any change (e.g., variation or frequency) of any of these features over a predetermined length of the blood vessel being analyzed, or any combination thereof. A distribution of blood vessels or individual blood vessel structural features may include, but is not limited to, a blood vessel density, a distribution of blood vessel directions, a distribution of blood vessel diameters, a distribution of distances between blood vessels, a distribution of blood vessel spatial orientations (e.g., relative to each other), a distribution of blood vessel curvatures, a distribution of any other individual blood vessel structural features described herein, other distributions of blood vessel parameters or any combination of two or more thereof. It should be appreciated that the distribution of blood vessels or blood vessel structural features may be determined and/or analyzed for a predetermined region within a subject (e.g., a target volume of tissue within a subject) or within predetermined tissues or organs within a subject or throughout the subject (e.g., within a vascular cast). It also should be appreciated that either the absence or presence of blood vessels or of individual blood vessel structural features within a predetermined volume being analyzed may be a pattern parameter that can be used in analytical methods of the invention. It also should be appreciated that one or more pattern parameters may be monitored and/or analyzed as a function of time. Accordingly, blood vessel patterns can be used as biomarkers for different biological conditions and processes (including pathogenic conditions). Accordingly, aspects of the invention relate to identifying and evaluating biological markers that may be used for in vivo disease detection, diagnosis, grading, staging, for disease monitoring, for monitoring the effectiveness of therapy and interventional applications in live animals, including humans, based on an analysis of vasculature patterns including vasculature morphology and/or architecture in experimental subjects, for example experimental animals (e.g., animals perfused with one or more casting agent compositions). In one embodiment, the in vivo density, and/or diameter distribution, and/or geometric orientation of blood vessels (e.g., micro-vessels) may be analyzed, quantified, and/or evaluated for disease detection, monitoring, and/or interventional applications. In one embodiment, the sensitivity and specificity of disease diagnosis may be enhanced by analyzing and evaluating in vivo vasculature morphology and/or architecture associated with a tissue lesion. Accordingly, aspects of the invention include detecting in vivo indicia of diseases associated with abnormal vascular structures or patterns. Other aspects include disease diagnosis, staging, grading, monitoring and prognosis, patient treatment, drug development and validation, and research applications. It should be appreciated that one or more biological markers identified in vascular casts in association with a response to a known drug or treatment may be used as a reference markers to evaluate the effectiveness of additional drugs or treatments in comparison to the known drug or treatment.

Certain embodiments according to the present invention includes a method of analyzing geometric features of blood vessels and correlating one or more features with a biological process, condition, or disease. Accordingly, certain geometric features of blood vessels may be used as biomarkers indicative of particular biological processes, conditions, and/or diseases.

In some embodiments, data for tubular structures (e.g., blood vessels) may been sorted into bins based on their size (e.g., their diameter). Aspects of the invention may increase the analytical resolution when evaluating structural information that is obtained for one or more experimental models and/or subjects being evaluated. According to aspects of the invention, a binned structural analysis refers to any analysis of tubular structures that have been sorted or categorized according to size (e.g., according to the diameter or radius of the tubular structure in an area of interest). For example, in some embodiments a binned micro-vessel density (BMVD) analysis refers to an analysis of blood vessel density based on blood vessels that have been categorized according to vessel diameter in an area of interest.

Binned analytical techniques can be applied to the analysis of many different parameters that may be characteristic of tubular structures. Binned analytical techniques may be performed on tubular structures observed in casts or in vivo (e.g., in situ). For example, bins of tubular structures having different diameters can be evaluated to determine one or more of the following parameters: tortuosity, curvature, density, branching frequency, branching hierarchy (e.g., presence or absence of a branching hierarchy), relative distribution and/or direction of tubular structures (e.g., blood vessels), etc., or any combination thereof. By performing the analysis on binned data, small changes that primarily affect structures in one size range are more likely to be detected, because they are not masked by a relative absence of change in structures in other size ranges. Accordingly, methods of the invention can be used to refine an analysis of tubular structures (e.g., blood vessels) over time or in response to disease or treatment, etc., where the analysis may be performed on casts and/or in vivo. Aspects of the invention can also be used to detect or delineate diseased tissue (e.g., cancerous or pre-cancerous tissue, necrotic regions, etc.) in casts and/or in vivo.

It should be appreciated that, regardless of the source of information relating to vessel geometry, structure, and/or distribution (e.g., from analysis of BMVD, casts, in vivo, images, representations, etc., or any combination thereof), analytical methods described herein may be used. Accordingly, any analytical descriptions of vessel distributions that are provided in the context of one source of information may be applied to that analysis of vessel distributions obtained from one or more other sources as appropriate.

In some embodiments, spatiotemporal information about the vessel distribution provides numerous indicators about the health of a tumor, the effectiveness of a treatment such as the efficacy of a particular anti-angiogenic drug, and how a tumor is changing over time with respect to differently sized vessels. Numerous exemplary applications using one or more distribution analyses (e.g., based on BMVD measurements), in accordance with various aspects of the present invention are described herein. Applicant has identified and disclosed various applications that are facilitated by the acquisition of information about vessel characteristics, distribution, size, shape, etc., in PCT application US2005/047081 filed on Dec. 22, 2005, which is hereby incorporated by reference in its entirety. Applicant has appreciated that certain of these applications are facilitated by obtaining one or more BMVD measurements or by using one or more alternative binned analyses. It should be appreciated that any application may involve an analysis limited to one or more (e.g., 2, 3, 4, 5, 6, 7, 8, 9, 10, or more) bins of microvasculature of different sizes. For example, binned analyses may be useful for diagnostic applications. In one embodiment, aspects of the invention can be used to detect and diagnose diseases associated with patterns (e.g., individual structural features or distributions) of in situ tubular networks. In some cases, a diagnosis can be rendered from an examination of the patterns (e.g., individual structural features or distributions) of interest at a single time. Alternatively, disease progression in a subject can be tracked by performing a structural analysis at two or more (e.g., 3, 4, 5, 6, 7, 8, 9, 10, or more) time points. Disease tracking can be used to provide diagnostic and prognostic information for a patient. For example, disease progression information can be used to assess the aggressiveness and/or invasiveness of a tumor.

The invention can be used to screen an individual or a population for the presence of indicia relating to one or more diseases. As mentioned herein, the screen may be a whole body screen, or may be focused on one or more target regions (e.g., specific organs or tissues).

In one embodiment, the techniques described herein can be used automatically to identify individuals with one or more disease-associated structural patterns or features. These individuals can be subsequently tested for additional indicia of disease. The subsequent testing can take any suitable form, as the aspects of the present invention described herein are not limited in this respect. For example, follow on testing can employ conventional techniques. As a non-limiting example, the use of aspects of the present invention may enable cost-effective screening techniques that may identify a relatively small pool of candidates as at risk of a disease, and may justify the use of relatively more expensive testing procedures to reach a final diagnosis or prognosis, wherein the follow on techniques may be too expensive to administer to a wider sample that has not been narrowed using the techniques of the present invention described herein. As a further example, aspects of the present invention described herein, either alone or in combination with other techniques, can be used to perform subsequent tests. In this respect, the sensitivity of the initial screening can be set relatively high, such that it may indicate some false positives, and subsequent application of techniques in accordance with aspects of the present invention described herein can be employed with a higher degree of sensitivity that may provide more detailed information.

In one embodiment, aspects of the present invention can be used to screen a population of at risk individuals (e.g., individuals with genetic or other risk factors for a disease such as cancer, a circulatory disorder, or other disease) to identify the presence of disease indicia in one or more individuals.

In one embodiment, diagnostic methods of the invention are computer-implemented to increase efficiency and throughput, and reduce variability associated with individual physicians. However, as discussed herein, in some embodiments, the final diagnosis may be made by a physician based on information generated by an automated analysis or a structural representation using aspects of the invention described herein.

As shall be appreciated from the foregoing, aspects of the invention can be used on patients known to have a disease, or can be used to screen healthy subjects on a regular basis. A subject can be screened for one or more diseases. Screening can be done on a regular basis (e.g., weekly, monthly, annually, or other time interval); or as a one time event. Different conditions can be screened for at different time intervals and in function of different risk factors (e.g., age, weight, gender, history of smoking, family history, genetic risks, exposure to toxins and/or carcinogens etc., or a combination thereof).

In one embodiment, aspects of the invention can be employed to diagnose, evaluate or stage diseases associated with changes in vasculature structure. The detection of small changes in vasculature structure may be informative for early stage disease detection and disease monitoring. A morphological determination of binned blood vessels may be analyzed and one or more patterns (e.g., individual structural features or distributions) may be evaluated for the presence of abnormal properties. In one embodiment, a vasculature structure may be obtained including a series of interconnected branched blood vessels and may include arteries, arterioles, veins, venules, capillaries, and other sized blood vessels. However, according to aspects of the invention, an interconnected vasculature structure is not required and different sizes of blood vessels can be analyzed separately and represented on a histogram or other form of distribution representation. In some aspects of the invention, blood vessels of the entire body can be analyzed, and in other aspects the blood vessels of a target organ, tissue, or part thereof can be analyzed. In some aspects of the invention, only a subset of blood vessel sizes is binned and analyzed (e.g., blood vessels with a diameter below about 500 microns, preferably below about 200 microns, more preferably below 100 microns, even more preferably below 50 microns, and even more preferably below 25 microns). In one embodiment, only capillary blood vessels are analyzed. In another embodiment, capillaries and small arteries and veins (e.g., arterioles and venules) are analyzed. For example, an arborescent vasculature can be analyzed in any tissue where it is found (e.g., an arborescent mucosal vasculature such as the oesophageal arborescent mucosal vasculature).

The branches of a vascular tree may be analyzed to glean information about the status of the patient. In one embodiment, the branches of a vascular tree may be followed to identify specific regions where certain characteristics of angiogenesis may be evaluated (e.g., start with a large branch and follow the tree to second, third, or fourth, or subsequent levels of branching to identify small blood vessels that may have abnormal structures if they are providing a blood supply associated with a disease). Alternatively, several different blood vessel sizes in the vascular tree may be evaluated for signs of angiogenesis. In another embodiment, the overall branching pattern of a vascular tree can be analyzed. For example, a healthy vascular tree may be approximately hierarchical in that the size of the blood vessels generally decreases as the vessels branch. In contrast, a diseased (e.g., angiogenic) vascular tree may be less hierarchical with areas of significant blood vessel branching with little or no decrease in blood vessel size. It should be appreciated that the nature and extent of the analysis may depend on the goal of the diagnostic evaluation. For example, a full body scan can be evaluated selecting all vascular structures and analyzing the entire vascular network for signs of different diseases. Alternatively, a region of a body suspected of being diseased may be selected and the data may be processed to focus on the vasculature in that region (e.g., to obtain a segmented representation of structures in the region of interest). A region of interest may be an organ (e.g., pancreas, liver, breast, colon etc.) or a tissue (e.g., skin epidermal tissue). The presence of an abnormal vasculature structure can be an early indication of a range of diseases for which early detection is critical for effective treatment.

Diseases associated with changes in vascular structure (e.g., that can be detected by the presence of abnormal vascular patterns at a given time or abnormal structural changes observed as a function of time) include, but are not limited to, cancer, heart diseases and related circulatory disorders, eye diseases, skin disorders, and surgical conditions. For example, diseases and conditions associated with changes in vascular structure include, but are not limited to, tumor angiogenesis, recurrent and progressive cancers, coronary artery disease, cardiomyopathy, myocardial ischemia, arteriosclerosis, atherosclerosis, atherosclerotic plaque neovascularization, arterial occlusive disease, ischemia, ischemic or post-myocardial ischemia revascularization, peripheral vascular disease (including diabetic retinopathy), thromboembolic diseases (e.g., stroke, pulmonary embolism, brain aneurisms, and deep venous thrombosis), claudication, rheumatologic disorders (e.g., arthritis), immune disorders (e.g., rheumatoid arthritis, vasculitis, Wegner's granulomatosis, and systemic lupus erythematosis (SLE)), pulmonary disorders (including, emphysema, COPD, idiopathic pulmonary fibrosis, pulmonary arterial hypertension, and other respiratory disorders), myeloma, vascular proliferative disorders, gastrointestinal disorders (e.g., Crohn's disease, ulcerative colitis, and inflammatory bowel disease (IBD)), gynecologic disorders (endometrial polyp, vaginal bleeding, endometriosis, dysfunctional uterine bleeding, ovarian hyperstimulation syndrome, preeclempsia, polycystic ovarian syndrome (PCO), cervical cancer, and cervical dysplasia), skin disorders (infantile hemangioma, verruca vulgaris, psoriasis, neurofibromatosis, epidermolysis bullosa, Stevens-Johnson syndrome, and toxic epidermal necrolysis (TEN)), eye disorders (macular degeneration, maculopathies, diabetic retinopathy, and retinopathy of prematurity (retrolental fibroplasia)) wound healing, inflammation associated with immune responses, ischemia including limb ischemia and cardiac ischemia, Alzheimer's disease and other disorders such as wound dehiscence, Buerger Disease (thromboangitis obliterans, arteriosclerosis obliterans (ASO), ischemic ulcers) multiple sclerosis, idiopathic pulmonary fibrosis, HIV infections, plantar fasciosis, plantar fasciitis, Von Hippel-Lindau Disease, CNS hemangioblastoma, retinal hemangioblastoma, thyroiditis, benign prostatic hypertrophy, glomerulonephritis, ectopic bone formation, and keloids.

These different diseases are characterized by different changes in vasculature structure. Accordingly, in one aspect of the invention, parameters and scoring methodologies are used to detect, diagnose, and monitor particular diseases and their related therapies based upon particular characteristics of vasculature structure indicative of the disease. Even within each disease category, different diseases can be characterized by different changes in vasculature structure. Accordingly, structure mining and scoring can be fine-tuned to increase the sensitivity for particular types of disease within a category (e.g., lung cancer score, breast cancer score, etc., can be developed). Patient-specific scoring parameters can also be developed to follow the progression of a specific disease or disorder in a patient.

Structural vasculature changes include changes in vascular architecture and vascular morphology affecting blood vessels and/or lymph vessels. Structural changes can involve neovascularization (including the growth of large blood vessels (e.g., arteriogenesis) and the growth of microvasculature (angiogenesis)), large blood vessel expansion, and vascular necrosis. Angiogenesis involves the formation of new blood vessels that sprout from preexisting blood vessels. Angiogenesis is different from vasculogenesis, which is the de novo formation of vessels that occurs primarily during development. Vasculogenesis is rarely associated with a disease or disorder. However, aspects of the invention can be used to study the natural process of vasculogenesis to help identify and understand defects in de novo blood vessel formation.

Angiogenesis is often associated with tumor growth and is a useful biomarker for cancer. Angiogenesis also can be associated with conditions where new blood vessel growth occurs in response to a reduced oxygen supply or blood flow (whether due to thrombosis, embolism, atherosclerosis, or other chronic occlusion or narrowing of the vasculature).

Certain respiratory, cardiovascular, and inflammatory disorders also are associated with angiogenesis.

Angiogenic blood vessels have structural characteristics that are different from those of established blood vessels. For example, the branching patterns and tortuosity of angiogenic blood vessels are very different from those of normal blood vessels. These and other structural features are found predominantly in microvasculature and can be used for mining and scoring vasculature structural images. However, changes in larger blood vessels such as arteries and veins also may be associated with certain diseases or disease stages (e.g., growth and development of large tumors or late-stage tumors).

The vasculature that supports a tumor is typically associated with the connective tissue of the tumor (the stroma) that supports the malignant cells (in the parenchyma). As discussed herein, tumor blood vessels are irregularly spaced and characterized by heterogeneous structural patterns or features. However, the formation of tumor blood vessels and other forms of angiogenesis may involve a series of characteristic stages (see, for example, Dvorak, 2003, American Journal of Pathology, Vol. 162:6, pp. 1747-1757, the disclosure of which is incorporated herein by reference in its entirety). Early stage angiogenesis may be characterized by vascular hyper-permeability, fibrin deposition and gel formation, and edema. This may result in the enlargement of micro-vessels such as venules. The cross-sectional area of an enlarged micro-vessel may be about 4 fold that of a normal micro-vessel. The perimeter of an enlarged micro-vessel may be about 2 fold that of a normal micro-vessel. Enlarged micro-vessels may occupy about 4-7 fold the volume of normal micro-vessels in a region of active angiogenesis. The appearance of enlarged micro-vessels may be followed by the appearance of "mother" vessels that are enlarged, thin-walled, serpentine, and hyper-permeable. Mother vessels may undergo a process of bridging whereby trans-luminal bridges are formed dividing the blood flow within the vessel into smaller channels. A developing mother vessel also may contain one or more glomerular bodies that may expand to divide the lumen of the mother vessel into several smaller channels that are typically tortuous. Bridging and glomerular body formation in mother vessels may lead to the appearance of small capillaries characteristic of angiogenesis. However, certain mother vessels persist as abnormally enlarged vessels with thin walls. These vascular malformations are often characterized by the presence of an asymmetric muscular coat and perivascular fibrosis. Small arteries and arterioles also may increase in size in diseased tissue. Aspects of the invention include detecting and/or monitoring any one or more of the blood vessel structural changes described herein. In one embodiment, the presence of one or more patterns (e.g., individual structural features or distributions) characteristic of new blood vessel formation may be used to detect or monitor a disease. In another embodiment, the presence of one or more specific patterns (e.g., individual structural features or distributions) may be used to determine the stage of angiogenesis (e.g., early-stage, mid-stage, late-stage, etc.) in a body region.

Accordingly, abnormal changes in blood vessel size (diameter and/or length) can be early signs of diseases such as cancer or other disease associated with an increased blood supply. Changes in blood vessel size may occur before any structural signs of angiogenesis appear. In one embodiment, aspects of the invention are useful to detect blood vessels (e.g., capillaries) that are swollen and/or longer than normal. For example, aspects of the invention are useful to detect abnormally long intrapapillary capillary loops in situ (e.g., associated with early stages of cancer in oesophageal mucosa).

In some embodiments, blood vessel changes indicative of necrosis in tumor tissues may be indicative of the aggressiveness of the tumor tissue and/or the likelihood of metastasis, and/or the responsiveness to therapy, and/or the efficacy of a therapeutic treatment (e.g., a candidate drug), and/or an therapeutic treatment selection and/or modification (e.g., a change in drug or dose for an individual patient). Accordingly, in situ patterns (e.g., individual structural features or distributions) indicative of necrosis may be useful biomarkers for patient prognosis. In certain embodiments, necrosis within a region of a tumor may be indicated by one or more of the following patterns (e.g., individual structural features or distributions) within that region: a collapse in blood vessel structure, poor vascularization (e.g., a low blood vessel density relative to other regions of the tumor or relative to the perimeter of the tumor), a change in blood vessel size or shape over time, a lower than threshold number of blood vessels, blood vessels (e.g., in the microvasculature or the capillaries) that are separated by a greater than threshold distance (e.g., by more than 100 microns, more than 150 microns, or more than 200 microns) within a volume of the tumor, micro-vessel diameter and/or density indicative of undervascularization, etc., or any combination thereof. In some embodiments, a volume of avascularization or undervascularization may be evaluated or quantified and used as an indicator of necrosis. It should be appreciated that other indicia of necrosis may be used, alone or in combination with blood vessel features. Other indicia may include indicia of tissue collapse or cavitation that may be visualized (e.g., using CT etc.) and/or indicia of tissue viability using one or more markers of metabolic activity (e.g., ones that may be analyzed using a PET scan, etc.). One or more reference indicia (e.g., a reference volume of avascularization or undervascularization may be identified by analyzing vascular casts of necrotic tumor tissue (e.g., in a xenograft tumor model, for example in an orthotopic or an ectopic tumor xenograft).

Aspects of the invention may be used for the detection (e.g., the automatic detection)

Aspects of the invention may be used for the detection (e.g., the automatic detection) of necrotic areas in a subject (e.g., in a tumor in a subject). A necrotic region is an avascular region within the boundary of a diseased tissue. Methods of the invention may be used to detect (e.g., automatically) the transition between the vascularized diseased tissue and avascular region that defines the boundary of the necrotic region.

Aspects of the invention also may be used to detect or evaluate (e.g., automatically) a response to therapy. For example, a response to therapy (e.g., to a specific drug and/or a specific dosage of a drug, and/or to a combination of drugs and specific dosages of these drugs, etc.) can be detected and assessed as follows. Changes in the vascular patterns (e.g. vessel normalization/straightening, disappearance of smaller diameter vessels leading to lower microvessel density and to skewing of the vessel diameter distribution towards the larger vessels) may be detected and/or evaluated within the volume defined by the boundary of the diseased tissue and the boundary of the necrotic area. An increase in the absolute volume size of the necrotic area and/or the rate of such change while the total volume of the disease (e.g. tumor) volume stays constant may be detected and/or evaluated as an indicator that the therapy is effective. An increase in the ratio between the absolute volume size of the necrotic area and the total disease (e.g., tumor) volume and/or the rate of change in this ratio may be detected and/or evaluated and used as an indicator that the therapy is effective. A ratio of the diseased tissue volume and the necrotic region volume may be detected and/or evaluated and when it approaches 1 and the overall diseased tissue volume starts shrinking it provides an indication that a therapy is effective. In some embodiments, reference indicia may be obtained from analyzing casts (e.g., appropriate vascular casts). However, reference indicia may be obtained from any suitable data relating to blood vessel structures (e.g., view data, scan data, in vivo data, etc., or any combination thereof).

Structural representations of blood vessels can be mined to identify and evaluate certain patterns (e.g., individual structural features or distributions) that can be used to provide a score that is related to the probability that the blood vessels are normal or abnormal (e.g., disease associated). Accordingly, in some embodiments a binned analysis may be predictive of a response to therapy.

In certain embodiments, a binned analysis may be sensitive to vasculature changes resulting from unwanted side-effects associated with one or more therapeutic drugs. Accordingly, binned analysis may be used to detect or quantify toxic side-effects of certain drugs.

The morphology of blood vessels (e.g., binned blood vessels) can be mined to identify and evaluate certain patterns (e.g., individual structural features or distributions) that can be used to provide a score that is related to the probability that the blood vessels are normal or abnormal (e.g., disease associated). Patterns (e.g., individual structural features or distributions) for scoring blood vessels include, but are not limited to, the following: diameter, curvature, tortuosity (including, for example, the degree of tortuosity, the length of the blood vessel along which abnormal tortuosity is observed, etc.), variability or heterogeneity (including spatial variability or heterogeneity over distance or in a volume), branching shape or pattern, branching density, branching hierarchy, blood vessel density, distribution of vessel size (ratio of microvasculature to macrovasculature) a field effect (the presence of blood vessels bending towards a specific region), blood vessel diameter distribution, variability of the geometric orientation of blood vessels or fragments thereof, and the distribution of the orientation(s) within a field. The score may have more significance if two or more (e.g., 3, 4, 5, 6, 7, 8, 9, 10, or more, or all) of these parameters are evaluated. In some embodiments, a score is generated using one or more of these structural parameters combined with additional information such as patient-specific medical information (e.g., age, weight, height, gender, etc.) and the presence of one or more additional indicators of disease such as a visible lesion on an X-ray or other image. In some embodiments, a score can be provided for a tumor. An example of a useful score is one that reflects the vascularity of a tumor. An abnormally high vascularity (measured as a higher than normal blood vessel number, density, length, or combination of the above) is generally indicative of a more aggressive or invasive tumor. In one embodiment, vascularity is evaluated by measuring the volume of the lumen of angiogenic vasculature (the volume within the blood vessel tree associated with a tumor). In another embodiment, a measure of vascularity is provided by dividing the volume of the angiogenic lumen by the volume of the solid tumor. Additional information can be gleaned from obtaining a score (or other structural evaluation) at two or more times. A changing score (or other structural evaluation) is indicative of an evolving vasculature that could be associated with a disease or disorder. It should be appreciated that the patterns (e.g., individual structural features or distributions) described herein can be identified and analyzed for a field of analysis without imposing a connectivity on the vessels being studied. In some embodiments, it may be sufficient to analyze only fragments of blood vessels in order to detect one or more structural features of individual vessels or geometrical features of a field of vessels that are different from normal features. For example, blood vessel fragments having an average length of 0.5 mm, 1 mm, 5 mm, 10 mm, 50 mm, 1 cm, 5 cm, 10 cm, 50 cm, etc. may be used. However, it should be appreciated that shorter or longer or intermediate lengths may be used. The scoring and mining aspects of the invention described herein can be automated. Accordingly, diseased (e.g., angiogenic) vasculature can be automatically detected amidst normal vasculature. Various vasculature parameters can be automatically detected and scored, either separately or in any combination, including vessel tortuosity, vessel branching, vessel density, and total intra-vascular volume, but the invention is not limited to any particular parameter or combination.

In one embodiment, aspects of the invention can be used to detect blocked blood vessels, and thromboembolic events, including stroke, lung emboli, blocked micro-coronaries, deep-vein thrombosis, etc. Blocked blood vessels can be detected (1) directly by detecting structural changes in the blocked blood vessel (e.g., detecting a clot, wall thickening, or other signs of reduced flow) and/or (2) indirectly by detecting new vasculature that was generated in response to the blockage. In general, the formation of collateral blood vessels is more ordered than angiogenesis associated with cancer. One aspect of the invention described herein also allows clots to be detected in small blood vessels.

As discussed herein, aspects of the invention can be used to screen the entire vasculature structure of a human or other animal to screen for any form of abnormality in any tissue. Alternatively, a subset of the body may be screened. Accordingly, the structures of binned vessels can be analyzed for one or more organs or tissue types. In addition, only a portion of the vessels in any predetermined bin may be analyzed within any target volume as opposed to the entire vascular tree in that volume. This may be done by analyzing structure data focused on the area of interest, or large amounts of structure data may be obtained, but an analysis may be restricted to a subset of the available data. In some embodiments, only a portion of a vascular tree may be binned and/or analyzed, for example only a portion of those vessels that are of a particular size range. In some embodiments, only fragments of a vascular tree are represented and/or analyzed if the fragments are sufficiently informative to provide patterns (e.g., individual structural features or distributions) of interest. Fragments may include branches or may be unbranched. The portion of the vasculature being analyzed may be statistically significant, such that any observation (normal or abnormal) is physiologically significant. For example, branched structures may not be required for the analysis if a sufficient number of vessel substructures are analyzed to confidently detect any other patterns (e.g., individual structural features or distributions) that may be associated with vasculature changes (e.g., angiogenesis) such as high vessel density. In aspects of the invention, vascular patterns may be detected and/or evaluated in situ in a volume of 1 $mm^3$, 2 $mm^3$, 5 $mm^3$, 1 $cm^3$, 2 $cm^3$, 5 $cm^3$, 10 $cm^3$, etc. However, smaller or larger or intermediate volumes also may be analyzed. In some embodiments, vascular patterns or structures are evaluated over an entire model tissue or organ (e.g., for an entire orthotopic or ectopic tumor model).

Different tissues and organs have different and characteristic blood vessel patterns (e.g., the lung which is highly vascularized). Accordingly, in one embodiment, structural analyses and associated structural parameters may be optimized for evaluating different tissues.

In some embodiments, scan data is obtained and/or analyzed for one or more organs (e.g., lung, heart, colon, brain, liver, pancreas, kidney, breast, prostate, etc.) or tissue (e.g., skin, bone, etc.) or portion of any of the above.

Brains may be evaluated for signs of brain tumors and/or other neurological disorders that can be associated with changes in vascular patterns. For example, Alzheimer's may be associated with certain vascular abnormalities. In one embodiment, one or more changes in blood vessel pattern (e.g., shape and/or size) may be detected as an indicator of high blood pressure in the brain.

In some embodiments, certain specific regions of organs or tissues are focused on. For example, atherosclerosis is typically found in certain parts of the arterial tree (e.g., bifurcations, side branches, regions opposite flow dividers, and other areas where angiogenesis often occurs in association with atherosclerosis) and certain cancers tend to occur more frequently in certain organ or tissue regions (e.g., colon cancers are not distributed evenly along the length of the colon).

In other embodiments, aspects of the present invention may be used to follow up with individuals who have been identified as having one or more other indicia of disease (e.g., fecal occult blood, a colon polyp, a lung nodule, one or more cysts or other indicia of disease). Aspects of the invention may be used to confirm the presence of a disease, determine a location for the disease-associated lesion, or provide an evaluation or prognosis of a disease. For example, aspects of the invention may be used to determine whether abnormal vasculature is present at the site of a lesion (e.g. a colon polyp, a lung nodule, a bladder cyst, a prostate cyst, a breast cyst, a spot on a mammography, or any other cyst, lump, or spot that may be detected physically, visually, or using any other diagnostic technique) and help evaluate the likelihood of a malignancy (or other carcinogenic disease stage) associated with the lesion. Accordingly, aspects of the invention may be used for virtual malignancy detection (e.g., virtual colonoscopy, virtual colon malignancy detection, virtual bronchoscopy, virtual lung malignancy detection, virtual mammography, virtual cystoscopy, etc.).

In other embodiments, aspects of the invention may be used for screening a cancer patient to evaluate the extent of a cancerous lesion and/or to screen for the presence of one or more metastatic lesions (e.g., one or more loci associated with angiogenesis). A cancer patient may be screened upon initial diagnosis of a primary cancer. In addition or alternatively, a cancer patient may be screened at least once after an initial cancer treatment (e.g., surgery, radiation, and/or chemotherapy). This screening may include the original cancer locus to detect any cancer recurrence. This screening may include similar body tissue to screen for the presence of other lesions in the same tissue or organ (e.g., the entire colon may be screened when a cancerous lesion is detected in one region of the colon, the second breast may be screened when a cancerous lesion is detected in one breast, etc.). This screening also may be extended to the whole body or to one or more other loci suspected of containing a metastatic lesion. In one embodiment, a cancer patient may be screened several times after an initial cancer treatment (e.g., at time intervals of about 6 months, about 1 year, about 2 years, about 5 years, or at other time intervals).

In one embodiment, a follow up procedure may involve screening one or more organs or tissues for the presence of a metastatic lesion. Different cancers may have different characteristic patterns of metastasis. Accordingly, different target loci may be screened for different cancers. For example, metastatic breast cancer typically spreads to the lungs, the liver, bone, and/or the CNS. Therefore, one or more of these tissue types or organs may be screened after a patient is diagnosed with breast cancer. Similarly, other target loci may be screened after a patient is diagnosed with another cancer type. In some embodiments, the entire body of a cancer patient may be screened for indicia of metastasis.

In one aspect, an initial screen may be performed on an entire body, or an entire organ, using a low resolution representation and/or, for example, analyzing only one or two or a small number (e.g., less than five) pattern parameters in order to detect indicia of a disease. Subsequently, the presence and or nature of the disease may be diagnosed using a higher resolution representation and/or, for example, analyzing one or more additional pattern parameters or alternative pattern parameters than those that were analyzed for the initial detection.

In some embodiments, small changes in blood vessel distributions may be observed (for example as measured by a ratio between the number of blood vessels of two or more different sizes in a region of interest, for example, a tumor in an animal model) and used as a biomarker. Such biomarkers may represent early changes (e.g., early changes in tumor growth or response to therapy) that occur before later changes in tumor size and/or tumor morphology. It should be appreciated that some or all of the diagnostic aspects of the invention can be automated as described herein.

It should be appreciated that some or all of the diagnostic aspects of the invention can be automated as described herein.

Aspects of the invention also can be used to identify the location of a disease by locating one or more structural abnormalities associated with the disease. This information can be used to target a biopsy procedure or a treatment (e.g., a treatment with one or more toxic chemicals, radiation, heat, cold, small molecules, gene therapy, surgery, any other treatment, or a combination of two or more of the above) to the precise location of a disease lesion, or for any other purpose.

In one embodiment, an imaging device is connected to a computer that provides a real-time visual display of the disease lesion. In one embodiment, a real-time visual display may be an accurate model of a body region and lesion along with associated vasculature (as opposed to an actual image). This visual information can be used to guide a surgical instrument for a biopsy. Alternatively, the information can be used to guide an invasive (e.g., surgical removal or bypass) or non-invasive (e.g., radiation) treatment procedure to the site of the disease lesion (e.g., tumor or blood clot).

In some embodiments, aspects of the invention may be used to define the boundary between diseased and non-diseased tissues, or between necrotic and non-necrotic tissue, etc., or any combination thereof. For example, a boundary may be identified or defined by analyzing binned data for several areas of interest and identifying adjacent areas having very different blood vessel densities (or differences in other morphological parameters that are associated with disease, necrosis, etc., or any combination thereof.

In one embodiment, aspects of the invention may be used to identify an area of tissue for treatment before the treatment is applied. For example, a treatment target region may be identified by detecting a boundary of chaotic blood vessel structures. The area may be assessed after treatment to confirm that the treatment was appropriately targeted. In one embodiment, a structure may be analyzed pre-operatively to identify the extent of tissue to be removed from a body region. In one embodiment, a body region may be analyzed post-operatively to determine whether any abnormal structures were missed. This may be used to confirm the success of a radiation treatment or a surgical removal of diseased tissue. Alternatively, this may be used to decide on further surgery and/or another form of treatment. In another embodiment, a disease boundary may be defined or depicted by the boundary of abnormal vasculature. A treatment (e.g., radiation therapy, surgery, etc.) may be guided by and/or restricted to a volume encompassed by the disease boundary.

In one embodiment, aspects of the invention can be used to evaluate the success of a surgical implant or transplant. For example, aspects of the invention can be used to evaluate the formation of new blood vessels after an organ or tissue transplant.

In another embodiment, the development of new blood vessels may be monitored after removal of tumor tissue or after a tumor biopsy, both of which may trigger angiogenesis and/or convert a dormant tumor into a malignant tumor.

It should be appreciated that some or all of the interventional aspects of the invention can be automated as described herein.

Aspects of the invention also can be used to optimize a therapeutic treatment for a patient. The extent of disease progression or regression can be monitored in response to different treatment types or dosages, and an optimal treatment can be identified. The optimal treatment may change as the disease progresses. The effectiveness of the treatment over time can be monitored by analyzing changes in disease-associated patterns (e.g., individual structural features or distributions) using the aspects of the present invention described herein.

In one embodiment, a first therapy can be administered and its effectiveness on slowing, stopping, or reversing abnormal blood vessel growth can be monitored either irregularly or at certain time intervals (e.g., daily, weekly, monthly, or other time intervals). In some embodiments, if a first therapeutic regimen does not have a desired effect on disease progression, a second therapeutic regimen can be evaluated. Similarly, additional therapeutic regimens can be evaluated on a patient-by-patient basis. Additionally, the invention can be used to optimize a chosen therapeutic regimen (e.g., optimize dosage, timing, delivery, or other characteristic of a drug or other treatment) by monitoring the effect of minor therapeutic changes and using the conditions that appear to be most effective for the condition and the patient.

When looking at the therapeutic effectiveness of a treatment, disease-specific parameters may be monitored. Of course, all parameters can be obtained and only a subset reviewed. However, it may be more efficient to simply obtain binned data only for those parameters that characterize the disease.

According to aspects of the invention, patterns (e.g., individual structural features or distributions) that are used to detect angiogenic vasculature and other abnormal blood vessels also can be used to monitor a disease response to treatment. For example, the total vascularity or any other volumetric analysis of angiogenic or other diseased vasculature, and the distribution of vessel size (e.g., a ratio of small to large blood vessels) can be used independently or together as indicators of disease progression or regression. In general, microvasculature disappears before macrovasculature if an anti-angiogenic treatment (or other disease treatment) is effective. Therefore, an effective treatment results in a shift in the distribution of blood vessel sizes towards larger vessels. An index of anti-angiogenic activity can be scored as either a loss of small blood vessels or a shift of observed blood vessels towards a single size (or both).

In another aspect, the parameters can be (or include) changes over time. For example, a structure present at a second time can be compared to a structure present at a first time. In one embodiment, a disease may be tracked pre-therapy and/or post-therapy. Naturally, additional time points can be used. The time points may depend on the condition being observed (e.g., is it the progression of a disease that is already identified, is it the screening of patient(s) over time). Time periods can be daily, weekly, monthly, annual, or shorter, intermediate or longer time periods. Time intervals may be a series of regular time periods. However, other time intervals may also be useful. In one embodiment, a patient-specific baseline is established and monitored over time. For example, vasculature changes in the colon, breast, or other tissue or organ can be monitored periodically.

In one aspect of the invention, a type of treatment may be determined by the degree or extent of abnormal vascular structures (e.g., angiogenesis) that is detected at one or more suspected disease loci (e.g., cancerous loci). For example, if a suspected cancerous locus or metastasis is pre-angiogenic or associated with early stage angiogenesis, it may be appropriate to monitor the locus without any form of treatment. However, an appropriate therapy may involve the administration of one or more angiogenesis inhibitors to prevent the formation of any new vasculature. If a suspected cancerous locus or metastasis is associated with mid-stage angiogenesis, an appropriate therapy may be the administration of one or more angiogenesis inhibitors. A patient with mid-stage angiogenesis at a suspected locus also should be monitored so that any further blood vessel development can be treated more aggressively. If a suspected cancerous locus or metastasis is associated with late stage angiogenesis, an appropriate treatment may involve at least one or more of chemotherapy (e.g., cytotoxic chemotherapy and/or hormone-based chemotherapy), radiation, surgery, and/or treatment with one or more angiogenesis inhibitors. However, it should be appreciated that any of the above treatment options may be used to treat a patient with any one or more lesions associated with any degree of angiogenesis.

Examples of angiogenesis inhibitors include but are not limited to 2-methoxyestradiol (2-ME), AG3340, Angiostatin, Angiozyme, Antithrombin III, VEGF inhibitors (e.g., Anti-VEGF antibody), Batimastat, bevacizumab (avastatin), BMS-275291, CAI, 2C3, HuMV833 Canstatin, Captopril, Cartilage Derived Inhibitor (CDI), CC-5013, Celecoxib (CELEBREX®), COL-3, Combretastatin, Combretastatin A4 Phosphate, Dalteparin (FRAGIN®), EMD 121974 (Cilengitide), Endostatin, Erlotinib (TARCEVA®), gefitinib (Iressa), Genistein, Halofuginone Hydrobromide (TEMPOSTATIN™), Id1, Id3, IM862, imatinib mesylate, IMC-IC11 Inducible protein 10, Interferon-alpha, Interleukin 12, Lavendustin A, LY317615 or AE-941 (NEOVASTAT™), Marimastat, Maspin, Medroxpregesterone Acetate, Meth-1, Meth-2, Neovastat, Osteopontin cleaved product, PEX, Pigment epithelium growth factor (PEGF), Platelet factor 4, Prolactin fragment, Proliferin-related protein (PRP), is PTK787/ZK 222584, ZD6474, Recombinant human platelet factor 4 (rPF4), Restin, Squalamine, SU5416, SU6668, SU11248 Suramin, Taxol, Tecogalan, Thalidomide, Thrombospondin, TNP-470, TroponinI, Vasostatin, VEG1, VEGF-Trap, and ZD6474.

Some embodiments may include a method of selecting a subject for treatment and/or selecting a treatment or a course of therapy based on the analysis of certain in situ vascular structures. A method may involve analyzing in situ vascular structure(s) in a human subject to obtain, for example, a score. The score may be compared to a control score (e.g., in an apparently healthy population) or to a previous score from a previous analysis on the same subject. The treatment or the course of therapy may be based on such a comparison. In some embodiments, obtaining an analysis of vascular structures is repeated so as to monitor the human subject's response to therapy over time. In some embodiments of this aspect of the invention, the method further comprises measuring a second index of disease in the human subject wherein deciding on the treatment or course of therapy is also based upon the measurement of said second index.

In certain embodiments, patients having a tumor that is under-vascularized (e.g., one that shows signs of necrosis) may be selected for treatment with one or more anti-angiogenic compounds. Under-vascularized tumors may be identified as those that have a low density of blood vessels, or for which the blood vessel diameters are low (e.g., below a threshold number typical of vascularized tumors).

Aspects of the invention also may include monitoring the effectiveness of a therapy by monitoring the presence of blood vessel patterns or features over time. For example, the progressive loss of blood vessels in a tumor in response to treatment may be a sign that a therapy is effective. In contrast, the absence of any impact on vascularization may be an indicator that a treatment is not being effective in a patient and that an alternative therapy should be considered or used.

It should be appreciated that some or all of the therapeutic aspects of the invention can be automated as described herein.

In one embodiment, aspects of the invention can be used to understand structural changes associated with biological processes of interest (e.g., disease development and progression). For example, an animal's vasculature can be analyzed to identify additional patterns (e.g., individual structural features or distributions or changes associated only with certain binned size ranges) that may be associated with wound healing or different diseases or different disease stages. These additional patterns (e.g., individual structural features or distributions) may be used in one of more of the diagnostic, intervention, therapeutic, and development aspects of the invention.

In one embodiment, aspects of the invention can be used to understand structural changes associated with medical procedures. For example, an animal's vasculature can be analyzed to identify changes associated with post-surgical wound healing or implant/transplant (including xenografts) growth or rejection.

It should be appreciated that some or all of the research aspects of the invention can be automated as described herein.

In another embodiment, aspects of the invention can be used in screens of compound libraries or to validate candidate compounds for treating diseases associated with abnormal internal structures (e.g., abnormal tubular networks). Aspects of the invention allow efficient high throughput analyses of internal structural changes using binned data (e.g., BMVD). These changes can act as surrogate markers (biomarkers) for certain diseases. As a result, the screening process can be automated to a large extent, and the time for obtaining results significantly shortened when compared to current validations that often involve waiting for disease symptoms to change and also may require tissue biopsies.

Aspects of the invention may be used for identifying and quantifying vascular patterns (e.g., structural features) that can be used as surrogate markers for diagnostic, therapeutic, and research and development purposes. Surrogate markers are useful for reducing the time of diagnosis, therapy evaluation, and drug development. A surrogate marker can be used as an early indicator for disease diagnosis, disease prognosis, or drug effectiveness, without waiting for a clinical outcome (e.g., increased survival time in response to a drug). So, a vasculature analysis can be used as a surrogate marker for drug development (in both pre-clinical and clinical trials), for clinical screening (e.g., breast, lung, or colon screening), and for clinical therapy monitoring. For example, binned vasculature structure may be a useful surrogate marker for angiogenesis related diseases such as cancer.

In one embodiment, aspects of the invention provide methods for screening and/or validating candidate compounds or therapies for their effectiveness in treating neovasculature formation and/or vasculature pattern changes associated with disease. Aspects of the invention may be used to evaluate individual or small numbers of compounds or to screen libraries to evaluate and/or identify a plurality of candidate compounds (e.g., by administering these compounds, individually or in groups, to an experimental animal such as a mouse and evaluating their effect on angiogenic vasculature). Libraries may contain any number of compounds (e.g., from approximately 100 to approximately 1,000,000) Different types of compounds can be screened, including antibodies, small molecules, etc., or any combination thereof. However, the invention is not limited by the number and/or type of compounds that can be evaluated.

In one embodiment, the effectiveness of a candidate compound can be compared to a reference compound. A reference compound can be any compound with a known effect on a structure. For example, Avastin (Genentech) is a known monoclonal antibody against vascular endothelial growth factor (VEGF) that can be used as a reference to test the effect of a candidate compound on neovasculature growth. Other examples of compounds include, but are not limited to, Sutent and Nexavar.

It should be appreciated that some or all of the development aspects of the invention can be automated as described herein.

It also should be appreciated that any one or more geometrical, structural, and/or distributional parameters described herein may be evaluated by comparison to a reference parameter. In some embodiments, a reference parameter may be an amount or score for that parameter in a normal or healthy subject. In other embodiments, a reference may represent a diseased condition. In some embodiments, a change or amount of any structural parameter that is correlated or associated with a disease or condition as described herein may be a statistically significant change or difference in that parameter in a diseased or test subject relative to a reference subject. In some embodiments, a difference or change in a structural parameter may be an increase or a decrease in a particular parameter (or a combination of parameters). An increase in a parameter may be at least a 5%, 10%, 20%, 30%, 40%, 50%, 60%, 70%, 80%, 90%, 100%, or greater increase in that parameter in a test subject relative to a reference subject. Similarly, a decrease in that parameter may be at least a 1%, 5%, 10%, 20%, 30%, 40%, 50%, 60%, 70%, 80%, 90%, 100%, or greater decrease of a measure of that parameter in a test subject relative to a reference subject. Once an amount of change or difference in a parameter has been correlated or associated with a disease or condition, that level may be used in subsequent methods according to the invention. Accordingly, in some embodiments, a difference of at least at least 1%, 5%, 10%, 20%, 30%, 40%, 50%, 60%, 70%, 80%, 90%, 100%, or more of any given structural parameter (e.g., tortuosity, density, volume, or any other individual structural feature or distribution of structures or structural features as described herein) within a data bin relative to a reference value may be used as a threshold for methods of the invention. It should be appreciated that higher or lower or intermediate values may be used. It also should be appreciated that different parameters may have different threshold or reference levels. Also, different parameters (and/or different levels for each parameter) may be associated with different conditions or diseases. Accordingly, specific disease or condition values or thresholds may be identified for different parameters or combinations thereof. These threshold values may be used for disease detection, diagnosis, monitoring, or for any other therapeutic, clinical, or research application described herein (e.g., in automated methods described herein).

Accordingly, aspects of the invention provide methods and devices for obtaining and/or analyzing data relating to internal tubular structures in casts and/or in human and/or other animal bodies. In some embodiments, methods of the invention involve analyzing one or more parameters (or parameter changes over time) for binned blood vessels that have been categorized based on their size. For example, blood vessels may be binned according to the following non-limiting diameter ranges: about 0-10 microns, about 10-25 microns, about 25-50 microns, about 50-75 microns, about 75-100 microns, about 100-150 microns, about 150-200 microns, about 200-300 microns, about 300-400 microns, about 400-500 microns, about 500-1,000 microns, or any combination thereof. However, any other suitable bin size ranges (including larger, smaller, or intermediate size ranges) may be used. In some embodiments, the number of different bins may be between about 2 and about 10. However, higher numbers of bins also may be used. In some embodiments, only 2 to 5 bins are used (e.g., 2, 3, 4, or 5). In certain embodiments, three blood vessel bin sizes are used: small, medium, and large. In some embodiments, a single bin is chosen having a predetermined size range and no other size ranges are analyzed.

Profiles may be extracted from the distribution of quantitative values for one or more structural features as described herein (including for example, features observed in vascular casts). In some embodiments, volume independent or density independent profiles may be extracted from distributions by comparing ranges within each distribution being analyzed (e.g., a subpopulation within a single range as a percentage of the total population across all ranges, or a ratio of subpopulations within a first and a second range that each represent different subsets the entire range of values).

Aspects of the invention may include the analysis of one or more regions of interest in animal disease models (e.g., in situ and/or in casts of one or more regions of interest). Animal disease models may be, but are not limited to, engineered (e.g., recombinant) animals, transgenic animals, metastatic cancer models, xenograft models, orthotopic transplant models, etc., or any combination thereof. In some embodiments, different animal models may have different known genetic markers (e.g., particular mutations) associated with a disease of interest (e.g., a cancer). Any suitable animal may be used as an animal model, including, but not limited to, a mouse, rat, hamster, guinea pig, pig, dog, cat, rabbit, zebrafish, or other suitable animal. It should be appreciated that whole experimental animals may be analyzed. However, in some embodiments, tissues and/or organs may be analyzed. In some embodiments, models may be based on xenografts (e.g., xenografts of cancer or tumor cells that will form cancer or tumor tissues in a host animal). For example, human cells may be introduced into a non-human host animal. Other uses of xenografts include analyzing responses to certain tissue and/or organ transplantation (e.g., a non-human tissue or organ into a human host). In some embodiments, vascular casts of regions of interest in an animal model may be obtained to thoroughly analyze the vascular structures, and/or changes therein, associated with the condition being modeled. In some embodiments, observations made on casts may be compared (e.g., using appropriate statistical techniques) to in vivo (e.g., in situ) observations to identify one or more common structural characteristics and/or changes that are statistically significant in vivo in association with a disease, condition, or response of interest. These can then be used in subsequent applications as described herein.

According to aspects of the invention, compounds and therapies can be evaluated in the context of an in-vivo model such as an animal disease model. For example, a mouse with cancer or atherosclerosis can be used to evaluate, optimize, and identify useful therapies. Other animal models also can be used. Aspects of the invention may be useful for high-throughput analyses because they can detect small changes in vasculature and can be used to evaluate a therapy in a short time period with minimal manipulation since little or no invasive procedures are required.

Vascular analysis aspects of the invention can be used on an orthotopic model to test, for example, the effectiveness of a drug in a short period of time. For example, the effect of a candidate drug on angiogenesis in an orthotopic mouse tumor model may be quantifiable after about 5 days (e.g., between 1 and 10 days, depending on the model and the drug). In contrast, a subcutaneous cancer animal model requires approximately one month for tumor growth to be analyzed and compared to controls.

An orthotopic model can be used to model different diseases or clinical conditions. Examples include, cancer, tissue regeneration, wound healing (including healing after traumatic injury, healing after surgical intervention, healing of burnt tissue such as skin), tissue or organ transplant therapy, medical device implant therapy, other conditions associated with neovascularization or changes in normal vascular structure, or any combination of two or more of the above. However, the invention is not limited by the type of orthotopic model or the type of disease or clinical condition that is being analyzed.

A single orthotopic disease model animal may be useful for testing more than one candidate drug molecule since the analysis does not involve sacrificing the model animal. Accordingly, once a test with a first candidate is complete, a subsequent candidate can be evaluated in the same model animal. A series of candidates can be tested in a single model animal, with appropriate controls, provided the model retains features of neovascularization that are necessary for the assay.

It should be appreciated that any of the geometrical, structural, and/or distributional parameters described herein may be used as biomarkers. Biomarkers of the invention can be qualified and/or quantified and compared using standard statistical methods. These biomarkers can be compared on individual basis, but also in combination as a signature of vascular morphology and function. Whole signatures can be compared between treated and untreated samples, or samples with physiological and pathological vascular pattern.

It should be appreciated that in some embodiments, one or more of the biomarkers described herein may be used to aid in the diagnosis, prognosis, prediction, or other medical application along with other types of physiological and or biological markers (e.g., physiological measurements, genetic markers, etc., or any combinations thereof).

It should be appreciated that aspects of the invention may be applied to features of vascular geometry (e.g., curvature, tortuosity, distributions of vascular structural features, etc., or any combination thereof) that are obtained from an analysis of vascular casts (e.g., using any suitable image analysis technique described herein or known in the art). In some aspects, vascular casts are analyzed to identify distributions of one or more blood vessel structural features (including, for example, abnormal excess or absence of blood vessels or blood vessel structures) that are associated with a disease or other condition of interest. Structural features identified in casts may be used as biomarkers or references to evaluate in situ vasculature, for example, to detect indicia of a disease or other condition of interest in a subject. Structural characteristics of vascular casts also may be used to evaluate therapeutic treatments, screen candidate compounds, and for other applications as described in more detail herein. In some embodiments, one or more structural parameters are analyzed over time (e.g., using a series of vascular casts obtained at different time points) to monitor and/or identify structural changes that occur during development, disease progression or regression, or in response to therapy. In some embodiments, structural analysis is performed on vascular casts obtained from experimental models (e.g., whole animal models, or organ or tissue models). However, in some embodiments, vascular casts are obtained and analyzed for one or more regions of interest (e.g., diseased regions) in dead animals, including for example dead humans (e.g., human cadavers).

As used herein, a vascular cast refers to a physical structure that is generated to represent blood vessels of an entire vasculature or portion thereof. A cast may be obtained by perfusing a vasculature or a vascular region (e.g., the blood vessels of an organ, for example, of a kidney or liver) with a casting material that solidifies (e.g., polymerizes) to form a stable structure. The surrounding tissue and cells (e.g., including the blood vessel walls) may be removed to reveal the cast. The cast retains the structural features of the original blood vessels. Cast may include structures of blood vessels of different sizes as described herein. Certain casts are more flexible than others, certain casts are more brittle than others. Vascular casts can be used to identify vascular structural features with high resolution and/or to identify correlations between structural features and conditions of interest with high degrees of confidence since the structures of the blood vessels are retained in the casts and other biological structures that could interfere with an analysis are removed. Vascular casts may be obtained using any suitable casting material. In some embodiments, the casting agent may be a polymer. In some embodiments, the casting agent may react with the blood vessel walls. Non-limiting examples of casting agents include, but are not limited to Microfil®, methyl methacrylate, prepolymerized methyl methacrylate (Mercox™), Mercox™ CL-2B, other acrylic resins, silicon, gold nanoparticles, Batson No. 17, polyurethane-based casting agents (e.g., PU4ii), etc., or combinations of two or more thereof.

It should be appreciated that casting agents may be supplemented with contrast agents and/or other detectable agents. Examples of contrast agents include, but are not limited to, $BaSo_4$ and UAc (e.g., mixed into the casting material). In some embodiments, already polymerized casts can be soaked in $OSO_4$ to achieve better contrast using CT imaging. In certain embodiments, any suitable heavy metal can be mixed into the resin to make it more radioopaque.

In some embodiments, a large volume of an animal body (e.g., the entire body) may be perfused with a casting agent composition. In certain embodiments, a small volume of an animal (e.g., a tissue, an organ or a region of either one thereof) may be perfused with a casting agent composition. In some embodiments, a casting agent may be perfused into a tissue or an organ or a region of either one thereof after removal from an animal (e.g., after biopsy or other surgical excision). In some embodiments, a casting agent composition may be perfused into a live animal. It should be appreciated that an animal may be sacrificed after perfusion with a casting agent depending, in part, on the amount and type of casting agent composition that is used and the tissue or organ to which the casting agent composition is targeted. According to aspects of the invention, casting agent(s) may be used to preserve in vivo structures for detailed analysis. In some embodiments, this analysis identifies particular structural or distribution properties that can be subsequently used as markers for in vivo diagnostic, therapeutic, research, and/or other applications in live animals (including humans).

In some aspects, vascular structures may be analyzed in situ in an animal after perfusion with a casting agent composition. In some aspects, a tissue or an organ or a region of either one thereof may be removed from an animal for analysis (e.g., before or after perfusion with a casting agent composition).

Accordingly, aspects of the invention can be used to represent and/or visualize blood vessels with a casting agent or medium.

Data relating to one or more selected structures (e.g., structural patterns obtained from an analysis of a vascular cast) may be obtained and/or analyzed to glean information about a physiological condition of an animal based on the structure (or changes in the structure). For example, patterns identified in casts may be used as biomarkers to screen in situ vasculatures for the presence of one or more similar patterns or to quantify the extent of the pattern in situ. This information may be used for diagnostic, predictive, prognostic, therapeutic, interventional, research and/or development purposes, as well as for grading and/or staging a disease. In some embodiments, methods of the invention may involve analyzing one or more structural parameters (or one or more structural parameter changes over time) based on binned structure data or information obtained for casts (e.g., vascular casts) or in situ structures (e.g., in vivo blood vessels).

In some embodiments, one or more structures and/or structural changes that are identified using casts may be detected or monitored in vivo to determine whether a predetermined disease, condition, or response is present in vivo.

In some embodiments, structural parameters and/or structural changes observed for vascular casts from experimental animals (or organs or tissues) can be used as references when analyzing vasculature in vivo. For example, structural vasculature parameters and/or changes that are identified in casts using experimental animal models subsequently can be detected or monitored in vivo (e.g., in a human subject) and used to evaluate the development of a disease, a drug response or other biological or disease property associated with the vasculature parameters and/or changes in a subject. In some embodiments, structural characteristics identified in vascular casts may be used to identify one or more patient subpopulations that are (or are predicted to be) more responsive to a particular treatment. For example, responsive subjects may be identified as those having one or more blood vessel characteristics that were associated with responsiveness in animal models and identified by analyzing vascular casts from the responsive animals.

One or more of the characteristics described herein, or combinations of characteristics, or related structural changes over time, may be identified as structural patterns that can be associated with one or more conditions of interest. Once identified, these patterns can be used as biomarkers to identify or monitor the conditions of interest in vivo in a subject, for example, by analyzing the in situ vasculature of the subject (or a portion thereof) and detecting the presence of and/or quantifying the extent of a specific vascular structural pattern.

Accordingly, one or more of the following non-limiting structural characteristics (e.g., combinations of 2, 3, 4, 5, 6, 7, 8, 9, 10 or all of the following structural characteristics) may be evaluated (e.g., quantified) in vascular casts and/or in situ (e.g., in vivo): diameter binned vessel distribution, mean vessel diameter distribution, branching point density, vessel branching distribution, angle of vessel branching distribution, interbranching distances, vessel density, vessel tortuosity, intervessel distances, luminal vessel surface, vessel dilation (changes in vessel diameter over a segment), sinosoidalation (dilation in sinosoids), or permeability (vessel leakiness). Distributions of the quantified characteristics may be prepared and analyzed (e.g., compared). However, it should be appreciated that other structural characteristics, for example, other characteristics described herein also may be analyzed by analyzing and comparing distributions of those characteristics or features.

For example, the quantification of any of the following non-limiting features may be performed and related distributions may be analyzed as described herein: Total Intra-Vascular Volume (TIVV)—e.g., over the entire Tumor Vascular Tree and Region of Interest (ROI), over only the Small Vessels Volume within the Total Volume (or the ROI), over only the Medium Vessels Volume within the Total Volume (or the ROI), or over only Large Vessels Volume within Total Volume (or the ROI); Intra-Vascular Volume Distribution (IVVD)—e.g., broken by Total Volume, Small, Mid & Large Vessels Volumes, color encoded into small, mid, large vessels on a segmented vascular tree (e.g., based on a Poker Chip representation), linked vascular volume values through color encoding of regions within a segmented vascular tree (e.g., on a Poker Chip representation), or detected locations/regions of Max Volume, Mid Volume, Min Volume and link to regions within a segmented vascular tree (e.g., based on a Poker Chip representation); Inter-Vessel Distance (IVD)—e.g., in the form of average/Min/Max values, histograms, values in select locations (for example single locations), color encoded Vessel Tree/ROI(s) with IVD values & IVD Value Clusters; Inter-Branching Distance (IBD)—e.g., in the form of average/Min/Max values, histograms, values in select locations (for example single locations), color encoded Vessel Tree/ROI(s) with IBD values and IBD Value Clusters; Vascular Diameter Variability (VDV) along the length of the vessel—e.g., in the form of histograms for the entire vascular tree or w/in a ROI, with the ability to view such variability for a single vessel or a group of vessels on the whole tree of within select (ROI)s, or color encoded segments within a tree/ROI (e.g., based on a Poker Chip representation) based on VDV values; Vessel Branch Curvature (VBC) and Tortuosity (VBT)—e.g., in the form of histograms of each BC and BT for the entire vascular tree or within select ROI(s), with the ability to view such variability for a single vessel or a group of vessels on the whole tree or within select ROI(s), or color encoded regions within a vascular tree/ROI (e.g., color encoded chips a Poker Chip representation) based on BC or BT values; or any combination of two or more thereof. Distributions of one or more of these characteristics, or combinations of characteristics, or related structural changes over time, may be identified as structural patterns that can be associated with one or more conditions of interest.

Blood vessels may be binned according to about any of the following non-limiting diameter ranges (in microns): 0-10, 10-25, 25-50, 50-75, 75-100, 100-150, 150-200, 200-300, 300-400, 400-500, 500-1,000, or any combination thereof. However, any other suitable bin size ranges (including larger, smaller, or intermediate) may be used. In some embodiments, the number of different bins may be between about 2 and about 10. However, higher numbers of bins also may be used. In some embodiments, only 2 to 5 bins are used (e.g., 2, 3, 4, or 5). For example, three blood vessel bin sizes may be used: small, medium, and large diameters (e.g., small at less than about 35 microns or about 20-35 microns, medium about 35-70 or about 35-100 microns, and large above about 100 microns or about 100-200 microns). However, other vessel size ranges may be used to calculate population percentages or ratios as described herein. In some embodiments, a single bin is chosen with a predetermined size range and no other sizes are analyzed.

In some embodiments, a parameter may be evaluated as a percentage of the total population of vessels. For example, the percentage of blood vessels having a particular diameter (e.g., 20-40 microns) as a percentage of the total population of blood vessels may be used. In some embodiments, a parameter may be evaluated as a ratio of two subpopulations within a population of vessels. It should be appreciated that the percentage populations of vessels having different properties may be evaluated by determining the relative lengths of blood vessels having different properties within a region being analyzed. However, other techniques may be used.

Aspects of the invention relate to business methods that may involve the marketing and/or licensing of biomarkers associated with particular biological processes, conditions, and/or diseases. In some embodiments, patterns (e.g., geometric features) of blood vessels (e.g., observed in vivo or in casts) are analyzed to identify or evaluate associations or correlations with certain biological processes, conditions, and/or diseases of interest. Pattern parameters may be identified that can be used as structural biomarkers (e.g., for clinical, diagnostic, therapeutic, and/or research applications as described herein). These biomarkers may be used to reduce the cost and increase the efficiency and sensitivity of medical and research techniques. In one embodiment, one or more biomarkers or methods of using the biomarkers may be marketed to medical or research customers or potential customers. In one embodiment, a fee-based service may be provided to medical or research organizations wherein information relating to a medical image is obtained and analyzed for the presence of one or more biomarkers and the resulting information is returned in exchange for a fee. The amount of the fee may be determined, at least in part, by the type of image information that is provided, the type and degree of analysis that is requested, and the format and timing of the analysis. It should be understood that aspects of the invention may be applicable to image information obtained from one or more of many different scanning modalities (including, but not limited to, micro CT, MDCT, rotational angiography, MRI, PACS). This information may be received from many different sources, including, but not limited to one or more of the following: medical centers, large pharmaceutical companies (e.g., in association with pre-clinical evaluations or during clinical trials), CROs (for both pre-clinical and clinical analyses), medical laboratories and practices (e.g., scanning centers), hospitals, clinics, medical centers, small biotechnology companies (e.g., in association with pre-clinical evaluations or during clinical trials), and biomedical research organizations. The results of the analysis then may be returned to any one of these organizations. In some embodiments, the analysis results may be returned to the same entity that sent the image information. In other embodiments, the results may be returned to a different entity (e.g., the image information may be received from a scanning laboratory and the analysis may be returned to a physician). One or more steps involved with receiving the information, analyzing the structural features, processing the results and forwarding the results to a recipient may be automated. It also should be appreciated that one or more of these steps may be performed outside the United States of America. Business procedures (e.g., marketing, selling, licensing) may be performed individually or collaboratively.

Aspects of the invention may be described herein in the context of individual analytical steps, particular structural features, etc. However, it should be appreciated that any of the methods and devices described herein also may be incorporated into a business method associated with the use of a biomarker based on one or more blood vessel structural features or patterns (e.g., structural features or changes observed in vascular casts obtained from therapeutic and/or disease models or conditions).

Aspects of the invention may be automated (e.g., using one or more computer-implemented acts described herein). It should be appreciated that one or more pattern parameters (e.g., individual blood vessel structural feature(s), distributions of blood vessels or blood vessel structural features, or combinations thereof) may be analyzed using one or more quantitative and/or qualitative methods (e.g., based on binned data). In some embodiments, one or more parameters may be measured and quantified and the measurements may be analyzed using standard quantitative and/or statistical techniques for evaluation and/or comparison with threshold or reference values as described herein. In certain embodiments, one or more parameters may be evaluated using a predetermined scoring method, for example based on predetermined factors (e.g., for binned data). Geometrical parameters may be represented using vectors. For example, a distribution of blood vessels, blood vessel curvatures, blood vessel tortuosity, or blood vessel directions within a volume of interest may be represented using a plurality of vectors. Separate vectors may be used to represent separate vessels (e.g., vessels for which a connectivity has not been determined during the analysis). However, separate vectors also may be used to represent individual segments or fragments of a single blood vessel or portion of a vascular tree (e.g., for which connectivity has been or may be determined during the analysis). Vasculature pattern parameters may be analyzed using any appropriate technique for separating and/or categorizing numerical values or scores.

In some embodiments, a score may be obtained to relate a pattern parameter to the probability of a physiological condition such as a disease or disease stage. Aspects of the invention can be used for in situ diagnostic, interventional and therapeutic analysis of one or more disease loci associated with aberrant internal structures. As used herein "in situ" means in an animal (e.g., a human) body as opposed to in a biopsy or other tissue sample. Aspects of the invention can be used to research structural changes associated with a disease, for developing and evaluating disease treatments including therapeutic drugs, and for other purposes. Aspects of the invention include automatically analyzing a structural feature or pattern and automatically generating a score based on the analysis.

In some embodiments, aspects of the invention include detecting and/or analyzing selected internal tubular networks in situ in animals and/or in vascular casts. As used herein, an internal tubular network means a network of connected cylindrical internal body structures. Tubular networks include, but are not limited to, cardiovascular, respiratory, gastro-intestinal, and genito-urinary systems and portions thereof within animal bodies. Accordingly, the cylindrical structures may include branched, straight, curved, and/or twisted cylindrical elements. The cylindrical structures and elements may include not only cylinders, but also may include flattened or otherwise distorted regions. The cross-section of a cylindrical structure or element may be circular, oval, approximately circular, approximately oval, or more irregular in nature. The internal diameter of the cylindrical elements may vary or may be approximately the same over the region of interest. A tubular network such as a circulatory network may be closed off from the environment outside the animal. In contrast, tubular networks such as respiratory and gastro-intestinal networks may be open to the outside environment. In some embodiments, appropriate casting and/or contrast agents (e.g., inhaled agents) may be used to analyze respiratory and/or gastro-intestinal networks.

In one embodiment, aspects of the invention include analyzing a representation of a tubular network (e.g., a mathematical representation of a vascular network). In one embodiment, a representation of a network, or a portion thereof, may be obtained (e.g., from an existing database or a remote site) and analyzed. In another embodiment, a representation of a network, or a portion thereof, may be generated from structural data and then analyzed. According to aspects of the invention, an analysis may include detecting the presence or absence of one or more structural features or patterns, measuring or evaluating the extent of one or more structural features or patterns, or a combination thereof.

In one embodiment, aspects of the invention are useful for selectively detecting and/or analyzing patterns (e.g., structures) of an animal's vasculature to detect or monitor one or more blood vessel patterns (e.g., structures) that may be indicative of a physiological condition of the animal. A structural pattern or feature may be detected and/or analyzed for blood vessels of any size including, but not limited to, arteries, arterioles, veins, venules, and capillaries.

In one embodiment, aspects of the invention are useful for selectively detecting and/or analyzing structural features or patterns of an animal's vasculature to detect or monitor one or more blood vessel structures that are characteristic of disease (e.g., a disease associated with angiogenesis). A blood vessel structure or pattern characteristic of a disease (e.g., a disease associated with angiogenesis) may provide an early diagnostic indication of the presence of the, which can allow for early treatment that can improve a patient's prognosis. In other embodiments, a blood vessel structure or pattern characteristic of a disease (e.g., a disease associated with angiogenesis) can be used as a marker (e.g., a biomarker) for staging and/or grading, to monitor disease progression, evaluate a prescribed therapy, and/or identify and/or validate a drug or treatment regimen for the disease. Diseases associated with abnormal vasculature structures or patterns include, but are not limited to, cancer, cardiovascular, dermatologic (skin), arthritic, musculoskeletal, central nervous system, neurologic, pulmonary, renal, gastrointestinal, gynecologic, genitourinary, inflammatory, infectious, and immunologic diseases.

A cancer may be a solid tumor or a leukemia. When the cancer is a leukemia, methods of the invention may be directed to detecting and/or analyzing vasculature pattern(s) in the bone marrow of an animal (e.g., human).

It also should be appreciated that aspects of the invention may include performing any combination of two or more acts described herein and that certain acts may be omitted in some embodiments. In one embodiment, the presence of one or more structural abnormalities may be identified or detected in a body region without generating and/or analyzing a structural representation of that body region. For example, the presence of a blood vessel abnormality may be detected directly from structure data for a body region without generating a structural representation of the vasculature for that entire body region. In another embodiment, an analysis may involve selectively representing one or more abnormal structures if they are present in a body region without representing normal structures in that body region (e.g., abnormal blood vessel structures may be represented without representing any normal blood vessels, or without representing all the normal blood vessels, without representing most of the normal blood vessels, etc.). In another embodiment, an abnormal vascular structure may be identified or detected without obtaining a detailed representation of the all the blood vessels in a body region. It may be sufficient to detect the presence of or outline of a vascular tree in a body region and perform an analysis that identifies or detects abnormal structures on specific blood vessels or the presence of excessive vascularization (e.g., a clump of neovasculature representing malignancy) without representing all the normal details of the vascular tree or even detecting individual blood vessels in the vascular tree. Accordingly, in some aspects a low resolution data set for a body region may be sufficient to detect or identify certain structural indicia of a disease such as cancer.

Aspects of the invention may include automating one or more acts. For example, an analysis may be automated in order to generate an output automatically. Acts of the invention may be automate using, for example, a computer system.

As should be appreciated from the foregoing, in one embodiment, raw or processed structure data may be obtained at a medical or research center and sent to a computer at a remote site where one or more of the analytical steps described above may be performed (e.g., for a fee). The output from the analysis may be then returned to the medical or research center either in computer readable form to a computer at the medical or research center, in a hard copy, in another tangible form, or in any other suitable form including those described herein.

In another embodiment, one or more software programs that implement one or more functionalities described herein may be provided and installed at a medical or research center (e.g., for a fee). The programs can be provided on disk, downloaded from an internal or remote (e.g., external) site, or loaded in any suitable manner. Reference information that is used in any functionality described herein may be provided along with the software or separately. In one embodiment, reference information (e.g., information relating to normal or abnormal blood vessel structures) may be available on disk, downloaded from an internal or remote (e.g., external) site, or loaded in any suitable manner.

As used herein, "remote" means at a site that is different from the immediate location of the imaging device (e.g., the medical scanner). The remote site can be a central computer or computing facility at a hospital, medical, or research center (e.g., within the network or intranet of the center), or can be outside the hospital, medical, or research center (e.g., outside the network or intranet of the center). The remote site can be in the same state, in a different state, or in a different country from the site of data acquisition by the imaging device.

In some embodiments, multimodal analyses (e.g., using structure data from two or more different types of imaging devices) may be used together. Accordingly, aspects of the present invention may include the ability to process and analyze different types of structure data and either combine the results to generate a combined output, or to generate a separate output is generated for each imaging modality. In some embodiments, an organ, tissue, or animal perfused with a casting agent and/or an imaging agent may be sent to an imaging center for analysis.

In some embodiments, in vivo and/or ex vivo casting methods of the invention can be used to identify one or more vascular patterns (e.g., including one or more structural parameters, structure distributions, combinations thereof) and/or time-dependent changes thereof that can be used as biomarker(s) for a disease or a response to a therapy, or for monitoring patients for indicia of disease or response to therapy, or for other applications where vascular information may be informative. Accordingly, such vascular patterns or changes thereof identified according to methods of the invention can be used for diagnostic, interventional, therapeutic, research, and treatment development and evaluation. Non-limiting examples of some of these embodiments are described below.

EXAMPLES

Example 1: Xenotopic Tumor Models

A tumor model can be generated by inoculating human non-small cell lung tumor cell line (A549 from ATCC, Inc.) subcutaneously in immunodeficient mice (SCID). SCID male mice (6-8 weeks old from Charles River Inc.) are inoculated subcutaneously in the lower back with a suspension of $1\times10^6$ human lung tumor cells (A549) in 0.2 ml of PBS. All mice are fed normal chow diet throughout the duration of the experiment. All mice weights are measured throughout the experiment. Tumor size is measured with calipers twice-a-week and tumor volume is calculated using the formula Length$^2 \times$Width$\times$0.52. All mice are randomized into two treatment groups (approximately 10 mice per group) when the median tumor volume reaches approximately 500 mm$^3$. The treatment groups can be treated according to the following schedule using intraperitoneal (i.p.) administration of either a control composition or an anti-angiogenic compound. For example, different levels of an anti-angiogenic compound can be used and the results compared to a control group that is not treated with an anti-angiogenic compound (e.g., Avastin® available from Genentech, South San Francisco, Calif.). For example:

Group 1: Control group—treated with saline/PBS twice a week.

Group 2: High Avastin®—treated with Avastin® at 5 mg/kg/i.p. twice a week.

Group 3: Low Avastin®—treated with Avastin® at 0.5 mg/kg/i.p. twice a week.

Experiments are terminated 1.5 weeks after initial treatment.

At the end-point, all mice are anesthetized and systemically perfused with a casting agent.

Example 2: Perfusion with Casting Agent

Perfusion with a casting agent, Mercox (available from Ladd Research, Williston, Vt.) can be performed as follows. An initial anticoagulation step for each animal is performed using an i.v. injection of heparin (10,000 U/ml, 0.3 cc/mouse). After 30 minutes, the animals are anesthetized. Each animal's heart is cannulated and the animal perfused with warm physiological saline at physiological pressure (with an open vein draining the organ or with an open vena cava). Perfusion is continued until the organ or animal is clear of blood. Mercox monomer is filtered through a 0.5 μm filter and a casting resin is prepared by mixing 8 ml Mercox, 2 ml methylmethacrylate, and 0.3 ml catalyst. The resin is infused through the same cannula until the onset of polymerization (the resin changes color to brown and emits heat, ~10 min). The organ or animal is carefully immersed in a 60° C. water bath for 2 hours (or overnight in a sealed container). The tissue is removed by incubating in alternating rinses of 5% KOH and distilled water (for example in a 60° C. water bath sealed) followed by thorough rinsing in distilled water. The cast is cleaned in 5% formic acid for 15 minutes and rinsed thoroughly in distilled water and frozen in distilled water. The resulting block of ice is lyophilized (care should be taken not to melt the ice, the ice should melt as it lyophilizes). The resulting cast can be analyzed to identify one or more structural characteristics of interest.

Example 3: Xenotopic Tumor Models Response to Anti-Angiogenic Therapy

Figure 14:
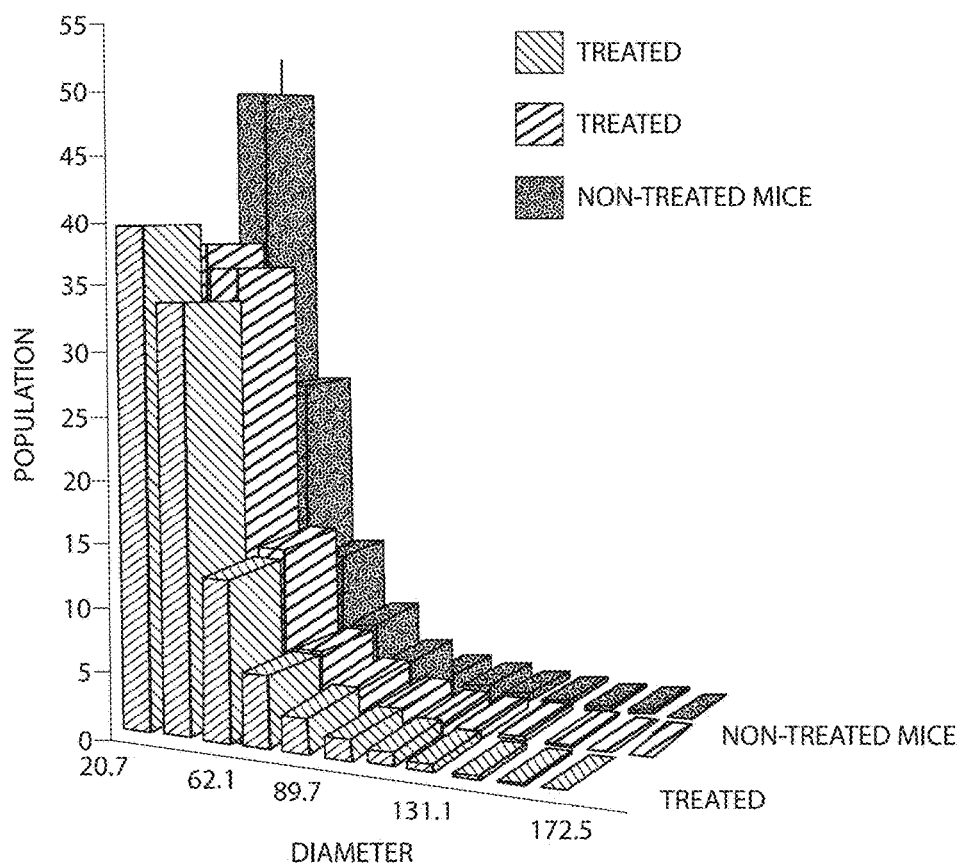
FIG. 14 illustrates blood vessel size distribution in an example of casts of a xenograft tumor model after treatment with Avastin® (an anti-angiogenic agent available from Genentech, South San Francisco, Calif.), in accordance with some embodiments of the present invention.
Figure 15:
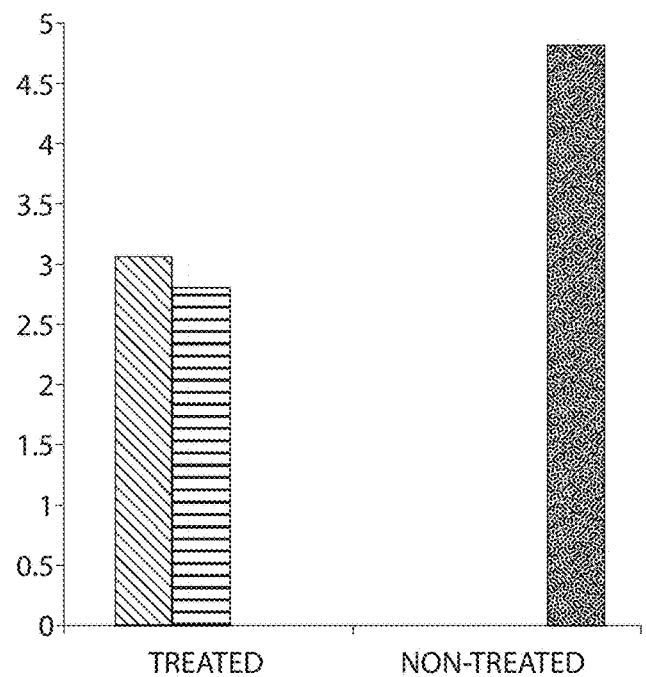
FIG. 15 illustrates the vessel population ratio between small and middle size vessels in an example of casts of a xenograft tumor model after treatment with Avastin®, in accordance with some embodiments of the present invention.
Figure 16:
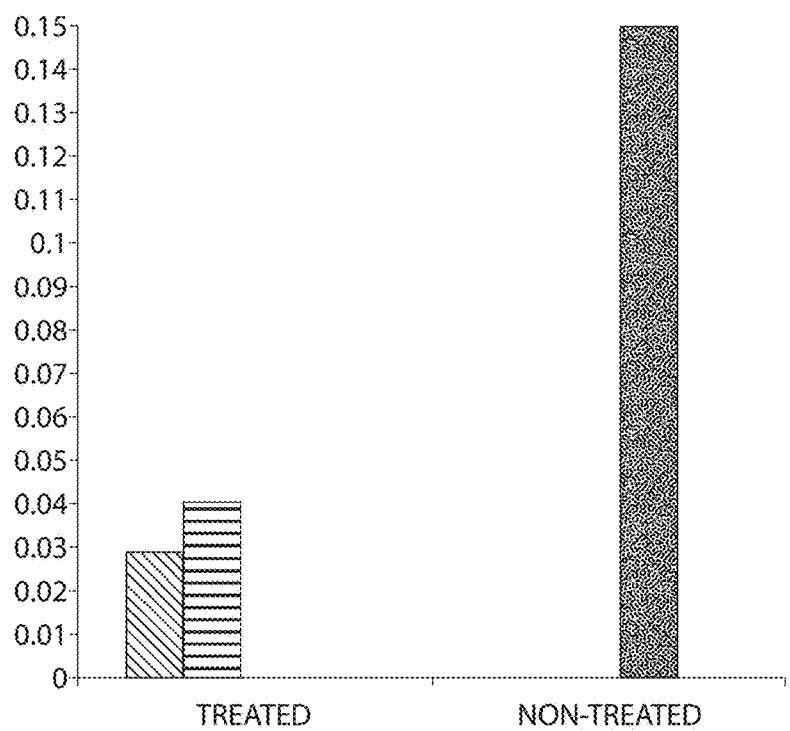
FIG. 16 illustrates the vessel population ratio between large and middle size vessels in an example of casts of a xenograft tumor model after treatment with Avastin®, in accordance with some embodiments of the present invention.
Figure 17:
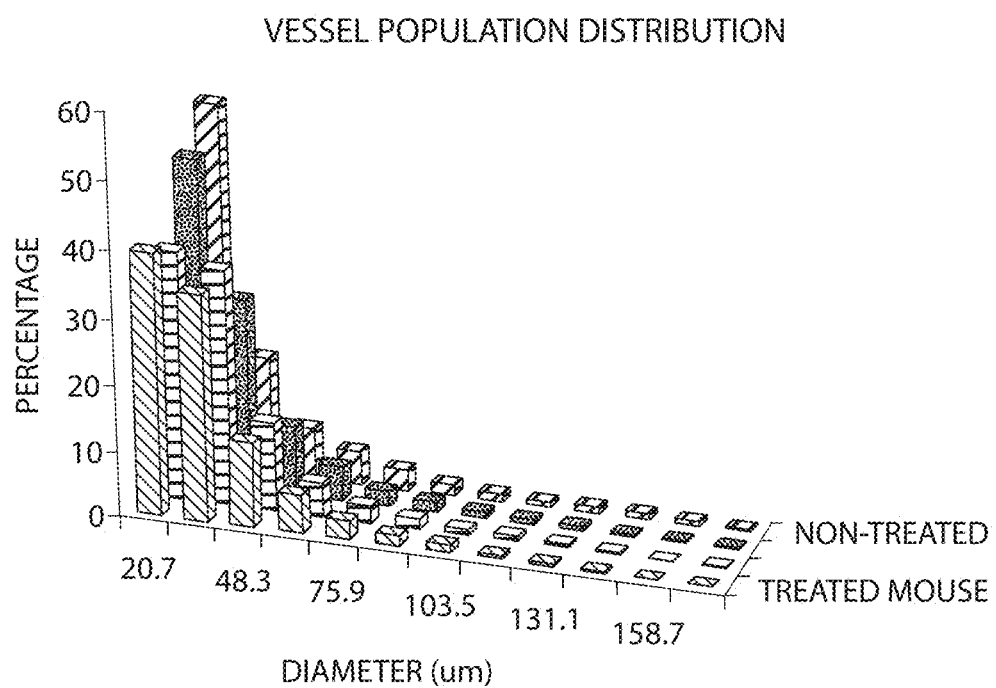
FIG. 17 illustrates the vessel population distribution in an example of casts of a tumor model after treatment with Avastin®, in accordance with some embodiments of the present invention.
Figure 18:
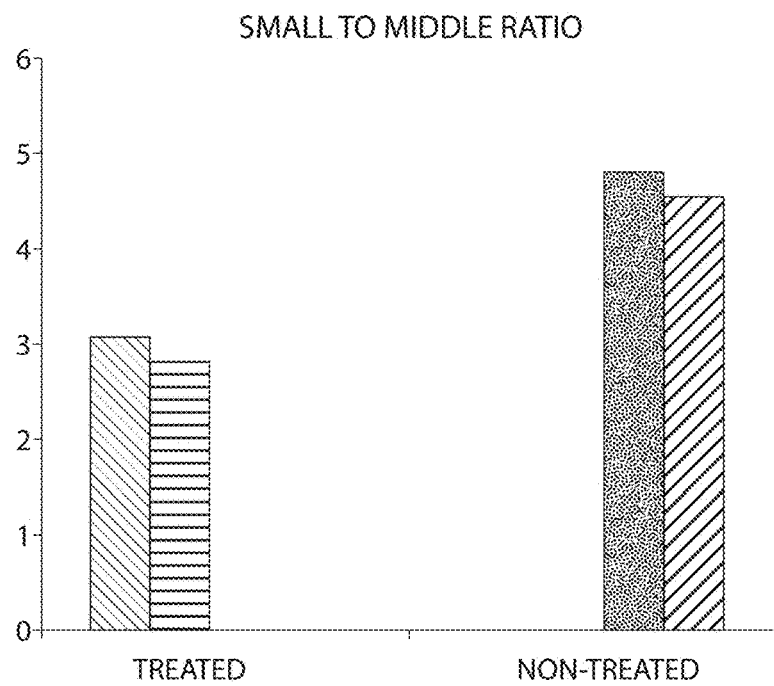
FIG. 18 illustrates the vessel population ratio between small and middle size vessels in an example of casts of a tumor model after treatment with Avastin®, in accordance with some embodiments of the present invention.
Figure 19:
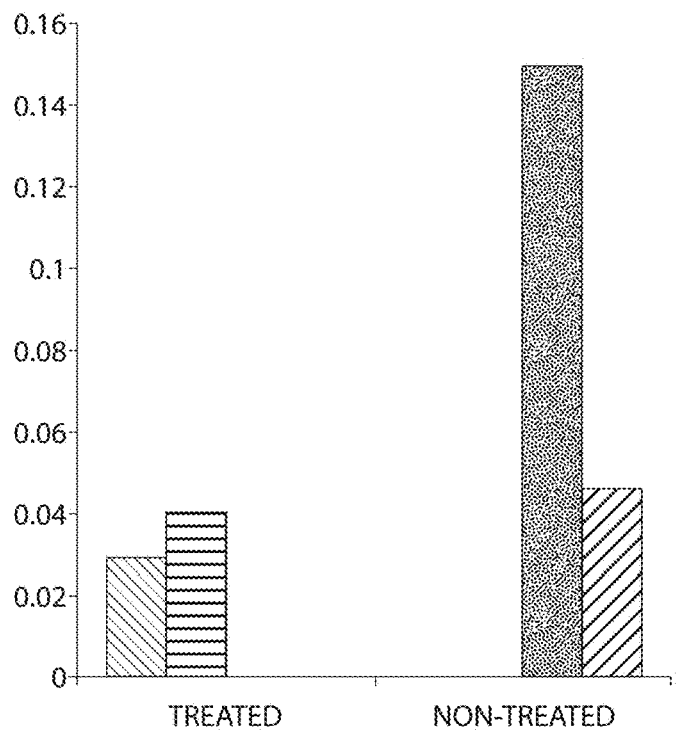
FIG. 19 illustrates the vessel population ratio between large and middle size vessels in an example of casts of a tumor model after treatment with Avastin®, in accordance with some embodiments of the present invention.

Xenotopic mouse models obtained as described in Example 1 were treated with either a control solution of saline/PBS or an anti-angiogenic preparation of Avastin® at 0.5 mg/kg/i.p. as described above. At the end-point, vascular casts were prepared as described in Example 2 above and analyzed for two treated mice (both treated with Avastin® at 0.5 mg/kg/i.p.) and one control mouse. The resulting vascular casts were scanned using a micro CT-scanner and the results of the structural analysis are shown in FIGS. 14-17. The analysis was performed by determining the number of blood vessels within bins of different diameter ranges for the xenotopic tumor in the treated and control animals. The bins were each 13.8 μm wide and the smallest bin included blood vessels having a diameter of between 20.7 μm and 34.5 μm. Mean tumor volumes did not differ significantly between the groups at the end of the experiment. However differences in blood vessel diameter distributions were detected as shown in FIGS. 14-17. FIG. 14 shows the resulting vessel population distribution. Treated tumors had 20% less small diameter sized vessels than untreated tumors, and treated tumors had a higher percentage of middle diameter sized vessels than untreated tumors. The blood vessel population distributions were consistent for both treated animals. FIG. 15 shows the vessel population ratio between small (approximately 21-35 μm) and middle (approximately 35-49 μm) size vessels in the tumors of the control and treated animals. The ratio decreased after inhibitor treatment with Avastin®, and this ratio was consistent within the treated group. FIG. 16 shows the vessel population ratio between large (approximately 147-161 μm) and middle (approximately 33-77 μm) size vessels. The ratio decreased after treatment with Avastin®, and this ratio was consistent within the treated group. Additional experimental results are shown in FIGS. 17-19.

The following considerations apply to the specific examples and the entire written specification herein (including the summary, detailed description, and claims). It should be appreciated that casts, like in situ blood vessels, are three-dimensional structures. Accordingly, imaging and analytical techniques described herein provide information about three-dimensional structural characteristics. In some embodiments, techniques are used to generate three-dimensional representations of vascular casts and/or in situ blood vessels. In some embodiments, techniques are used to generate three-dimensional images of vascular casts and/or in situ blood vessels. The three-dimensional representations and/or images can be analyzed as described herein.

However, it should be appreciated that aspects of the invention are not limited to three-dimensional structural characteristics. In some embodiments, aspects of vascular casts and/or in situ blood vessels may be represented and/or imaged in one or two dimensions and an analysis of one or two-dimensional features may be performed and used as described herein. It also should be appreciated that the structural features described herein may be measured or quantified using any appropriate units, including numbers, lengths or distances, angles, percentages, etc., or any combination thereof, further including any of these units as a function of volume or area. Similarly, it should be appreciated that vascular changes over time or in response to treatment may involve an increase or a decrease of one or more of these structural features. For example, an increase in structures associated with angiogenesis may be associated with certain disease progressions. In contrast, a decrease in structures associated with angiogenesis may be associated with disease regression (e.g., in response to treatment).

It also should be appreciated that descriptions herein related to obtaining distributions of quantitative values for vessel parameters within a region of interest are preferably based on methodologies that detect and quantify all or substantially all of the detectable vessels within the region of interest based on the detection technique that is used for that analysis. Different techniques may have different efficiencies. However, profiles and comparisons are preferably based on data from the same or equivalent detection and/or reconstruction techniques. It also should be appreciated that comparisons and/or analyses described herein may involve a statistical analysis using one or more standard statistical techniques to determine whether a change in a structure or pattern or other characteristic described herein (e.g., an increase or decrease over time, or in response to a therapeutic drug), or a difference or similarity between two structures or patterns or other characteristics described herein are statistically significant.

Having thus described several aspects of at least one embodiment of this invention, it is to be appreciated various alterations, modifications, and improvements will readily occur to those skilled in the art. Such alterations, modifications, and improvements are intended to be within the spirit and scope of the invention. Any suitable analytical techniques may be used for perfused tissue and organs according to the methods described herein, including for example, the analytical techniques that are described in PCT US2005/047081 and PCT US2007/026048 the disclosures of which are incorporated herein by reference in their entirety. Accordingly, the foregoing description and embodiments are by way of example only. In the event of conflict between different disclosures, the disclosure of the present application shall control.

It should be appreciated from the foregoing, there are numerous aspects of the present invention described herein that can be used independently of one another or in any combination. In particular, any of the herein described operations may be employed in any of numerous combinations and procedures. In addition, aspects of the invention can be used in connection with a variety of types of images or any dimensionality. Moreover, one or more automatic operations can be used in combination with one or more manual operations, as the aspects of the invention are not limited in this respect. Distribution analyses, however obtained, may be used to facilitate the characterization of any of various morphological changes to tissue and/or to assist in assessing the efficacy of treatment using any of the herein described techniques, alone or in combination.

The herein-described embodiments of the present invention can be implemented in any of numerous ways. For example, the embodiments of automatic distribution analysis may be implemented using hardware, software or a combination thereof. When implemented in software, the software code can be executed on any suitable processor or collection of processors, whether provided in a single computer or distributed among multiple computers. It should be appreciated that any component or collection of components that perform the functions described herein can be generically considered as one or more controllers that control the herein-discussed functions. The one or more controllers can be implemented in numerous ways, such as with dedicated hardware, or with general purpose hardware (e.g., one or more processors) that is programmed using microcode or software to perform the functions recited herein.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code. It should be appreciated that one embodiment of the invention is directed to a computer-readable medium or multiple computer-readable media (e.g., a computer memory, one or more floppy disks, compact disks, optical disks, magnetic tapes, etc.) encoded with one or more programs that, when executed, on one or more computers or other processors, perform methods that implement the various embodiments of the invention discussed herein. The computer-readable medium or media can be transportable, such that the program or programs stored thereon can be loaded onto one or more different computers or other processors to implement various aspects of the present invention as discussed herein. It should be understood that the term "program" is used herein in a generic sense to refer to any type of computer code or set of instructions that can be employed to program a computer or other processor to implement various aspects of the present invention as discussed herein. Additionally, it should be appreciated that according to one aspect of this embodiment, one or more computer programs that, when executed, perform methods of the present invention need not reside on a single computer or processor, but may be distributed in a modular fashion amongst a number of different computers or processors to implement various aspects of the present invention.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A method of extracting vessel geometry from one or more scan images, comprising:
    determining a scale for a voxel in the one or more scan images;
    determining an orientation of the voxel;
    applying a matched filter using the scale and orientation to generate a filter response;
    determining, based on the filter response, whether the voxel represents a centerline of a vessel;
    repeating the above acts to identify a plurality of centerline voxels; and
    linking the plurality of centerline voxels together, wherein the linking comprises selecting a second voxel to link to a first voxel based on a likelihood that the second voxel is adjacent to the first voxel and part of the same vessel, wherein the likelihood is calculated by:
    determining a distance between the first voxel and other voxels;
    determining a difference between the orientation of the first voxel and other voxels; and
    determining a difference between the filter response of the first voxel and other voxels.

2. The method of claim 1, wherein the scale is determined using a scale detection filter.

3. The method of claim 1, wherein the orientation is determined using the scale.

4. The method of claim 1, wherein the vessel geometry comprises a poker chip representation at each of the centerline voxels, the poker chip representation including a location of the centerline voxel, a radius, and a direction.

5. The method of claim 4, further comprising sorting the centerline voxels into bins based on radius.

6. The method of claim 5, wherein a binned micro-vessel density (BMVD) analysis is performed using the bins.

7. The method of claim 6, wherein the BMVD is used to detect and diagnose diseases associated with tubular networks.

8. The method of claim 6, wherein the BMVD is used to track disease progression.

9. The method of claim 6, wherein the BMVD is used to monitor a response to therapy.

10. The method of claim 1, wherein distance between the first voxel and other voxels is weighted more heavily than other criteria.

11. The method of claim 1, wherein a curve representing the centerline of the vessel is obtained by integrating orientation vectors for all centerline voxels in the vessel.

12. The method of claim 11, wherein a curvature of the vessel is obtained using derivatives of the orientation vectors.

* * * * *